(12) United States Patent
Cool et al.

(10) Patent No.: US 10,596,296 B2
(45) Date of Patent: Mar. 24, 2020

(54) HEPARAN SULPHATES

(71) Applicant: Agency for Science, Technology and Research, Singapore (SG)

(72) Inventors: Simon Cool, Singapore (SG); Victor Nurcombe, Singapore (SG); Jonathan Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/307,407

(22) PCT Filed: Apr. 30, 2015

(86) PCT No.: PCT/SG2015/050092
§ 371 (c)(1),
(2) Date: Oct. 28, 2016

(87) PCT Pub. No.: WO2015/167401
PCT Pub. Date: Nov. 5, 2015

(65) Prior Publication Data
US 2017/0043053 A1 Feb. 16, 2017

(30) Foreign Application Priority Data
Apr. 30, 2014 (SG) .......................... 10201401967W

(51) Int. Cl.
| | | |
|---|---|---|
| *A61L 27/20* | (2006.01) | |
| *A61L 27/38* | (2006.01) | |
| *A61L 27/52* | (2006.01) | |
| *A61L 27/54* | (2006.01) | |
| *A61K 31/727* | (2006.01) | |
| *C08B 37/00* | (2006.01) | |
| *C07K 14/495* | (2006.01) | |
| *A61L 15/44* | (2006.01) | |
| *A61L 15/60* | (2006.01) | |
| *A01N 1/02* | (2006.01) | |
| *A61K 8/73* | (2006.01) | |
| *A61L 27/34* | (2006.01) | |
| *C12N 5/0775* | (2010.01) | |

(52) U.S. Cl.
CPC ............ *A61L 27/20* (2013.01); *A01N 1/0226* (2013.01); *A61K 8/735* (2013.01); *A61K 31/727* (2013.01); *A61L 15/44* (2013.01); *A61L 15/60* (2013.01); *A61L 27/34* (2013.01); *A61L 27/3834* (2013.01); *A61L 27/52* (2013.01); *A61L 27/54* (2013.01); *C07K 14/495* (2013.01); *C08B 37/0075* (2013.01); *C12N 5/0662* (2013.01); *A61L 2300/414* (2013.01); *A61L 2420/02* (2013.01); *A61L 2430/06* (2013.01); *C12N 2501/15* (2013.01); *C12N 2501/91* (2013.01)

(58) Field of Classification Search
CPC ... C08B 37/0075; A61K 31/727; A61L 27/20; A61L 27/34; A61L 27/3834; A61L 27/52; A61L 27/54
See application file for complete search history.

(56) References Cited

U.S. PATENT DOCUMENTS

| | | | | |
|---|---|---|---|---|
| 5,807,982 | A | 9/1998 | McCaffrey et al. | |
| 5,843,442 | A * | 12/1998 | Soule .................... | C07K 16/40 424/145.1 |
| 9,498,494 | B2 | 11/2016 | Cool et al. | |
| 2003/0175257 | A1* | 9/2003 | Song ...................... | A61K 35/32 424/93.21 |
| 2015/0011505 | A1* | 1/2015 | Ekre ................... | C08B 37/0075 514/56 |
| 2015/0328251 | A1 | 11/2015 | Cool et al. | |
| 2017/0106012 | A1 | 4/2017 | Cool et al. | |

FOREIGN PATENT DOCUMENTS

| | | |
|---|---|---|
| JP | H05-132501 A | 5/1993 |
| WO | WO-2010/029278 A2 | 3/2010 |

OTHER PUBLICATIONS

Sigma-Aldrich entry for "Heparin vs Heparan Sulfate Proteoglycans" https://www.sigmaaldrich.com/technical-documents/articles/biology/what-is-heparin.html, accessed from the internet Nov. 14, 2018 (Year: 2018).*
Murali, S. et al "Affinity-selected heparan sulfate . . . " Biomaterials, vol. 34, pp. 5594-5605 (Year: 2013).*
Madry, H. et al "Transforming growth factor beta-releasing scaffolds . . . " Tissue Eng.: Part B, vol. 20, No. 2, pp. 106-125 (Year: 2014).*
International Search Report for PCT/SG15/50092, 5 pages (dated Jul. 6, 2015).
Lyon, M. et al., The interaction of the transforming growth factor-βs with heparin/heparan sulfate is isoform-specific, The Journal of Biological Chemistry, 272(29):18000-18006 (1997).
McCaffrey, T. et al., Transforming growth factor-β1 is a heparin-binding protein: identification of putative heparin-binding regions and isolation of heparins with varying affinity for TGF-β1, Journal of Cellular Physiology, 152(2):430-440 (1992).
McCaffrey, T.A. et al, Transforming growth factor-β activity is potentiated by heparin via dissociation of the transforming growth factor-β/α$_2$-macroglobulin inactive complex, The Journal of Cell Biology, 109: 441-448 (1989).
Rider, C.C., Heparin/heparan sulphate binding in the TGF-β cytokine superfamily, Biochem. Soc. Trans., 34(Pt3): 458-460 (2006).
Written Opinion of PCT/SG15/50092, 5 pages (dated Jul. 6, 2015).
International Preliminary Report on Patentability for PCT/SG15/50092, 7 pages (dated Nov. 10, 2016).
Bertolino, P. et al., Transforming Growth Factor-bSignal Transduction in Angiogenesis and Vascular Disorders, J. Chest, 128(6): 585S-590S (2005).
Ehrlich, M. et al., Improvement in the appearance of wrinkles with topical transforming growth factor β(1) and I-ascorbic acid, Dermatologic Surgery, 32: 618-625 (2006).

(Continued)

*Primary Examiner* — Leigh C Maier
(74) *Attorney, Agent, or Firm* — Choate, Hall & Stewart LLP; Kristen C. Buteau; Nicholas J. Pace

(57) ABSTRACT

A heparan sulphate that binds TGFβ1 is disclosed.

20 Claims, 30 Drawing Sheets
Specification includes a Sequence Listing.

(56) References Cited

OTHER PUBLICATIONS

Fukazawa, M., A Basic Study on Periodontal Regeneration by Platelet Rich Plasma Invention of the PRP coagulation method by autologous serum, Journal of the Japanese Society of Periodontology, 46(2): 127-136 (2004). English Abstract.

Hong, L. et al., Skull Regeneration Ability of TGF-?1—Containing Absorbable Gelatin Hydrogel, Drug Delivery System, 14(10): 43-50 (1999). English Abstract.

McCaffrey, T.A. et al., Protection of transforming growth factor-beta 1 activity by heparin and fucoidan, Journal of Cellular Physiology, 159: 51-59 (1994).

Solorio, L.D. et al, Chondrogenic differentiation of human mesenchymal stem cell aggregates via controlled release of TGF-$\beta$1 from incorporated polymer microspheres, Journal of Biomedical Materials Research Part A, 1139-1144 (2009).

* cited by examiner

```
         10         20         30         40         50         60
          *          *    *       *                              ^
ALDTNYCFSS TEKNCCVRQL YIDFRKDLGW KWIHEPKGYH ANFCLGPCPY IWSLDTQYSK 70         80         90        100        110
                                  *  *                *
VLALYNQHNP GASAAPCCVP QALEPLPIVY YVGRKPKVEQ LSNMIVRSCK CS
```

Published HBD
*Lysines identified with high confidence
^Lysines identified with medium confidence

```
         10         20         30         40         50         60
ALDTNYCFSS TEKNCCVRQL YIDFRKDLGW KWIHEPKGYH ANFCLGPCPY IWSLDTQYSK
         70         80         90        100        110
VLALYNQHNP GASAAPCCVP QALEPLPIVY YVGRKPKVEQ LSNMIVRSCK CS
```
Peptide used for affinity isolation: RKDLGWKWIHEPKGYH
Figure 6A
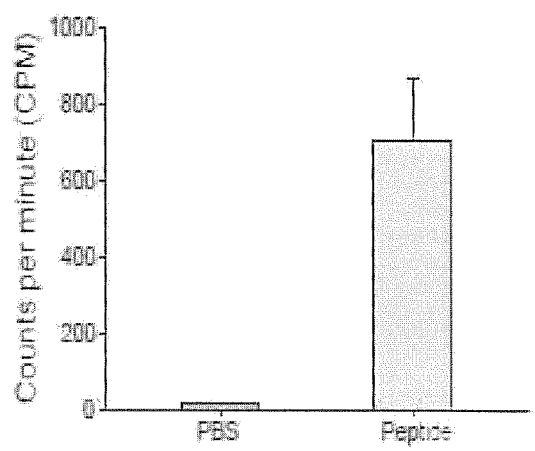
Figure 6B
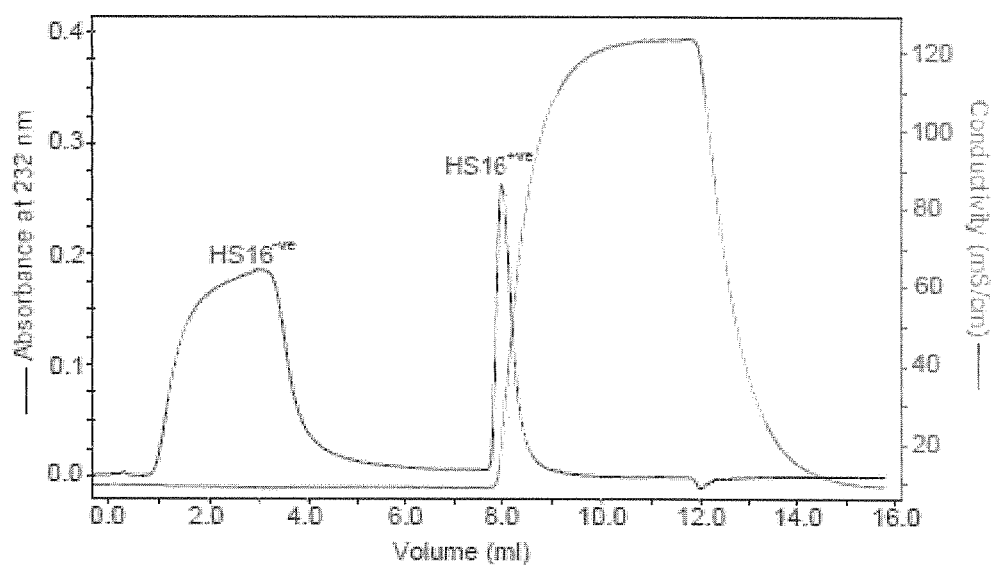
Figure 6C

```
    280        290        300         310    P2  320           330
                                  P1
AL  DTNYCFSSTE KNCCVRQLYI DFRKDLGWKW IHEPKGYHAN FCLGPCPYIW
                                  P4
    340        350        360         370        380           390
SLDTQYSKVL ALYNQHNPGA SAAPCCVPQA LEPLPIVYYV GRKPKVEQLS NMIVRSCKCS
                                          P3
```
Figure 6D
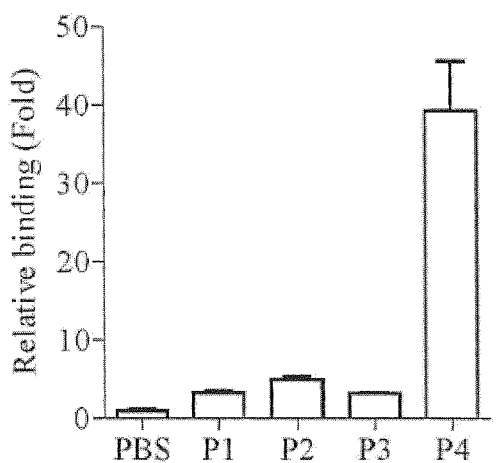
Figure 6E
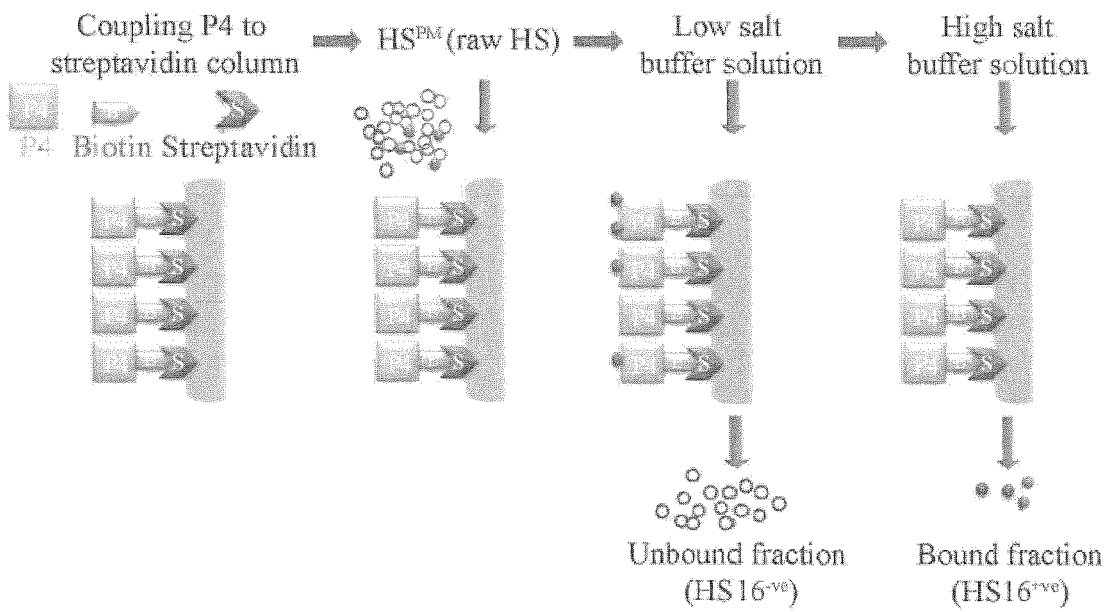
Figure 6F

```
Human TGF-β1    ALDTNYCFSSTEKNCCVRQLYIDFRKDLGWKWIHEPKGYHANFCLGPCPYIWSLDTQYSK
Rabbit TGF-β1   -FSTNYCFSSTEKNCCVRQLYIDFRKDLGWKWIHEPKGYHANFCLGPCPYIWSLDTQYSK
                 :************************************************************
Human TGF-β1    VLALYNQHNPGASAAPCCVPQALEP-LPIVYYVGRKPKVEQLSNMIVRSCKCS
Rabbit TGF-β1   VLALYNQHNPGASAAPCCVPQALEATAHRVTTLGRKPKVE------------
                ************************.    *  :*******
```
Figure 19
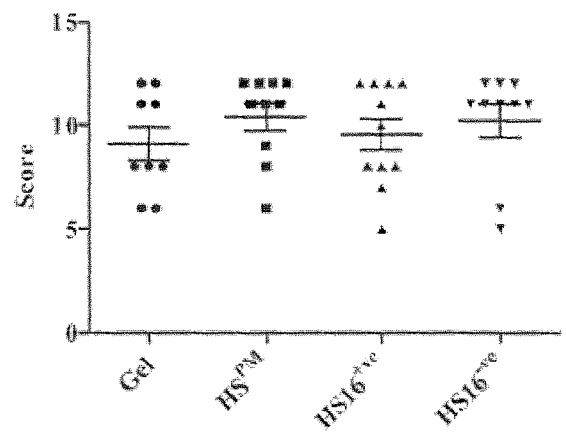
Figure 20A
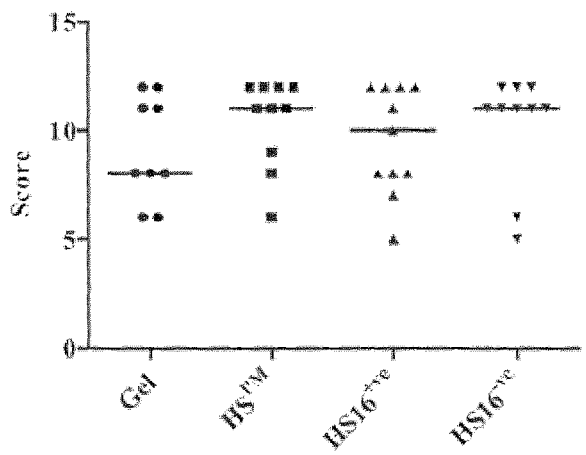
Figure 20B

HEPARAN SULPHATES

FIELD OF THE INVENTION

The present invention relates to heparan sulphates and particularly, although not exclusively, to heparan sulphates that bind TGFβ1.

BACKGROUND TO THE INVENTION

Glycosaminoglycans are complex, linear, highly charged carbohydrates that interact with a wide range of proteins to regulate their function; they are usually synthesized attached to a core protein. GAGs are classified into nonsulfated (HA) and sulfated (CS, DS, KS, heparin and HS).

Among the GAGs, the heparan sulphate (HS) family is of particular interest because of its ability to interact with targeted proteins based on specific sequences within its domains. The family (heparin and HS) consists of repeating uronic acid-(1→4)-D-glucosamine disaccharide subunits with variable patterns of N-, and O-sulfation. For example, the anticoagulant activity of heparin requires 3-O-sulfation of glucosamine residues with a unique pentasaccharide arrangement (Lindahl U, Backstrom G, Hook M, Thunberg L, Fransson L A, Linker A. Structure of the antithrombin-binding site in heparin Proc Natl Acad Sci USA. 1979; 76:3198-202.). A unique sulfation pattern is also apparent for ECM proteins; an avid heparin-binding variant that binds FN is particularly highly charged, with 7 to 8 N-sulfated disaccharides being required, and with a larger domain than usual (>14 residues) (Falcone D J, Salisbury B G J. Fibronectin stimulates macrophage uptake of low-density lipoprotein-heparin-collagen complexes Arteriosclerosis. 1988; 8:263-73; Mahalingam Y, Gallagher J T, Couchman J R. Cellular adhesion responses to the heparin-binding (HepII) domain of fibronectin require heparan sulfate with specific properties. J Biol Chem. 2007; 282:3221-30). However, HS differs from such sulfated heparins by having highly sulfated NS domains separated by unsulfated NA domains; such dispositions provide unique arrangements for selectively binding proteins, without the side effects of heparin (Gandhi N S, Mancera R L. The Structure of Glycosaminoglycans and their Interactions with Proteins. Chem Biol Drug Des. 2008; 72:455-82.).

The disaccharide composition of HS can be elucidated through a series of enzymatic cleavages (Venkataraman G, Shriver Z, Raman R, Sasisekharan R. Sequencing complex polysaccharides. Science. 1999; 286:537-42; Desai U R, Wang H M, Linhardt R J. Specificity studies on the heparin lyases from *Flavobacterium*-heparinum Biochemistry. 1993; 32:8140-5; Shriver Z, Sundaram M, Venkataraman G, Fareed J, Linhardt R, Biemann K, et al. Cleavage of the antithrombin III binding site in heparin by heparinases and its implication in the generation of low molecular weight heparin. Proc Natl Acad Sci USA. 2000; 97:10365-70) using the *Flavobacterium* heparinium enzymes heparinase I, II and III to cleave the glycosidic bonds. More than 90% depolymerization of heparin or HS is possible when all 3 heparinases are used in combination (Karamanos N K, Vanky P, Tzanakakis G N, Tsegenidis T, Hjerpe A. Ion-pair high-performance liquid chromatography for determining disaccharide composition in heparin and heparan sulphate. J Chromatogr A. 1997; 765:169-79; Vynios D H, Karamanos N K, Tsiganos C P. Advances in analysis of glycosaminoglycans: its application for the assessment of physiological and pathological states of connective tissues, J Chromatogr B. 2002; 781:21-38.). The resulting disaccharide mixtures can be analyzed by PAGE (Hampson I N, Gallagher J T. Separation of radiolabeled glycosaminoglycan oligosaccharides by polyacrylamide-gel electrophoresis Biochem J. 1984; 221:697-705), SAX-HPLC (Skidmore M A A, Yates E and Turnbull J E. Labelling heparan sulfate saccharides with chromophore, fluorescence and mass tag for HPLC and MS separations. Methods in Molecular biology. 2009; 534:157-69), or highly sensitive capillary electrophoresis (CE) (Lamari F, Militsopoulou M, Gioldassi X, Karamanos N K. Capillary electrophoresis: a superior miniaturized tool for analysis of the mono-, di-, and oligosaccharide constituents of glycan moieties in proteoglycans. Fresenius J Anal Chem. 2001; 371:157-67; Karamanos N K, Vanky P, Tzanakakis G N, Hjerpe A. High performance capillary electrophoresis method to characterize heparin and heparan sulfate disaccharides. Electrophoresis. 1996; 17:391-5; Sudhalter J, Folkman J, Svahn C M, Bergendal K, Damore P A. Importance of size, sulfation, and anticoagulant activity in the potentiation of acidic fibroblast growth-factor by heparin J Biol Chem. 1989; 264:6892-7; Militsopoulou M, Lamari F N, Hjerpe A, Karamanos N K. Determination of twelve heparin- and heparan sulfate-derived disaccharides as 2-aminoacridone derivatives by capillary zone electrophoresis using ultraviolet and laser-induced fluorescence detection. Electrophoresis. 2002; 23:1104-9) by comparison to known disaccharide standards.

SUMMARY OF THE INVENTION

The present invention concerns a heparan sulphate species and heparan sulphate preparations comprising or consisting of the heparan sulphate species. The heparan sulphate species is called HS16. HS16 refers to a novel class of structurally and functionally related isolated heparan sulphate.

HS16 has been found to bind TGFβ1, enhance the thermal stability of TGFβ1 and potentiate TGFβ1 signaling and thus the chondrogenic differentiation of mesenchymal stem cells.

In one aspect of the present invention a heparan sulphate HS16 is provided. HS16 may be provided in isolated form or in substantially purified form. This may comprise providing a composition in which the heparan sulphate component is at least 80% HS16, more preferably one of at least 85%, 90%, 95%, 96%, 97%, 98%, 99% or 100%.

In preferred embodiments, HS16 is capable of binding a peptide or a polypeptide having the amino acid sequence of RKDLGWKWIHEPKGYH (SEQ ID NO: 1). The peptide may have one or more additional amino acids at one or both ends of this sequence. For example, the peptide may have any of 1, 2, 3, 4, 5, 6, 7, 8, 9, 10, 11, 12, 13, 14, 15, 16, 17, 18, 19, 20 or more amino acids at one or both end of this sequence.

In other embodiments the polypeptide is a TGFβ1 protein. In some embodiments HS16 binds to a peptide having or consisting of the amino acid sequence of SEQ ID NO:1 or a TGFβ1 protein with a $K_D$ of less than 100 μM, more preferably less than one of 50 μM, 40 μM, 30 μM, 20 μM, 10 μM, 1 μM, 500 nM, 100 nM, 50 nM, 10 nM or 1 nM.

HS16 may be obtained, identified, isolated or enriched according to the inventors' methodology described herein, which may comprise the following steps:
  (i) providing a solid support having polypeptide molecules adhered to the support, wherein the polypeptide comprises a heparin-binding domain having the amino acid sequence of RKDLGWKWIHEPKGYH;
  (ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

Optionally, the method may further comprise a size fractionation step, e.g. after step (iv) or (v). Size fractionation may be used to remove heparan sulphate chains smaller than a selected threshold, e.g. one of dp4, dp6, dp8, dp10, dp12, dp14, dp16, dp18, dp20, dp22, or dp24.

In the inventors' methodology the mixture may comprise glycosaminoglycans obtained from commercially available sources. One suitable source is a heparan sulphate fraction, e.g. a commercially available heparan sulphate. One suitable heparan sulphate fraction can be obtained during isolation of heparin from porcine intestinal mucosa, another is heparan sulphate from porcine mucosa [$HS^{PM}$] (e.g. from Celsus Laboratories Inc. —sometimes called "Celsus HS").

Other suitable sources of heparan sulphate include heparan sulphate from any mammal (human or non-human), particularly from the kidney, lung or intestinal mucosa. In some embodiments the heparan sulphate is from pig (porcine) or cow (bovine) intestinal mucosa, kidney or lung.

In another aspect of the present invention a composition comprising HS16 according to any one of the aspects above and TGFβ1 protein is provided.

In one aspect of the present invention a pharmaceutical composition or medicament is provided comprising HS16 in accordance with the aspects described above. The pharmaceutical composition or medicament may further comprise a pharmaceutically acceptable carrier, adjuvant or diluent.

In some embodiments the pharmaceutical composition is for use in a method of treatment, the method comprising the repair and/or regeneration of tissue, e.g. connective tissue (cartilage, bone, tendon, ligament, skin, cornea) or a broken bone. In some embodiments the pharmaceutical composition or medicament may further comprise TGFβ1 protein. In some embodiments the pharmaceutical composition or medicament may further comprise mesenchymal stem cells.

In another aspect of the present invention HS16 is provided for use in a method of medical treatment. The method of medical treatment may comprise a method of wound healing in vivo, the repair and/or regeneration of tissue, e.g. the repair and/or regeneration of connective tissue (cartilage, bone, tendon, ligament, skin, cornea). Such repair and/or regeneration of may be in a mammal or a human.

In a related aspect of the present invention the use of HS16 in the manufacture of a medicament for use in a method of medical treatment is provided. In some embodiments the method of medical treatment comprises the repair and/or regeneration of tissue as described above.

In a further aspect of the present invention a biocompatible implant or prosthesis comprising a biomaterial and HS16 is provided. In some embodiments the implant or prosthesis is coated with HS16. In some embodiments the implant or prosthesis is impregnated with HS16. The implant or prosthesis may be further coated or impregnated with TGFβ1 protein and/or with mesenchymal stem cells.

In another aspect of the present invention a method of forming a biocompatible implant or prosthesis is provided, the method comprising the step of coating or impregnating a biomaterial with HS16. In some embodiments the method further comprises coating or impregnating the biomaterial with one or both of TGFβ1 protein and mesenchymal stem cells.

In some aspects a method may comprise administering HS16 and mesenchymal stem cells to a patient. In such methods at least two of HS16, TGFβ1 protein and mesenchymal stem cells may be formulated in a pharmaceutical composition comprising at least two of the HS16, TGFβ1 protein and mesenchymal stem cells and a pharmaceutically acceptable carrier, adjuvant or diluent.

Preferably, the HS16, TGFβ1 protein and mesenchymal stem cells are respectively provided in therapeutically effective amounts. In some embodiments the method further comprises the step of formulating therapeutically effective amounts of HS16, and/or TGFβ1 protein and/or mesenchymal stem cells as a pharmaceutical composition comprising the HS16, and/or TGFβ1 protein and/or mesenchymal stem cells and a pharmaceutically acceptable carrier, adjuvant or diluent, wherein the pharmaceutical composition is administered to the patient.

In another aspect of the present invention a method of treating a patient is provided, the method comprising surgically implanting a biocompatible implant or prosthesis, which implant or prosthesis comprises a biomaterial and HS16, into tissue of the patient at or surrounding the site of fracture.

In some embodiments the implant or prosthesis is coated with HS16. In some embodiments the implant or prosthesis is impregnated with HS16. In some embodiments the implant or prosthesis is further impregnated with one or both of TGFβ1 protein and mesenchymal stem cells.

In a further aspect of the present invention culture media is provided, the culture media comprising HS16.

In another aspect of the present invention the use of HS16 in cell culture in vitro is provided. In a related aspect of the present invention the use of HS16 in the growth of connective tissue in vitro is provided. In another related aspect of the present invention a method for growing connective tissue in vitro is provided, the method comprising culturing mesenchymal stem cells in contact with exogenously added HS16.

In yet a further aspect of the present invention a method for the repair, replacement or regeneration of tissue, e.g. connective tissue, in a human or animal patient in need of such treatment is provided, the method comprising:
(i) culturing mesenchymal stem cells in vitro in contact with HS16 for a period of time sufficient for said cells to form tissue;
(ii) collecting said tissue;
(iii) implanting said tissue into the body of the patient at a site of injury or disease to repair, replace or regenerate tissue in the patient.

The tissue may be connective tissue, e.g. bone, cartilage, tendon, skin or fat. In some embodiments the method further comprises contacting the mesenchymal stem cells in culture with exogenous TGFβ1 protein.

In another aspect of the present invention tissue obtained by in vitro culture of mesenchymal stem cells in the presence of HS16 is provided. In some embodiments the tissue is obtained by in vitro culture of mesenchymal stem cells in the presence of HS16 and TGFβ1 protein.

In a further aspect of the present invention a method of culturing stem cells, e.g. mesenchymal stem cells is provided, the method comprising culturing stem cells in contact with HS16.

In some aspects of the present invention a method of culturing stem cells in vitro is provided, the method comprising culturing stem cells in vitro in contact with heparan sulphate HS16. The HS16 is preferably exogenous and isolated, and added to the culture as a supplement, e.g. as part of the culture media.

In yet a further aspect of the present invention a kit of parts is provided, the kit comprising a predetermined amount of HS16 and a predetermined amount of TGFβ1. The kit may comprise a first container containing the predetermined amount of HS16 and a second container containing the predetermined amount of TGFβ1. The kit may further comprise a predetermined amount of mesenchymal stem cells. The kit may be provided for use in a method of medical treatment. The method of medical treatment may comprise a method of wound healing in vivo, the repair and/or regeneration of tissue, such as connective tissue (e.g. cartilage, bone, tendon, ligament, skin, cornea). The repair and/or regeneration may be in a mammal or a human. The kit may be provided together with instructions for the administration of the HS16, TGFβ1 protein and/or mesenchymal stem cells separately, sequentially or simultaneously in order to provide the medical treatment.

In a further aspect of the present invention products are provided, the products containing therapeutically effective amounts of:
(i) HS16; and one or both of
(ii) TGFβ1 protein;
(iii) Mesenchymal stem cells,
for simultaneous, separate or sequential use in a method of medical treatment. The method of medical treatment may comprise a method of wound healing in vivo, the repair and/or regeneration of connective tissue. The repair and/or regeneration may be in a mammal or a human. The products may optionally be formulated as a combined preparation for co-administration.

As shown herein, HS16 has the property of stabilising TGFβ1, and thereby prolonging its action. HS16 prevents TGFβ1 from degradation in culture medium. This can be usefully applied to the storage of TGFβ1 preparations and the preparation of TGFβ1 containing culture media.

As such, in one aspect of the present invention a composition comprising a growth factor and isolated HS16 is provided. The growth factor may be a protein growth factor, and is preferably TGFβ1. The composition may comprise isolated TGFβ1 and isolated HS16. In some embodiments the composition may be a culture media. In other embodiments the composition may be a pharmaceutical composition or medicament containing TGFβ1.

The composition may be an TGFβ1 preparation comprising TGFβ1 and isolated HS16 in a container. A suitable container may be a bottle, vial, tube or syringe.

A method of increasing the stability of a growth factor is also provided, the method comprising contacting a growth factor with isolated HS16.

The stability of the growth factor may be measured in terms of its half-life, i.e. the amount of time taken for half of the growth factor in a given composition to be degraded and/or lose its activity. The growth factor is preferably a protein growth factor, more preferably TGFβ1. HS16 acts to maintain and prolong TGFβ1 half-life. The method may involve contacting isolated HS16 with the growth factor (e.g. TGFβ1) in vitro, e.g. as part of preparation of a growth factor (e.g. TGFβ1) composition, its storage or transport. Alternatively, the method may involve contacting isolated HS16 with the growth factor (e.g. TGFβ1) in vivo, e.g. by administering isolated HS16 to tissue in which the growth factor (e.g. TGFβ1) [naturally occurring in the tissue or exogenously added to the tissue] is present. The method may also comprise the step of adding exogenous growth factor (e.g. TGFβ1) to the tissue.

The stability of TGFβ1 in a given composition or tissue that contains isolated HS16 (or to which isolated HS16 has been added) may be compared against a comparable composition not containing HS16 (or to which isolated HS16 has not been added. In the composition and method described above the HS16 may be purified, as described herein. The TGFβ1 may be isolated and/or purified, non-isolated or partially isolated, e.g. part of an extracellular matrix material, or present in a composition of cells. Isolated or purified TGFβ1 may be recombinant TGFβ1. Recombinant TGFB1 is commercially available from a number of commercial manufacturers.

In some aspects HS16 is used as a preserving agent and/or preservative during the production of blood-derived products. In some embodiments the blood-derived products include platelets, platelet products, platelet lysates and platelet-rich plasma (PRP). The blood-derived products may be isolated from blood or serum, and optionally enriched or partitioned from other components of blood and/or serum.

In some aspects a preparation of blood derived product(s) is provided, the preparation comprising a blood derived product and a predetermined quantity of HS16. The HS16 is preferably in isolated or purified form and is preferably exogenous to the blood derived product(s), being added to the blood derived product(s). The preparation may be a platelet preparation, e.g. platelets, platelet products, platelet lysates or platelet-rich plasma (PRP), to which HS16 has been added.

In accordance with the above, a method of preserving biological material is provided, preferably biological material comprising TGFβ1, the method comprising contacting the biological material with a predetermined quantity of HS16. In some embodiments the biological material may be selected from cellular material, tissue, blood-derived products, cells, or stem cells.

In another aspect of the present invention HS16 is provided for use during isolation and/or processing of stem cells. In some embodiments, HS16 is provided as a reagent for use during culture and/or expansion of stem cells. Accordingly, a method of isolating, processing, culturing or expanding stem cells may be provided, the method comprising contacting the stem cells with a predetermined quantity of HS16. The stem cells may optionally express TGFβ1.

Optionally, aspects and embodiments of the present do not include an HS as described in Manton et al (Journal of Cellular Physiology 209:219-229 (2006)).

DESCRIPTION

The inventors have used a sequence-based affinity chromatography platform to exploit the heparin-binding domain of TGFB1. This allowed the enrichment of a TGFB1-binding heparan sulphate (HS) fraction.

The terms "sulphate", "sulphated", and "sulphation" are used interchangeably with "sulfate", "sulfated" and "sulfation" respectively.

HS16

The present invention relates to a class of heparan sulphate molecule called HS16. HS16 molecules are obtainable by methods of enriching mixtures of compounds containing one or more glycosaminoglycans (GAGs) that bind to a polypeptide corresponding to a heparin-binding domain of TGFβ1. In particular, HS16 molecules can be obtained by enriching for heparan sulphate that binds to a heparan binding domain of TGFβ1 which domain comprises, or consists of, the amino acid sequence RKDLGWKWIHEP-KGYH. The enrichment process may be used to isolate HS16.

The present invention also relates to mixtures of compounds enriched with HS16, and methods of using such mixtures.

In addition to being obtainable by the methodology described here, HS16 can also be defined functionally and structurally.

Functionally, an HS16 is capable of binding a peptide having, or consisting of, the amino acid sequence RKDLGWKWIHEPKGYH (SEQ ID NO:1). The peptide may contain one or more additional amino acids on one or both ends of the peptide, or in some instances may be attached to a short amino acid linker sequence (e.g. about 1 to 5 amino acids in length) and/or a tag such as biotin.

Preferably, HS16 binds the peptide with a $K_D$ of less than 100 µM, more preferably less than one of 50 µM, 40 µM, 30 µM, 20 µM, 10 µM, 1 µM, 500 nM, 100 nM, 50 nM, 10 nM, 1 nM, or 100 pM.

Preferably, HS16 also binds TGFβ1 protein with a $K_D$ of less than 100 µM, more preferably less than one of 50 µM, 40 µM, 30 µM, 20 µM, 10 µM, 1 µM, 500 nM, 100 nM, 50 nM, 10 nM, mM, or 100 pM.

Binding between HS16 and TGFβ1 protein may be determined by the following assay method.

GAGs are immobilized in each well and then challenged with TGF-β1 according to the manufacturer's instructions. Briefly, triplicate wells are first pre-coated with 5 µg/ml of heparin, $HS^{PM}$, $HS16^{+ve}$ or $HS16^{-ve}$ in standard assay buffer (SAB: 100 mM NaCl, 50 mM sodium acetate, 0.2% v/v Tween 20, pH 7.2), and then incubated overnight at room temperature. The plates are next washed carefully three times with SAB, blocked with 250 µl of blocking solution (0.4% w/v fish skin gelatine, Sigma-Aldrich, in SAB) and incubated for 1 h at 37° C. TGF-β1 was then dissolved in blocking solution at a concentration of 100, 200, or 400 ng/ml. The plates are washed three times with SAB and each dilution of protein (200 µl) is dispensed into triplicate wells and incubated for 2 h at 37° C., rinsed with SAB and 200 µl of 750 ng/ml monoclonal mouse anti-TGF-β1 antibody (MAB2401, R&D Systems) added in blocking solution. Plates are then incubated for 1 h at 37° C., washed with SAB, and 200 µl of 1 µg/ml polyclonal goat anti-mouse biotinylated antibody (ab6788, Abcam) added in blocking solution. Again, plates are incubated for 1 h at 37° C., washed with SAB, and 200 µl of 220 ng/ml ExtrAvidin AP (Sigma-Aldrich) is added in blocking solution, incubated for 30 min at 37° C., and then rinsed with SAB. Finally, 200 µl of development reagent (SigmaFAST p-Nitrophenyl phosphate, Sigma-Aldrich) is added, incubated at 37° C. for 40 min and read at 405 nm within 1 h.

In this assay, binding may be determined by measuring absorbance and may be determined relative to controls such as TGFβ1 protein in the absence of added heparan sulphate, or TGFβ1 protein to which an heparan sulphate is added that does not bind TGFβ1 protein.

The unique interaction of HS16 with TGFβ1 can be analysed by surface plasmon resonance (see experimental results), e.g. in competition assay with heparin, $HS^{PM}$, $HS16^{+ve}$ or $HS16^{-ve}$.

The binding of HS16 is preferably specific, in contrast to non-specific binding and in the context that the HS16 can be selected from other heparan sulphates and/or GAGs by a method involving selection of heparan sulphates exhibiting a high affinity binding interaction with the peptide comprising RKDLGWKWIHEPKGYH such as SEQ ID NO:1, or with TGFβ1 protein.

HS16 according to the present invention preferably enhances the thermal stability of TGFβ1 and potentiates TGFβ1 signaling and chondrogenic differentiation of mesenchymal stem cells. HS16 finds use in any application wherein stabilisation of TGFβ1 and/or prevention of degradation of TGFβ1 and/or prolonging of TGFβ1 is desirable. For example, HS16 finds use to stabilise TGFβ1 in platelet products.

The disaccharide composition of HS16 following digestion with heparin lyases I, II and III to completion and then subjecting the resulting disaccharide fragments to HPLC analysis is shown below.

| Disaccharide | Normalised weight percentage |
| --- | --- |
| ΔUA,2S-GlcNS,6S | 14.75 |
| ΔUA,2S-GlcNS | 4.58 |
| ΔUA-GlcNS,6S | 12.98 |
| ΔUA,2SGlcNAc,6S | 0.0 |
| ΔUA-GlcNS | 22.24 |
| ΔUA,2S-GlcNAc | 0.56 |
| ΔUA-GlcNAc,6S | 12.63 |
| ΔUA-GlcNAc | 32.26 |

HS16 according to the present invention includes heparan sulphate that has a disaccharide composition within ±10% (more preferably ±one of 9%, 8%, 7%, 6%, 5%, 4%, 3%, 2%, 1% or 0.5%) of the normalised percentage values shown for each disaccharide above for the HS16 retained species (HS16+) as determined by digestion with heparin lyases I, II and III to completion and then subjecting the resulting disaccharide fragments to HPLC analysis.

The disaccharide composition of HS16 as determined by digestion with heparin lyases I, II and III to completion and then subjecting the resulting disaccharide fragments to HPLC analysis may have a disaccharide composition according to any one of the following:

| Disaccharide | Normalised weight percentage |
| --- | --- |
| ΔUA,2S-GlcNS,6S | 14.75 ± 3.0 |
| ΔUA,2S-GlcNS | 4.58 ± 2.0 |
| ΔUA-GlcNS,6S | 12.98 ± 3.0 |
| ΔUA,2S-GlcNAc,6S | 0.0 ± 2.0 |
| ΔUA-GlcNS | 22.24 ± 3.0 |
| ΔUA,2S-GlcNAc | 0.56 ± 0.5 |
| ΔUA-GlcNAc,6S | 12.63 ± 3.0 |
| ΔUA-GlcNAc | 32.26 ± 3.0 |
| or | |
| ΔUA,2S-GlcNS,6S | 14.75 ± 2.0 |
| ΔUA,2S-GlcNS | 4.58 ± 2.0 |
| ΔUA-GlcNS,6S | 12.98 ± 2.0 |
| ΔUA,2S-GlcNAc,6S | 0.0 ± 2.0 |
| ΔUA-GlcNS | 22.24 ± 2.0 |
| ΔUA,2S-GlcNAc | 0.56 ± 0.5 |
| ΔUA-GlcNAc,6S | 12.63 ± 2.0 |
| ΔUA-GlcNAc | 32.26 ± 2.0 |
| or | |
| ΔUA,2S-GlcNS,6S | 14.75 ± 2.0 |
| ΔUA,2S-GlcNS | 4.58 ± 1.0 |
| ΔUA-GlcNS,6S | 12.98 ± 2.0 |
| ΔUA,2S-GlcNAc,6S | 0.0 ± 1.0 |
| ΔUA-GlcNS | 22.24 ± 2.0 |
| ΔUA,2S-GlcNAc | 0.56 ± 0.5 |
| ΔUA-GlcNAc,6S | 12.63 ± 2.0 |
| ΔUA-GlcNAc | 32.26 ± 3.0 |
| or | |
| ΔUA,2S-GlcNS,6S | 14.75 ± 1.0 |
| ΔUA,2S-GlcNS | 4.58 ± 0.4 |
| ΔUA-GlcNS,6S | 12.98 ± 1.0 |
| ΔUA,2S-GlcNAc,6S | 0.0 ± 0.6 |
| ΔUA-GlcNS | 22.24 ± 3.0 |
| ΔUA,2S-GlcNAc | 0.56 ± 0.4 |
| ΔUA-GlcNAc,6S | 12.63 ± 1.0 |
| ΔUA-GlcNAc | 32.26 ± 1.6 |

-continued

| Disaccharide | Normalised weight percentage |
|---|---|
| or | |
| ΔUA,2S-GlcNS,6S | 14.75 ± 0.75 |
| ΔUA,2S-GlcNS | 4.58 ± 0.3 |
| ΔUA-GlcNS,6S | 12.98 ± 0.75 |
| ΔUA,2S-GlcNAc,6S | 0.0 ± 0.45 |
| ΔUA-GlcNS | 22.24 ± 2.25 |
| ΔUA,2S-GlcNAc | 0.56 ± 0.3 |
| ΔUA-GlcNAc,6S | 12.63 ± 0.75 |
| ΔUA-GlcNAc | 32.26 ± 1.2 |
| or | |
| ΔUA,2S-GlcNS,6S | 14.75 ± 0.5 |
| ΔUA,2S-GlcNS | 4.58 ± 0.2 |
| ΔUA-GlcNS,6S | 12.98 ± 0.5 |
| ΔUA,2SGlcNAc,6S | 0.0 ± 0.3 |
| ΔUA-GlcNS | 22.24 ± 1.5 |
| ΔUA,2S-GlcNAc | 0.56 ± 0.2 |
| ΔUA-GlcNAc,6S | 12.63 ± 0.5 |
| ΔUA-GlcNAc | 32.26 ± 0.8 |

In preferred embodiments the total weight percentage of the 8 disaccharides listed is 100% (optionally ±3.0% or less, or ±2.0% or less, ±1.0% or less, ±0.5% or less).

In some embodiments, the normalised weight percentage of ΔUA,2SGlcNAc,6S is different than in the above profiles. For example, HS16 may have the disaccharides at normalised weight percentages as described in above, except for ΔUA,2SGlcNAc,6S, which may be present at a different normalised weight percentage, or may be absent.

In some embodiments, HS16 is defined by reference to the above normalised weight percentages for ΔUA,2S-GlcNS, 6S, ΔUA,2S-GlcNS, ΔUA-GlcNS,6S, ΔUA-GlcNS, ΔUA, 2S-GlcNAc, ΔUA-GlcNAc,6S and ΔUA-GlcNAc.

Digestion of HS preparations with heparin lyase enzymes may be conducted as follows: HS preparations (1 mg) are each dissolved in 500 µL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 µL water and an aliquot (50 µL) is taken for analysis.

Specifically, HS16 could be digested as follows: $HS^{PM}$, $HS16^{+ve}$ and $HS16^{-ve}$ samples are solubilized in water (1100 µl) and filtered (Minisart RC15, 0.2 µm syringe filter unit, Sartorius Stedim, #17761) to remove any particulate matter. As a further clean-up step, the filtered solution is passed through a 2000 MWCO membrane (Vivaspin 2, Hydrosart, Sartorius Stedim, #VS02H91, 2000 MWCO HY membrane, 2 mL ultrafiltration spin column) by centrifugation (4000 rpm, 1 h, 15° C.). The retentate is washed with water (3×1 ml), recovered from the filter and lyophilized. The purified HS samples are solubilized in water (1 mg/ml) and aliquots (2×~1 ml) of each freeze-dried sample were taken for analysis. The HS samples are digested to di- and oligosaccharides by the sequential addition of heparin lyase enzymes (Heparin lyase I, II and III, Ibex Technologies) based on the method of Brickman et al. (Brickman, Y. G., Ford, M. D., Gallagher, J. T., Nurcombe, V., Bartlett, P. F., and Turnbull, J. E. (1998) *J Biol Chem* 273, 4350-4359), but with some modifications. The dry HS samples are re-solubilized in digestion buffer (500 µl; 50 mM sodium phosphate buffer, pH 7.0) and heparin lyase I (5 µl; 5 mIU) is added to each sample. The samples are incubated (37° C., 2 h) With gentle mixing on a rotating wheel (9 rpm). Heparin lyase III (5 µl; 5 mIU) is added to the digests and incubated for a further 1 h (as above). Heparin lyase II(5 µl; 5 mIU) is added and the digests are incubated as above, for 18 h. Finally, aliquots (5 µl; 5 mIU) of all three heparin lyases are added simultaneously and the digests are incubated for a further 24 h. The enzyme digestion is terminated by heating (100° C., 5 min). All three HS samples are digested in duplicate.

In some embodiments an HS16 chain comprises about 12 to 26 saccharide units (degree of polymerization, dp). In some embodiments the dp number may be one of at least 12, at least 14, at least 16, at least 18, at least 20, at least 22, at least 24, or at least 26. Optionally, it may be less than 26.

A composition of HS16 chains having a desired range of size (in dp) can be prepared by applying a size fractionation procedure to HS16.

To identify HS16 the inventors used a method that involves enriching for glycosaminoglycan molecules that exhibit binding to particular polypeptides having a heparin-binding domain. Isolated GAG mixtures and/or molecules can then be identified and tested for their ability to modulate the growth and differentiation of cells and tissue expressing a protein containing the heparin-binding domain. This enables the controlled analysis of the effect of particular GAG saccharide sequences on the growth and differentiation of cells and tissue, both in vitro and in vivo. This methodology is described in PCT/GB2009/000469 (WO2010/030244), incorporated herein by reference. The inventors applied this methodology to TGFβ1 in order to isolate and characterise GAGs having high binding to TGFβ1.

Accordingly, to identify HS16 the inventors provided a method of isolating glycosaminoglycans capable of binding to proteins having heparin/heparan-binding domains, the method comprising:
 (i) providing a solid support having polypeptide molecules adhered to the support, wherein the polypeptide comprises a heparin-binding domain;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans.

The inventors also provided isolated glycosaminoglycans identified by their ability to modulate the growth or differentiation of cells or tissues. To do this, they provided a method of identifying glycosaminoglycans capable of stimulating or inhibiting the growth and/or differentiation of cells and/or tissues, the method comprising:
 (i) providing a solid support having polypeptide molecules adhered to the support, wherein the polypeptide comprises a heparin-binding domain;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans;
 (vi) adding the collected glycosaminoglycans to cells or tissues in which a protein containing the amino acid sequence of the heparin-binding domain is present;

(vii) measuring one or more of: proliferation of the cells, differentiation of the cells, expression of one or more protein markers.

The inventors used these methods to identify a GAG capable of binding to TGFB1 (which they called HS16), wherein the polypeptide used in the inventors' methodology comprised the heparin-binding domain of RKDLGWKWI-HEPKGYH (SEQ ID NO:1).

In the inventors' methodology, the mixture comprising GAGs may contain synthetic glycosaminoglycans. However, GAGs obtained from cells or tissues are preferred. The mixture comprising GAGs is preferably a heparan sulphate preparation such as $HS^{PM}$. In preferred embodiments the GAG is heparan sulphate.

The heparan sulphate or GAG component may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong anion exchange high performance liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulfation of the GAG can also be determined and used to determine GAG structure. For example, for heparan sulphate the pattern of sulfation at amino sugars and at the C2, C3 and C6 positions may be used to characterise the heparan sulphate.

Disaccharide analysis, tetrasaccharide analysis and analysis of sulfation can be used in conjunction with other analytical techniques such as HPLC, mass spectrometry and NMR which can each provide unique spectra for the GAG. In combination, these techniques may provide a definitive structural characterisation of the GAG.

For example, the $^1H$ NMR spectra of HS16, in comparison with a gross HS preparation such as $HS^{PM}$ (from which HS16 may have been derived) and HS16 is shown in FIG. 7. HS16 according to the present invention may have a $^1H$ NMR spectra corresponding to the HS16 spectra of FIG. 7.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide (e.g. HS-polypeptide) complexes may be subjected to treatment with an agent that lyses glycosaminoglycan chains, e.g. a lyase. Lyase treatment may cleave portions of the bound GAG that are not taking part in the binding interaction with the polypeptide. Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulfation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased. GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

HS16 preferably exhibits a functional effect when contacted with cells or tissue in which a protein containing the heparin-binding domain is expressed or contained. The functional effect may be a modulating or potentiating effect.

The functional effect may be to promote (stimulate) the proliferation of the cells of a certain type or the differentiation of one cell type into another, or the expression of one or more protein markers. For example, HS16 may promote differentiation of stem cells into specialised cell types (e.g. mesenchymal stem cells into connective tissue).

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes, or consists of, the heparin-binding domain and optionally including one or more amino acids at one or each of the N- and C-terminals of the peptides. These additional amino acids may enable the addition of linker or attachment molecules (e.g. a tag such as biotin) to the polypeptide that are required to attach the polypeptide to the solid support.

In preferred embodiments of the inventors' methodology, in addition to the number of amino acids in the heparin-binding domain the polypeptide contains no more than 1-20, more preferably 1-10, still more preferably 1-5 additional amino acids, e.g. any of 1, 2, 3, 4, 5, 6, 7, 8, 9, 10, 11, 12, 13, 14, 15, 16, 17, 18, 19 or 20 amino acids at one or both of the C- and/or N-terminals of the polypeptide. In some embodiments the amino acid sequence of the heparin-binding domain accounts for at least 80% of the amino acids of the polypeptide, more preferably one of at least 90%, 91%, 92%, 93%, 94%, 95%, 96%, 97%, 98%, 99% or 100%. In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is TGFβ1. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

In this specification the protein is TGFB1. The amino acid sequences of the preferred heparin-binding domain is RKDLGWKWIHEPKGYH (SEQ ID NO:1).

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities. Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a high-affinity manner to the polypeptide; those that bind in a low-affinity manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected. GAGs may accordingly be obtained that have a high binding affinity for a protein of interest and/or the heparin-binding domain of the protein of interest. The binding affinity ($K_d$) may be chosen from one of: less than 10 µM, less than 1 µM, less than 100 nM, less than 10 nM, less than 1 nM, less than 100 pM.

HS16 obtained by the methods described may be useful in a range of applications, in vitro and/or in vivo. HS16 may be provided for use in stimulation or inhibition of cell or tissue growth and/or proliferation and/or differentiation either in cell or tissue culture in vitro, or in cells or tissue in vivo.

HS16 may be provided as a formulation for such purposes. For example, culture media may be provided comprising HS16.

Cells or tissues obtained from in vitro cell or tissue culture in the presence of HS16 may be collected and implanted into a human or animal patient in need of treatment. A method of implantation of cells and/or tissues may therefore be provided, the method comprising the steps of:

(a) culturing cells and/or tissues in vitro in contact with HS16;
(b) collecting the cells and/or tissues;
(c) implanting the cells and/or tissues into a human or animal subject in need of treatment.

The cells may be cultured in part (a) in contact with HS16 for a period of time sufficient to allow growth, proliferation or differentiation of the cells or tissues. For example, the period of time may be chosen from: at least 5 days, at least 10 days, at least 20 days, at least 30 days or at least 40 days.

In another embodiment the HS16 may be formulated for use in a method of medical treatment, including the prevention or treatment of injury or disease. A pharmaceutical composition or medicament may be provided comprising HS16 and a pharmaceutically acceptable diluent, carrier or adjuvant. Such pharmaceutical compositions or medicaments may be provided for the prevention or treatment of injury or disease. The use of HS16 in the manufacture of a medicament for the prevention or treatment of injury or disease is also provided. Optionally, pharmaceutical compositions and medicaments according to the present invention may also contain the protein of interest (i.e. TGFβ1) having the heparin-binding domain to which the GAG binds. In further embodiments the pharmaceutical compositions and medicaments may further comprise stem cells, e.g. mesenchymal stem cells.

Prevention or treatment of injury or disease may comprise the strengthening, repair, regeneration or replacement of cells or tissue, such as connective tissue (e.g. bone, cartilage, muscle, fat, tendon, ligament), including skin. For the repair of tissue, the pharmaceutical composition or medicament comprising HS16 may be administered directly to the site of injury or disease in order to stimulate the growth, proliferation and/or differentiation of new tissue to effect a repair of the injury or to cure or alleviate (e.g. provide relief to the symptoms of) the disease condition. The repair or regeneration of the tissue may be improved by combining stem cells in the pharmaceutical composition or medicament.

Some uses may involve application of HS16 to the skin as part of the repair or rejuvenation of skin. This may be a therapeutic and/or cosmetic application, involving repair and/or rejuvenation of the skin barrier, and/or improvement of appearance of the skin. For example, HS16 may be applied to the skin in order to repair, rejuvenate and/or improve the appearance of burns or other scarring.

For the replacement of tissue, HS16 may be contacted with cells and/or tissue during in vitro culture of the cells and/or tissue in order to generate cells and/or tissue for implantation at the site of injury or disease in the patient. Implantation of cells or tissue can be used to effect a repair of the injured or diseased tissue in the patient by replacement of the injured or diseased tissue. This may involve excision of injured/diseased tissue and implantation of new tissue prepared by culture of cells and/or tissue in contact with HS16.

Pharmaceutical and cosmetic compositions and medicaments according to the present invention may therefore comprise one of:

(a) HS16;
(b) HS16 in combination with stem cells;
(c) HS16 in combination with a protein containing the heparin-binding domain bound by HS16 (e.g. RKDLGWKWIHEPKGYH);
(d) HS16 in combination with stem cells and a protein containing the heparin-binding domain bound by HS16 (e.g. RKDLGWKWIHEPKGYH);
(e) Tissues or cells obtained from culture of cells or tissues in contact with HS16.

HS16 may be used in the repair or regeneration of bodily tissue, especially connective tissue. Accordingly, HS16 may be used to prevent or treat a wide range of diseases and injuries in/to connective tissue.

The use of HS16 in the repair, regeneration or replacement of tissue may involve use in wound healing, e.g. acceleration of wound healing, healing of scar or bone tissue and tissue grafting.

In some aspects the invention relates to a cosmetic treatment comprising the administration of HS16. "Cosmetic" as used herein is non-therapeutic. The cosmetic treatment may be used to improve the appearance and/or texture of the skin.

In some aspects the invention relates to a method of cosmetic treatment comprising the administration of a HS16. As used herein the term "cosmetic method" does not include a method for treatment of the human or animal body by surgery or therapy, or a diagnostic method practised on the human or animal body according to Article 53(c) EPC. In cosmetic methods the subject does not require therapeutic administration of HS16.

The invention also provides a cosmetic composition comprising HS16. The composition may be used to improve the appearance of the skin. Cosmetic compositions may be formulated similarly to pharmaceutical compositions, as described below. A cosmetically effective amount of a HS16 may be administered to the subject. That is, an amount of HS16 effective to induce a cosmetic benefit. This is within the sound judgement of a relevant practitioner, who will appreciate that the appropriate dosages of the active compound or a composition containing the active compound can vary from subject to subject.

In another aspect, the present invention provides a biological scaffold comprising HS16. In some embodiments, the biological scaffolds of the present invention may be used in orthopaedic, vascular, prosthetic, skin and corneal applications. The biological scaffolds provided by the present invention include extended-release drug delivery devices, tissue valves, tissue valve leaflets, drug-eluting stents, vascular grafts, wound healing or skin grafts and orthopaedic prostheses such as bone, ligament, tendon, and cartilage.

In another aspect of the present invention a kit is provided for use in the repair, or regeneration of tissue, said kit comprising (i) a predetermined amount of HS16, and (ii) a predetermined amount of TGFβ1.

HS16 can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that the compounds of the present invention which bear a carboxylic acid group may be delivered in the form of an administrable prodrug, wherein the acid moiety is esterified (to have the form —CO2R'). The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Medicaments and pharmaceutical and cosmetic compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

Administration may be in a "therapeutically effective amount", this being sufficient to show benefit to the individual. The actual amount administered, and rate and time-course of administration, will depend on the nature and severity of the injury or disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Stem Cells

Cells contacted with HS16 include stem cells.

HS16 may be used in the proliferation and/or differentiation of stem cells, and/or the lineage-commitment of stem cells.

The stem cells cultured and described herein may be stem cells of any kind. They may be totipotent, pluripotent or multipotent. They may be embryonic or adult stem cells from any tissue and may be hematopoietic stem cells, neural stem cells or mesenchymal stem cells. Preferably they are adult stem cells.

In this specification, by stem cell is meant any cell type that has the ability to divide (i.e. self-renew) and remain totipotent, pluripotent or multipotent and give rise to specialized cells.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, osteocalcin, BSPII, aggrecan, ALBP, CCAAT/enhancer binding protein-α (C/EBPα), adipocyte lipid-binding protein (ALBP), alkaline phosphatase (ALP), bone sialoprotein 2, (BSPII), Collagen2a1 (COL2A1) and SOX9.

In some preferred embodiments the stem cells are mesenchymal stem cells (MSCs), e.g. capable of differentiation into connective tissue and/or bone cells such as chondrocytes, osteoblasts, myocytes and adipocytes.

Mesenchymal stem cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of the cell's multipotency.

Suitable mesenchymal stem cells may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES *British Journal of Haematology* 121(2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. *Stem Cells Dev.* 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

Mesenchymal stem cells are multipotent progenitor cells with the ability to generate components of cartilage, bone, muscle, tendon, ligament, and fat. These primitive progenitors exist postnatally and exhibit stem cell characteristics, namely low incidence and extensive renewal potential. These properties in combination with their developmental plasticity have generated tremendous interest in their potential use to replace damaged tissues. In essence these stem cells could be cultured to expand their numbers then transplanted to the injured site or after seeding in/on scaffolds to generate appropriate tissue constructs.

Thus, an alternative approach for skeletal, muscular, tendon, ligament and blood repair/regeneration is the selection, expansion and modulation of the appropriate progenitor cells (e.g. mesenchymal stem cells, chondrocytes) in combination with a conductive or inductive scaffold to support and guide regeneration together with judicious selection of specific tissue growth factors.

The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Preferably they are human. Optionally they are non-human. Optionally they are non-embryonic stem cells. Optionally they are not totipotent.

In yet a further aspect of the present invention, a pharmaceutical composition comprising stem cells or other cells generated by any of the methods of the present invention, or fragments or products thereof, is provided. The pharmaceutical composition may be useful in a method of medical treatment. Suitable pharmaceutical compositions may further comprise a pharmaceutically acceptable carrier, adjuvant or diluent.

In another aspect of the present invention, stem cells or other cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells and other cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Mesenchymal Stem Cells

Mesenchymal stem cells (MSCs) were originally isolated from the bone marrow and are present as only 1 in 104-105 total bone marrow mononuclear cells (BMMNC) (Friedenstein et al. 1966). These cells are capable of producing colonies derived from single cell precursors, dubbed the CFU-F (colony forming unit fibroblast) population. MSCs have now been identified in many other tissues including adipose tissue (Gimble and Guilak 2003; Zuk et al. 2001), umbilical cord blood (Bieback et al. 2004; Erices et al. 2000; Goodwin et al. 2001; Kogler et al. 2004; Wagner et al. 2005) and muscle (Jiang et al. 2002).

The minimal criteria for multipotent human mesenchymal stromal cells (MSC) has been set out by the International Society for Cellular Therapy (Dominici et al Cytotherapy (2006) Vol. 8, No. 4, 315-317). They propose three criteria to define human MSC: adherence to plastic, specific surface antigen expression and multipotent differentiation potential. In particular they stated that "First, MSCs must be plastic-adherent when maintained in standard culture conditions using tissue culture flasks. Second, ≥95% of the MSC population must express CD105, CD73 and CD90, as measured by flow cytometry. Additionally, these cells must lack expression (≤2% positive) of CD45, CD34, CD14 or CD11 b, CD79α or CD19 and HLA class II (HLA-DR). Third, the cells must be able to differentiate to osteoblasts, adipocytes and chondroblasts under standard in vitro differentiating conditions."

Dominici et al also stated that the biologic property that most uniquely identifies MSC is their capacity for trilineage mesenchymal differentiation into osteoblasts, adipocytes and chondroblasts using standard in vitro tissue culture-differentiating conditions. They confirmed that differentiation to osteoblasts can be demonstrated by staining with Alizarin red or von Kossa staining, adipocyte differentiation can most readily be demonstrated by staining with Oil red O and chondroblast differentiation can be demonstrated by staining with Alcian blue or immunohistochemical staining for collage type II. Dominici et al state that kits for such assays are commercially available and that demonstrating differentiation should be feasible for all investigators.

Dominici et al also recognise that novel surface markers may be identified in the future that could also be used to define human MSCs. Three such markers are now known: CD49a, SSEA-4 and STRO-1.

Rider et al reported that CD49a+ clones have enhanced expression of CD90 and CD105 compared to unsorted cells and demonstrated that CD49a+ clones readily underwent multilineage differentiation into fat, bone and cartilage compared to unsorted cells, supporting the use of alpha-1 integrin (CD49a) selection for the enrichment of mesenchymal stem cells and provided a strategy for selecting the most multipotent cells from a heterogenous pool of bone marrow mononuclear stem cells (Rider et al. J. Mol. Hist (2007) 38:449-458). Rider et al also report that CFU-F cells are associated with the expression of CD49a, that CD49a expressing CFU-F cells also co-express STRO-1, and CD49a can be used to isolate MSCs from rats and mice in addition to humans indicating that it may be conserved marker for enrichment.

Gang et al report that the stage specific embryonic antigen SSEA-4, commonly used as a marker for undifferentiated pluripotent human embryonic stem cells and cleavage to blastocyst stage embryos also identifies the adult human mesenchymal stem cell population and can be used to isolate MSCs (Gang et al., Blood 2007; 109:1743-1751). Gang et al also describe the use of a monoclonal antibody that binds the surface marker STRO-1 in the enrichment of clonogenic stromal cells (CFU-F) so-called STRO-1$^{+bright}$.

Glycosaminoglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof.

Examples of GAGs are chondroitin sulphate, keratan sulphate, heparin, dermatan sulphate, hyaluronate and heparan sulphate.

As used herein, the term 'GAG' also extends to encompass those molecules that are GAG conjugates. An example of a GAG conjugate is a proteoglycosaminoglycan (PGAG, proteoglycan) wherein a peptide component is covalently bound to an oligosaccharide component.

In preferred embodiments the GAG is heparan sulphate.
Heparan Sulphate (HS)

Heparan sulphate proteoglycans (HSPGs) represent a highly diverse subgroup of proteoglycans and are composed of heparan sulphate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

Preferred embodiments of the present invention concerns HS chains isolated from their core protein. HS chains can be readily separated and isolated from the core protein, e.g. by neuramidase treatment.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulfation at C2 of IdoA and GlcA, O-sulfation at C6 of N-sulphoglucosamine (GlcNS) and occasional O-sulfation at C3 of GlcNS. N-deacetylation/N-sulfation, 2-O-, 6-O- and 3-O-sulfation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulphate side chains consist of alternately arranged D-glucuronic acid or L-iduronic acid and D-glucosamine, linked via (1->4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulphate groups attached to the glucosamine and the uronic acid. In contrast to heparin, heparan sulphate contains less N- and O-sulfate groups and more N-acetyl groups. The heparan sulphate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulphate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulphate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulphate glycosaminoglycans may be genetically described (Alberts et al. (1989) Garland Publishing, Inc, New York & London, pp. 804 and 805), heparan sulphate glycosaminoglycan species isolated from a single source may differ in biological activity. As shown in Brickman et al, 1998, Glycobiology 8, 463, two separate pools of heparan sulphate glycosaminoglycans obtained from neuroepithelial cells could specifically activate either FGF-1 or FGF-2, depending on mitogenic status. Similarly, the capability of a heparan sulphate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulfated domains. Heparinase III depolymerises HS with the NA domains, resulting in the separation of the carbohydrate chain into individual sulfated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulphate on the amino group enabling sulfation of other groups at C2, C6 and C3. "NA" indicates that the amino group is not sulfated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography, e.g. HPLC.

Alternatively they may be analysed by capillary electrophoresis.

Cartilage and Connective Tissue Formation

In another aspect of the present invention a method of promoting the formation of cartilage tissue (chondrogenesis) is provided, comprising administering HS16 to cartilage precursor cells or cartilage stem cells.

The methods of stimulating or inhibiting osteogenesis or formation of cartilage tissue may be conducted in vitro by contacting bone or cartilage precursor or stem cells with HS16, optionally in the presence of exogenously added TGFβ1 protein. The precursor cells or stem cells may be mesenchymal stem cells. Where tissue formation is promoted, the tissue formed may be collected and used for implantation into a human or animal patient.

Accordingly, in one aspect of the present invention, connective tissue is provided wherein the connective tissue is obtained by in vitro culture of mesenchymal stem cells in the presence of HS16 (i.e. exogenous HS16), and optionally in the presence of TGFβ1 (i.e. exogenous TGFβ1). The connective tissue may be bone, cartilage, muscle, fat, ligament or tendon.

The prevention or treatment of disease using HS16 may involve the repair, regeneration or replacement of tissue, particularly connective tissue such as bone, cartilage, muscle, fat, ligament or tendon.

In patients having a deterioration of one of these tissues, administration of HS16 to the site of deterioration may be used to stimulate the growth, proliferation and/or differentiation of tissue at that site. For example, stimulation of mesenchymal stem cells present at, or near to, the site of administration may lead, preferably when TGFβ1 is also present at the site, to the proliferation and differentiation of the mesenchymal stem cells into the appropriate connective tissue, thereby providing for replacement/regeneration of the damaged tissue and treatment of the injury.

Alternatively, connective tissue obtained from in vitro culture of mesenchymal stem cells in contact with HS16 may be collected and implanted at the site of injury or disease to replace damaged or deteriorated tissue. The damaged or deteriorated tissue may optionally first be excised from the site of injury or disease.

Accordingly, HS16 is useful in wound healing in vivo, including tissue repair, regeneration and/or replacement (e.g. healing of scar tissue or a broken bone) effected by direct application of HS16, optionally in combination with TGFβ1 and/or stem cells, to the patient requiring treatment. HS16 is also useful in the in vitro generation of tissue suitable for implantation into a patient in need of tissue repair, regeneration and/or replacement.

Repair and/or Regeneration of Cartilage Tissue

In some aspects the present invention is concerned with the therapeutic use (human and/or veterinary) of HS16 to treat or prevent joint destruction, cartilage degradation, damage to cartilage tissue or loss or degeneration of cartilage tissue.

In some embodiments a disease or condition to be treated by administering HS16, as described herein, may be a disease or condition associated with one or more of joint destruction, cartilage degradation, damage to cartilage tissue and loss or degeneration of cartilage tissue. Cartilage degradation, damage or loss may involve a reduction in cartilage thickness or volume.

Joint destruction, cartilage degradation, damage to cartilage tissue and/or loss or degeneration of cartilage tissue may occur as a result of disease processes, physiological processes and/or as a result of injury or trauma. For example, joint destruction, cartilage degradation, damage to cartilage tissue and/or loss or degeneration of cartilage tissue may be initiated as a result of injury or trauma, and one or more of these processes may then proceed through disease and/or physiological processes.

The disease or condition may be arthritis, optionally trauma or injury-induced arthritis, age-related arthritis or non-age-related arthritis. The arthritis may be osteoarthritis. Osteoarthritis is a clinical syndrome of joint pain and reduced function of the joint (for example, stiffness and/or reduced range of motion). Symptoms include joint pain, stiffness and problems moving the joint. It may be characterised pathologically by localised loss of cartilage, remodeling of bone and/or inflammation. Joints most commonly affected by arthritis are knee joints, hip joints and joints in the hands and feet, but other joints can also be affected.

The subject to be treated in accordance with the methods of the invention may be susceptible to one or more of joint destruction, cartilage degradation, damage to cartilage tissue and loss or degeneration of cartilage tissue even if these processes have not yet commenced. The subject may be susceptible as a result of having a disease or condition associated with one or more of joint destruction, cartilage degradation, damage to cartilage tissue and loss or degeneration of cartilage tissue.

Cartilage may be damaged or degraded as a result of physical processes such as injury or trauma, or mechanical wear and tear and/or biological processes such as disease and physiological processes. Physical processes and biological processes interact to bring about loss, degeneration, degradation or damage of cartilage. For example, injury or trauma or mechanical wear and tear can initiate cartilage damage and engage, for example through inflammation, biological processes that effect and accelerate loss, degeneration, degradation or damage of cartilage.

Injury or trauma may be the result of a fall or sports-related injury or trauma. Mechanical wear and tear may be associated with obesity and/or repetitive actions. For example, mechanical wear and tear may occur as a result of a particular activity or be associated with a particular occupation.

Effectors of biological processes resulting in the loss, degeneration, degradation or damage of cartilage include proteases, metalloproteases, cartilage degrading enzymes upregulated in response to inflammatory mediators, aggrecanases, collagenases, ADAMTS-4, ADAMTS-5, MMP3 and MMP13. Increased catabolic activity of chondrocytes is associated with biological processes resulting in the loss, degeneration, degradation or damage of cartilage. Metabolic activity of chondrocytes can be assayed, for example, by analysis of expression of cartilage genes such as SOX-9, COLII, AGGRECAN, COL1 and TSG-6, or incorporation of radiolabel.

Loss, degeneration, degradation, damage or maintenance of cartilage can be determined by imaging cartilage and/or measuring cartilage over time. Imaging and/or measuring of cartilage may be at a site of interest, for example a site of injury or trauma, or an arthritic joint.

Cartilage loss, degeneration, degradation or damage can be determined by routine methods well known to those skilled in the art. For example, defects (i.e. damage) in cartilage or cartilage loss may be determined by magnetic resonance imaging (MRI) or by arthroscopy.

Cartilage loss, degeneration or degradation can be determined by observation of a reduced amount of cartilage in a joint or at a location relative to a previous measurement of the amount of cartilage in that joint or at that location. Alternatively, cartilage loss, degeneration or degradation can be determined by observation of a reduced amount, thickness or volume of cartilage in a joint or at a location relative to an equivalent joint or location not experiencing cartilage loss, degeneration or degradation.

Damage to cartilage observed by arthroscopy may be graded according to the International Cartilage Repair Society (ICRS) grading system, as follows:
  0=(normal) healthy cartilage;
  1=the cartilage has a soft spot or blisters
  2=minor tears visible in the cartilage
  3=lesions have deep crevices (more than 50% of the cartilage layer)
  4=the cartilage tears exposes the underlying (subchondral) bone.

Cartilage of grade 2/3 defects may have a fibrillated or shredded appearance. Damage to cartilage can also be assessed by histopathology according to the Osteoarthritis Research Society International (OARSI) grading system described in Pritzker et al., Osteoarthritis Cartilage 2006 14(1): 13-29.

Expression and/or activity of enzymes associated with cartilage degradation, or of genes or enzymes known to be upregulated in response to cartilage degradation can also be used to determine loss, degeneration, degradation, damage or maintenance of cartilage. Similarly, catabolic activity of chondrocytes can be assayed to investigate loss, degeneration, degradation, damage or maintenance of cartilage.

Inhibition of joint destruction or cartilage degradation, or prevention or delay of degradation of or damage to or loss of cartilage tissue, or maintenance of effective cartilage tissue as a result of administration of a therapeutically effective amount of a polypeptide or polynucleotide of the invention can be determined by finding no or minimal loss, degeneration, degradation or damage of cartilage in a joint or at a location, relative to a previous measurement of the amount of cartilage in that joint or at that location. Alternatively, inhibition of joint destruction or cartilage degradation, or prevention or delay of degradation of or damage to or loss of cartilage tissue, or maintenance of effective cartilage tissue can be determined by finding reduced or slowed loss, degeneration, degradation or damage of cartilage in a joint or at a location relative to an untreated control joint or location.

Gene expression—e.g. of genes associated with cartilage loss, degeneration, degradation or damage—can be determined by a variety of methods well known to the skilled person. For example, the level of expression of a gene can be determined in a sample, e.g. a biopsy or tissue sample, by quantitative real-time PCR.

Genes associated with cartilage loss include, but are not limited to, genes encoding proteases, metalloproteases, cartilage degrading enzymes upregulated in response to inflammatory mediators, aggrecanases, collagenases, ADAMTS-4, ADAMTS-5, MMP3 and MMP13.

The level of expression or activity of a protein or enzyme e.g. associated with cartilage loss, degeneration, degradation or damage can be determined by routine methods known to the skilled person. For example, the level of expression of a protein in a sample, e.g. a biopsy or tissue sample, can be determined by immunoblotting or ELISA. The level of activity of an enzyme can be determined in a sample, e.g. a biopsy or tissue sample, by using a reporter assay for the activity of that enzyme. Similarly, the metabolic activity of chondrocytes in a sample e.g. a biopsy or tissue sample can be determined.

Cartilage degradation/destruction/loss/damage and/or joint destruction can be correlated with clinical symptoms of a disease or condition associated with loss, degeneration, degradation or damage to cartilage tissue or joint destruction, and so these may also be useful for investigating or estimating cartilage degradation/destruction/loss/damage or joint destruction, metabolic activity of chondrocytes, or expression and/or activity of cartilage degrading enzymes.

Bone Fracture

In some aspects the present invention is concerned with the therapeutic use (human and/or veterinary) of HS16 to treat bone fracture.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects, bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS16 include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using HS16 include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using HS16 also include those of the head (skull) and neck, including those of the face such as the jaw, nose and cheek. HS16 may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of HS16 may be on cells within, adjacent to, or caused to migrate into the wound site and may be on the mesenchymal stem cells, bone stem cells, the preosteoblasts or the osteoblasts, or on any of the ancillary or vasculogenic cells found or caused to migrate into or within the wound bed.

HS16 and pharmaceutical compositions and medicaments comprising HS16 are provided for use in a method of treatment of bone fracture in a mammalian subject. Treatment may comprise wound healing in bone. The treatment may involve repair, regeneration and growth of bone. HS16 facilitates fracture repair by facilitating new bone growth. HS16 acts to improve the speed of fracture repair enabling bone healing to occur faster leading to improved recovery time from injury. Treatment may lead to improved bone strength.

Treatment may also include treatment of osteoporosis or osteoarthritis.

Administration of HS16 is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound. Medicaments and pharmaceutical compositions according to the present invention may be formulated for administration by a number of routes. Most preferably HS16 is formulated in fluid or liquid form for injection.

In some embodiments the HS16 is formulated as a controlled release formulation, e.g. in a drug capsule for implantation at the wound site. The HS16 may be attached to, impregnated on or soaked into a carrier material (e.g. a biomaterial) such as nanofibres or biodegradable paper or textile.

Pharmaceutical compositions, medicaments, implants and prostheses comprising HS16 may also comprise TGF-β1. Owing to the ability of HS16 to bind TGF-β1, the HS16 may act as a carrier of TGF-β1 assisting in delivery of TGF-β1 to the wound site.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS16 doses may be administered in accordance with the guidance of the prescribing medical practitioner. Purely by way of example, HS16 may be delivered in dosages of at least 1 ng/ml, more preferably at least 5 ng/ml and optionally 10 ng/ml or more. Individual HS16 dosages may be of the order less than 1 mg and greater than 1 μg, e.g. one of about 5 μg, about 10 μg, about 25 μg, about 30 μg, about 50 μg, about 100 μg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS16 may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS16 may be administered directly to (e.g. applied to) the fracture during the surgical procedure.

Biomaterials

Pharmaceutical compositions and medicaments of the invention may take the form of a biomaterial that is coated and/or impregnated with HS16. An implant or prosthesis may be formed from the biomaterial. Such implants or prostheses may be surgically implanted to assist in tissue regeneration, tissue restructuring and/or tissue re-modelling.

HS16 may be applied to implants or prostheses to accelerate new tissue formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS16. Impregnation may comprise forming the biomaterial by mixing HS16 with the constitutive components of the biomaterial, e.g. during polymerisation, or absorbing HS16 into the biomaterial. Coating may comprise adsorbing the HS16 onto the surface of the biomaterial.

The biomaterial should allow the coated or impregnated HS16 to be released from the biomaterial when administered to or implanted in the subject. Biomaterial release kinetics may be altered by altering the structure, e.g. porosity, of the biomaterial.

In addition to coating or impregnating a biomaterial with HS16, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. Impregnation or coating with TGF-β1 may be preferred.

Biomaterials coated or impregnated with HS16 may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated tissue in situ in the subject. Alternatively a non-biodegradable biomaterial may be used, e.g. to guide tissue regeneration over a large discontinuity and/or to act as a structural support during healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a crosslinked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices*. 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications*. 2000; 14(3); 229-242; DeBlois Cote M F. Doillon C J. Heparin-fibroblast growth factor fibrin complex: in vitro and in vivo applications to collagen based materials. *Biomaterials*. 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

The biomaterial can be supplemented with additional cells. For example, one can "seed" the biomaterial (or co-synthesise it) with stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Culture Media

Culture media comprising HS16 (preferably isolated HS16) may be of any kind but is preferably liquid or gel and may contain other nutrients and growth factors (e.g. TGFβ1, FGF-2). Culture media may be prepared in dried form, e.g. powered or lyophilised form, for reconstitution in to liquid or gel. HS16 will preferably be present in non-trace amounts. For example, the concentration of HS16 in the culture media may range between about 1 ng/ml culture media to about 1000 ng/ml culture media. Preferably, the concentration of HS16 in the culture media is about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, or 5 ng/ml or less.

Dosages of Heparan Sulphate

In both in vitro and in vivo uses, HS16 may be used in concentrations or dosages of about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or about between 0.3-5 µg/ml, 0.3-4, 0.3-3, 0.3-2.5, 0.3-2, 0.3-1.5, 0.3-1.0, 0.3-0.9, 0.3-0.8, 0.3-0.7, 0.3-0.6, 0.3-0.5, 0.3-0.4, 1-2, 1-1.75, 1-1.5, 1-1.25, 1.25-2, 1.5-2, or 1.75-2 µg/ml.

In some embodiments a priming dose of HS16 may be administered prior to administration of a therapeutic dose. The priming dose may act to pre-bind activated TGFβ1. The priming dose and therapeutic dose may each be independently selected from one of the values or ranges given above.

Formulations

While it is possible for HS16 to be administered alone, it is preferable to present it as a pharmaceutical or cosmetic formulation (e.g., composition, preparation, medicament) comprising HSX together with one or more other pharmaceutically or cosmetically acceptable ingredients well known to those skilled in the art, including, but not limited to, pharmaceutically or cosmetically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

Thus, the present invention further provides pharmaceutical or cosmetic compositions, as defined above, and methods of making a pharmaceutical or cosmetic composition comprising admixing at least one active compound, as defined above, together with one or more other pharmaceutically or cosmetically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

Formulations may suitably be in the form of liquids, solutions (e.g., aqueous, non-aqueous), optionally saline solutions, suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically or cosmetically acceptable ingredients.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Ointments are typically prepared from the active compound and a paraffinic or a water-miscible ointment base. Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues. Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations. Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for parenteral administration (e.g., by injection), include aqueous or non-aqueous, isotonic, pyrogen-free, sterile liquids (e.g., solutions, suspensions, saline solutions), in which the active compound is dissolved, suspended, or otherwise provided (e.g., in a liposome or other microparticulate). Such liquids may additional contain other pharmaceutically acceptable ingredients, such as antioxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, saline, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

TGFβ1

In this specification TGFβ1 refers to transforming growth factor 1 which is a member of the transforming growth factor beta superfamily.

The amino acid sequence of TGFβ1 from *Homo sapiens* is available in Genbank under Accession no. NP_000651.3 (GI:63025222) [SEQ ID NO:2].

TGFβ1 is synthesized as a pre-pro-protein which subsequently undergoes proteolytic cleavage. Monomers dimerize through disulphide bridges to form a pro-TGFβ1 dimer. The TGFβ1 dimer is then cleaved to give the small latent TGFβ complex (SLC), in which the latency associated peptide (LAP) and mature peptide are associated through non-covalent bonds. The large latent TGFβ1 complex (LLC) is formed by covalent attachment of the large latent TGFβ1 binding protein (LTBP) to the SLC.

As used herein, "TGFβ1" or "a TGFβ1 protein" includes pre-pro-TGFβ1, pro-TGFβ1, mature TGFβ1, and latent TGFβ1. The pre-pro-TGFβ1, pro-TGFβ1, mature TGFβ1 and latent TGFβ1 forms may be comprised in protein complexes, such as, for example, the small latent TGFβ1 complex or large latent TGFβ1 complex.

In this specification "TGFβ1" includes proteins or polypeptides having at least 70%, more preferably one of 75%, 80%, 85%, 90%, 95%, 96%, 97%, 98%, 99% or 100% sequence identity with the amino acid sequence of TGFB1.

The TGFβ1 protein or polypeptide preferably also includes a heparin binding domain having the amino acid sequence of SEQ ID NO:1, or an amino acid sequence having one of 75%, 80%, 85%, 90%, 95%, 96%, 97%, 98%, or 99% sequence identity to SEQ ID NO:1.

A TGFβ1 protein or polypeptide may be a fragment or truncate of a full length TGFβ1 protein or polypeptide. For example, TGFβ1 may be pre-pro-TGFβ1, pro-TGFβ1 or the mature TGFβ1 polypeptide.

The TGFβ1 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

Dosages of TGFβ1

In both in vitro and in vivo uses, TGFβ1 may be used in combination with HS16. In some cell culture methods of the present invention exogenous HS16 is added to the culture. Suitable concentrations or dosages of TGFβ1 include about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or between about range 0.1-5 ng/ml, 0.1-0.2, 0.1-0.3, 0.1-0.4, 0.1-0.5, 0.1-0.6, 0.1-0.7, 0.1-0.8, 0.1-0.9, 0.1-1.0, 0.1-1.5, 0.1-0.2.0, 0.1-2.5, 0.1-3.0, 0.1-3.5, 0.1-4.0, 0.1-4.5, 0.1-5.0 ng/ml.

In some embodiments, in vitro and in vivo uses of HS16 exclude the addition of exogenous TGFβ1. For example, in some cell culture methods of the present invention exogenous TGFβ1 is not added to the culture.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 6A to 6F. Isolation of affinity selected TGF-β1-binding HS (HS16$^{+ve}$). (A) Amino acid sequence of mature TGF-β1 showing the peptide used for isolation of the TGF-β1-binding HS population from commercially available HS$^{PM}$ [SEQ ID NO:3]. (B) Chart showing result of $^3$H-heparin binding assay to determine the peptide's ability to bind to $^3$H-heparin. The peptide was adsorbed onto a nitrocellulose membrane and then allowed to bind to $^3$H-heparin. The amount of heparin bound to the peptide was quantified with a scintillation counter. PBS served as a negative control. Error bars represent standard deviation, n=2. (C) Chromatogram of the HS fractions obtained after affinity selection with the TGF-β1 peptide. HS that did not bind to the peptide (HS16$^{-ve}$) eluted first, while the HS that bound to the peptide (HS16$^{+ve}$) eluted with 1.5 M NaCl. (D) Amino acid sequence of mature TGF-β1 showing the peptide used for isolation of the TGF-β1-binding HS population from commercially available HS$^{PM}$ (P4) and three other peptides (P1, P2 P3) also tested. (E) Chart showing relative binding of HS$^{PM}$ to PBS and each of P1, P2, P3, P4. (F) Diagram illustrating chromatographic isolation of HS16.

FIG. 19. Sequence alignment of mature human [SEQ ID NO:3] and rabbit TGF-β1 [SEQ ID NO:4]. Amino acid residues in the predicted heparin-binding domain of mature human TGF-β1 are underlined and lysines (K) identified by the "Protect and Label" technique are in bold.

FIGS. 20A and 20B. Macroscopic scores of treatment groups. Scatter plot of ICRS I scores for each treatment group. (A) Middle line represents the mean score, error bars represent SE. (B) Line represents the median score.

EXAMPLES

Example 1

Figure 1A:
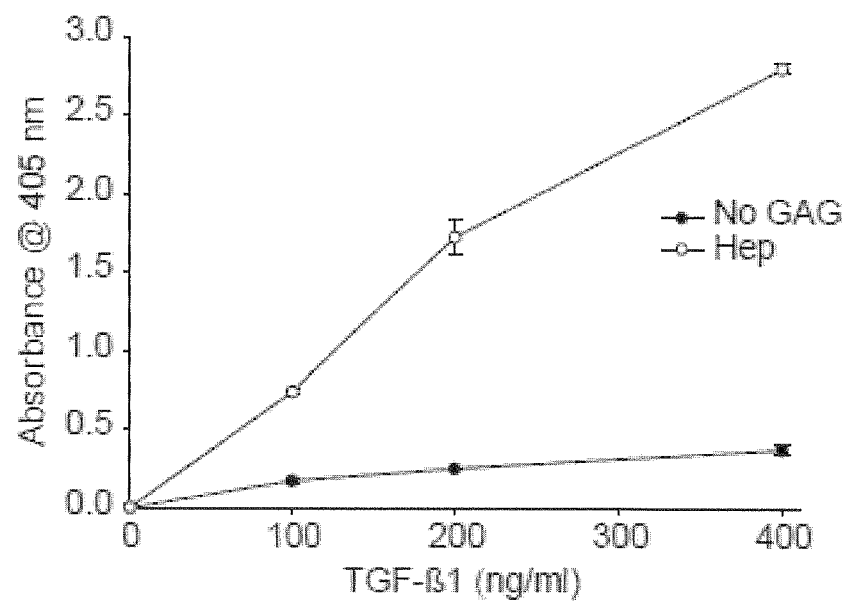
FIGS. 1A and 1B. Charts showing heparin binds to TGF-β1. (A) Chart showing results of GAG-binding plate assay to determine ability of TGF-β1 to bind to heparin. Error bars represent standard deviation, n=3. (B) SPR sensogram showing the change in binding response to various concentrations (50 to 800 nM) of injected TGF-β1. A standard curve was prepared by plotting the binding response (RU) as a function of the injected protein. The $K_d$ for TGF-β1 binding to heparin was estimated to be ~0.475 μM.

Structural Requirements for Heparin/Heparan Sulfate-Transforming Growth Factor-β1 Interactions and Signal Potentiation Background: Heparin is able to bind to and potentiate transforming growth factor-β1 (TGF-β1) signaling.
Results: The molecular determinants of the interaction of heparin/heparan sulfate (HS) and TGF-β1 were identified.

Conclusion: There are defined structural requirements for the interaction of TGF-β1 with heparin/HS which influence TGF-β1 signal potentiation.

Significance: An understanding of HS-TGF-β1 interactions can guide TGF-β1 therapy development.

Abstract

Transforming growth factor-β1 (TGF-β1) is a heparin binding protein that has been implicated in a number of physiological processes, including the initiation of chondrogenesis by human mesenchymal stem cells (hMSCs). Here we show that heparin can bind to and potentiate TGF-β1 signaling for hMSCs. This potentiation occurs through the modulation of the TGF-β1 pathway via TGF-β receptors and leads to the upregulation of early chondrogenic genes. Molecular interaction and cell-based assays also demonstrated that heparin chains that are 18-22 saccharides (dp18-22) in length and lack 2-O-sulfation are optimal for binding TGF-β1. Interrogation of the interaction between TGF-β1 and heparin through structural proteomics allowed the identification of novel lysine residues on TGF-β1 involved in heparin binding. With this information we isolated a subfraction of porcine mucosal heparan sulfate (HS) that had an increased affinity for TGF-β1. This TGF-β1-binding HS was able to better bind to and potentiate the activity of both TGF-β1 and latent TGF-β1 compared to the original starting HS. This study is the first to report on the structural requirements for the interaction of heparin with TGF-β1. It also lays the foundation for the development of an HS-based strategy to modulate TGF-β1 signaling for cartilage repair, where exogenous protein doses could be either reduced or dispensed with.

Introduction

The glycosaminoglycans (GAGs) heparan sulfate (HS)[1] and heparin are structurally related, linear polysaccharides that are known to bind numerous extracellular proteins and growth factors and modulate their functions (1). Transforming growth factor-β1 (TGF-β1) is a potent heparin-binding growth factor (2-5) that has been shown to play roles in fibrosis (6,7), skin healing (8), cancer metastasis (9,10) and chondrogenesis (11-15). This ability of TGF-β1 to drive the chondrogenic differentiation of human mesenchymal stem cells (hMSCs) and maintain the chondrogenic phenotype has made it of particular interest in the development of cartilage repair strategies (13, 15-18).

While appearing successful initially, such approaches face significant barriers in their translation into the clinic, as supraphysiological doses of TGF-β1 are often employed to overcome clearance, and even modest doses have been shown to produce undesirable outcomes, such as synovial inflammation (19,20). Apart from the problem of non-physiological doses, there is also the ongoing need to localize the growth factor to the site of treatment to prevent it from triggering systemic side effects, including fibrosis and oncogenesis (9, 10, 21). Additionally, sensitivity to TGF-β1 decreases with age (22), so adequate TGF-β1 dosing presents even more risk for aged patients. In response to these challenges, new strategies are being developed that reduce or completely remove the need for exogenous growth factors, better localize and control the delivery of the growth factor at the site of treatment, and boost either cellular sensitivity to the growth factor or the factor's signaling efficiency. Some groups have already addressed the first two hurdles through the use of self-assembling peptide amphiphiles (23,24), and have demonstrated that endogenous levels of TGF-β1 are sufficient to drive local MSC differentiation (25). However, synthetic peptide amphiphiles pose significant immunogenic risk, and fail to address the need to enhance signaling activity within the desired cellular targets. An ideal therapy would act to enhance TGF-β1 signaling without exogenous TGF-β1 application.

Our group has previously shown that HS GAGs are able to modulate the effects of a number of clinically relevant growth factors (26-29). Here we examine the mechanism of action of heparin and HS association with TGF-β1, and their potentiation of signaling within hMSCs. We demonstrate that the binding of heparin to TGF-β1 potentiates its activity via the TGF-β type I receptor-SMAD2/3 pathway, and that there are specific constraints on the structural requirements for such binding. Additionally, we utilize this information to isolate a TGF-β1-binding population of HS that is compositionally different from, and more effective than porcine mucosal HS ($HS^{PM}$) in potentiating TGF-β1 signaling. The work here paves the way for further studies of TGF-β1-HS interaction, and aids the development of HS-based strategies to regulate hMSC behavior for tissue repair.

Experimental Procedures

Human MSC Isolation and Cell Culture

Primary hMSCs (Lonza) were isolated from the bone marrow mononuclear cells of a young healthy adult human donor by plastic adherence and characterized as previously described (30,31). The adherent cells were maintained in a basal media consisting of DMEM-low glucose (1000 mg/l, DMEM-LG) supplemented with 10% fetal calf serum, 100 U/ml penicillin, 100 µg/ml streptomycin and 2 mM L-glutamine, and cultured under standard conditions at 37° C. and 5% $CO_2$ in a humidified atmosphere. Media replacement was every three days. Cells were detached with 0.125% trypsin/Versene (pH 7.0) upon reaching 75-80% confluence, and re-plated at a density of 3,000 cells/$cm^2$ under the same culture conditions. All experiments were carried out with cells at passage 5.

Chondrogenic Differentiation

Chondrogenic differentiation was carried out using a modified micromass culture system as described by Zhang et al. (32). Briefly, passage 4 hMSCs were harvested and resuspended in chemically defined chondrogenic media (PT-3003, Lonza) at $2 \times 10^7$ cells/ml. Droplets of 12.5 µl were then seeded into the middle of each well in a 24-well plate and left to adhere at 37° C. for 2 h, after which, 500 µl of chondrogenic media supplemented with either 10 ng/ml of TGF-β1 (100-21C, PeproTech) alone (Media) or TGF-β1 with 10 µg/ml of heparin (Sigma-Aldrich) (Media+Hep) was added to each well. The cell droplets coalesced into spherical masses after 24 h and the micromasses harvested on day 3.

Surface Plasmon Resonance (SPR)-Based Analysis of TGF-β1-GAG Interactions

Biotinylated heparin was prepared based on the protocol reported by Hernaiz et al. (33). Briefly, 20 mg of heparin was filter-sterilized (0.22 µm) in 1 ml of water and incubated with 8.6 µmol of N-hydroxysuccinimide-biotin (NHS-biotin) (Pierce) in 20 µl of dimethyl sulfoxide (DMSO) for 2 h at 4° C. The biotinylated heparin was then extensively dialyzed (7000 MWCO) to remove unreacted biotin. Immobilization of the biotinylated heparin onto a streptavidin (SA) sensor chip (GE Healthcare) was carried out using the immobilization wizard on the Biacore T100 (GE Healthcare) with a targeted immobilization level of approximately 40 response units (RUs). HBS-EP running buffer (10 mM HEPES, 150 mM NaCl, 3.0 mM EDTA, 0.05% (v/v) Tween 20, pH 7.4) was used for the immobilization.

TGF-β1-heparin interactions were effected by preparing a series of TGF-β1 protein samples (50 to 800 nM final concentration) diluted in HBS-EP-0.1 running buffer (0.1% instead of 0.05% (v/v) Tween 20). For competitive binding experiments, a final concentration of 200 nM TGF-β1 in HBS-EP-0.1 was mixed with either 5 or 10 μg of one of the following GAGs: heparin (Hep); size-fractionated heparin (degree of polymerization dp4, 6, 8, 10, 12, 14, 16, 18, 20, 22 and 24) (Iduron); selectively desulfated heparin (2-O-desulfated, 6-O-desulfated and N-desulfated) (Iduron); $HS^{PM}$ (HO-03103, Celsus Laboratories); affinity-isolated TGF-β1-binding HS ($HS16^{+ve}$); or TGF-β1-non-binding HS ($HS16^{-ve}$). The sample solutions were then injected over the heparin-coated chip at a flow rate of 30 μl/min for 120 s, with HBS-EP-0.1 being subsequently passed over the chip for a further 1200 s to monitor TGF-β1 dissociation. After dissociation, the sensor surface on the chip was regenerated by 2 washes of 2 M NaCl injected at 30 μl/min for 60 s. The response was measured as a function of time (sensogram) at 25° C. The maximum binding response for each condition was normalized to the response obtained from TGF-β1 alone.

GAG-Binding Plate Assay

To determine the ability of TGF-β1 to bind to heparin, we utilized positively-charged GAG-binding plates (Iduron) as a capture substrate. GAGs were immobilized in each well and then challenged with TGF-β1 according to the manufacturer's instructions. Briefly, triplicate wells were first pre-coated with 5 μg/ml of full length heparin, size-fractionated heparin (dp14, 16, 18, 20, 22 and 24) or selectively de3ed heparin prepared in standard assay buffer (SAB: 100 mM NaCl, 50 mM sodium acetate, 0.2% v/v Tween 20, pH 7.2), and then incubated overnight at room temperature. The plates were next washed carefully three times with SAB, blocked with 250 μl of blocking solution (0.4% w/v fish skin gelatine, Sigma-Aldrich, in SAB) and incubated for 1 h at 37° C. TGF-β1 was then dissolved in blocking solution at a concentration of 100, 200, or 400 ng/ml. The plates were washed three times with SAB and each dilution of protein (200 μl) was dispensed into triplicate wells and incubated for 2 h at 37° C., rinsed with SAB and 200 μl of 750 ng/ml monoclonal mouse anti-TGF-β1 antibody (MAB2401, R&D Systems) added in blocking solution. Plates were then incubated for 1 h at 37° C., washed with SAB, and 200 μl of 1 μg/ml polyclonal goat anti-mouse biotinylated antibody (ab6788, Abcam) added in blocking solution. Again, plates were incubated for 1 h at 37° C., washed with SAB, and 200 μl of 220 ng/ml ExtrAvidin AP (Sigma-Aldrich) was added in blocking solution, incubated for 30 min at 37° C., and then rinsed with SAB. Finally, 200 μl of development reagent (SigmaFAST p-Nitrophenyl phosphate, Sigma-Aldrich) was added, incubated at 37° C. for 40 min and read at 405 nm within 1 h.

Differential Scanning Fluorimetry (DSF)

DSF was performed on a 7500 Fast Real PCR System (software version 1.4, Applied Biosystems), as described previously (34,35). TGF-β1 (2.5 μM) was tested with or without heparin (25 μM). To facilitate the melting of TGF-β1, 10 mM of dithiothreitol (DTT) was added to the reaction mix. Experiments were run as previously described (34). First derivatives of the melting curves were calculated using Origin 7 (OriginLab Corp.) to determine the melting temperature of TGF-β1 under the various conditions. Experiments were run in triplicate, but for the purposes of clarity, the data presented here only shows the average of the replicates.

Cell Lysis and Western Blotting

Human MSCs were cultured in 6-well plates in basal media for 24 h at a density of 10,000 cells/cm². TGF-β1 treatments were then prepared at either 1 ng/ml or 5 ng/ml alone or in the presence of either 10 μg/ml or 40 μg/ml of full length heparin, or 1 ng/ml of TGF-β1 with 10 μg/ml size-fractionated or selectively desulfated heparin, $HS^{PM}$, HS16+ or HS16-, and incubated at room temperature for 10 min before being added to the cells. Latent TGF-β1 (LTGF-β1) treatments were similarly prepared at 3.3 ng/ml alone or with 10 μg/ml of the various GAGs described above. For inhibitor studies, the cells were pre-treated for 30 min with 10 μM SB431542 (Sigma-Aldrich) or DMSO before treatment with TGF-β1. The cells were then subjected to the various TGF-β1 treatments for 1, 6 or 24 h and lysed in 2× Laemmli buffer, before being resolved on a 4-12% SDS-PAGE gel. Samples were then immunoblotted with antibodies against SMAD2/3 (#3102, Cell Signaling), phosphorylated SMAD2 (pSMAD2, #3108, Cell Signaling), phosphorylated SMAD3 (pSMAD3, #9520, Cell Signaling) and actin (MAB1501R, Millipore). Densitometry was carried out using Quantity One software (version 4.6.6, Bio-Rad).

Reverse Transcription and Quantitative PCR (qPCR)

Total RNA was isolated from chondrogenic micromass pellets using TRIZOL reagent (Invitrogen, Life Technologies) according to the manufacturer's protocol. Reverse transcription was carried out on 1 μg RNA using the Super-Script® VILO™ cDNA Synthesis Kit (Invitrogen, Life Technologies) following the manufacturer's instructions, with the incubation at 42° C. being carried out for 2 h instead of 1 h. Each qPCR contained 40 ng cDNA, 1 μl TaqMan® primer-probe mix per gene, and 10 μl Taqman® Fast Universal PCR Master Mix (Applied Biosystems, Life Technologies) in a final volume of 20 μl. Thermal cycling conditions were 95° C. for 20 s, followed by 45 cycles of 95° C. for 3 s and 60° C. for 30 s. Each qPCR was run in duplicate and gene expression was normalized to HPRT1 expression to obtain the ΔCt value. The average value of biological triplicates was taken. Chondrogenic micromass pellets cultured in media without heparin (Media) were used as controls (ΔΔCt). Relative expression levels for each primer set were expressed as fold changes by the $2^{-\Delta\Delta Ct}$ method (36). The following TaqMan® primer-probe assays (Applied Biosystems, Life technologies) were used: HPRT1 (Assay ID: Hs01003267_m1), SOX9 (Assay ID: Hs00165814_m1) and COMP (Assay ID: Hs00164359_m1).

Protect and Label

The heparin-binding sites on TGF-β1 were identified by the "Protect and Label" approach, as described by Ori et al. for FGF-2 (37), except that 1 nmol of TGF-β1 protein and 0.1% (w/v) RapiGest™ SF Surfactant (Waters Corporation) was used to elute the protein from the mini-column. Digested and biotinylated peptides were purified on a C18 ZipTip (Millipore) and then analyzed by tandem mass spectrometry (MS). Up to 2 μg of the biotinylated peptides were injected into an LTQ Velos instrument (Thermo) using an EASY-nLC (Proxeon). Peptides were separated on a PicoFrit™ column (HALO, C18, 90 Å, 2.7 μm, 75 μm (ID)×100 mm length) (New Objectives) using a 60 min linear gradient (2-40% (v/v) acetonitrile in 0.1% formic acid). Data acquisition was performed using a TOP-10 strategy where survey MS scans were acquired in the dual pressure linear ion trap. MS scans ranging from 310 to 1400 m/z, AGC target 3e4 and maximum injection time of 10 ms. The 10 most intense ions with an ion intensity above 1000 and a charge state excluding one were sequentially isolated to a maximum AGC target value of 4e4 for a maximal 100 ms and fragmented by Collision Induced Dissociation (CID) using a normalized collision energy of 30%. A dynamic exclusion list was applied using an exclusion list size of 500, one repeat count, repeat duration of 45 s, exclusion duration of 30 s as well as a mass width of 1.0 low and 1.5 high. Expiration was disabled.

Data analysis was performed using Mascot search (version 2.3, Matrix Science) using the ipi.HUMAN.v3.86.decoy database (183,568 sequences) and applying the following parameters: digest, chymotrypsin (FWYL/P); maximum missed cleavages, 2; Fixed modifications, carbamidomethyl (Cys); possible modifications, acetyl (Lys), acetyl (Protein N-term), biotin (Lys), oxidation (Met); parental ion tolerance, 2 Da; fragment ion tolerance, 0.8 Da. Biotinylated peptides with a Mascot score higher than 20 were manually validated.

$^3$H-Heparin-Binding Assay

To determine the heparin-binding ability of the TGF-β1-derived peptide (sequence -RKDLGWKWIHEPKGYH-AHX-K(Biotin) [AHX=6-aminohexanoic acid]; [SEQ ID NO:7]), 0.5 mg of the peptide was reconstituted in 1 ml of phosphate buffered saline (PBS). The peptide was then adsorbed onto a nitrocellulose disc (6 mm diameter) by incubating the disc in 1 ml of the reconstituted peptide at room temperature for 1 h with constant shaking. Discs incubated in PBS alone served as negative controls. After adsorption, the discs were dried in a vacuum oven at 80° C. and −10 in Hg for 45 min, washed 3 times with PBS, and then incubated with 1 ml of 0.1 µCi/ml $^3$H-heparin for 16 h at room temperature with constant shaking. The discs were then washed 4 times with PBS and the amount of $^3$H-heparin bound measured with a scintillation counter.

Affinity Isolation of HS16$^{+ve}$

Isolation of HS16$^{+ve}$ was carried out as previously described (29) using the TGF-β1 peptide sequence described above.

Briefly, 3 mg of the peptide was coupled to a HiTrap™ streptavidin HP column (GE Healthcare, Buckinghamshire, UK), which was then used for affinity chromatography with commercially available porcine mucosal HS (HSPM, Celsus Laboratories Inc, Ohio, USA). HSPM was dissolved at 1 mg/mL in low-salt buffer (20 mM phosphate, 150 mM NaCl, pH 7.2), loaded at a flow rate of 0.2 mL/min and the column washed in the same buffer until the baseline absorbance at 232 nm (A232) reached zero. Bound HS was eluted in a single step with high-salt buffer (20 mM Phosphate, 1.5 M NaCl, pH 7.2), peak fractions were monitored at A232, collected, and the column re-equilibrated with low-salt buffer. The eluted (HS16+ve) and flow-through (HS16−ve) peaks were collected separately, freeze dried, desalted on a HiPrep™ 26/10 desalting column (GE Healthcare, Buckinghamshire, UK) at a flow rate of 10 mL/min, freeze-dried again and stored at −20° C.

Proton NMR Spectroscopy

HS$^{PM}$, HS16$^{+ve}$ and HS16$^{-ve}$ samples were pooled and exchanged in D$_2$O three times (three passes of dissolution of the dried powder in D$_2$O (0.5 to 1 mL) and freeze drying until fully lyophilized) and the dry weight determined. NMR analysis was carried out at 30° C. in 5 mm tubes as D$_2$O solutions and included tBuOH (0.2 mg/mL) as an internal standard. The optimum concentration for comprehensive data-sets was ~15 mg/mL ($^1$H), albeit the HS preparations were approximately 3 mg/mL. Proton (500 MHz) NMR spectra were recorded on a three channel Bruker AvanceIII500. The probe was a Bruker two channel 5 mm broadband Nuclei Probe (31P-109Ag) equipped with actively shielded 50 G/cm Z-axis Pulsed Field Gradients. The NMR spectra were phase corrected as required and were reference to tBuOH ($^1$H δ 1.24 ppm; $^{13}$C (methyl) δ 30.29 ppm). Assignments for signals were based on those reported by Guerrini et al. (38).

Alcian Blue/Silver Stain of GAG in Native PAGE

To examine the size distribution of polysaccharide chains in HSPM, HS16+ve and HS16−ve samples, 2 µg of each GAG was run on a 12% native PAGE gel that had been pre-run at 80 V for 30 min to remove residual ammonium persulfate and tetramethylethylenediamine (TEMED). Samples were prepared in a final volume of 25 µL with 4× electrophoretic mobility shift assay (EMSA) buffer (40 mM Tris-HCl, pH 8.0, 40% (v/v) ultrapure glycerol, 0.4% (v/v) NP40 and 400 mM KCl) diluted to 1× with Tris-Glycine buffer (25 mM Tris, 192 mM Glycine). A molecular weight ladder and BSA were used as molecular weight markers, while heparin was used as a positive control for the Alcian Blue staining. The gel was then stained with 0.5% (w/v) Alcian Blue in 2% (v/v) acetic acid for 45 min, destained in 2% (v/v) acetic acid for 15 min and washed in MilliQ water overnight to remove excess stain. Subsequently, the gel was silver stained to visualise the protein markers and enhance the contrast of the Alcian Blue-stained GAGs.

HPLC-Size Exclusion Chromatography-Refractive Index (HPLC-SEC-RI) of Affinity Isolated HS HPLC-SEC-RI chromatograms were obtained using a TSK gel G4000PWXL (7.8 mm×30 cm) and a TSK gel G3000PWXL (7.8 mm×30 cm) (TOSOH Corp.) in series on a Waters 2690 Alliance system with a Waters 2410 refractive index monitor (range 64). The dn/dc for quantification from the RI was set at 0.129 (39). Samples were injected (50 µg) and eluted with 50 mM ammonium acetate with a flow rate of 0.5 ml/min, at room temperature. Data was collected and analyzed using DAWN Astra software (Version 4.73.04, Wyatt Technology Corp.). The elution volumes of molecular weight (MW) standards were based on the elution volumes of heparin oligosaccharides (Iduron and Dextra Laboratories) run under the same conditions. Run times for these columns were 100 min in both cases. All GAG samples were at a concentration of 1 mg/ml in water.

Digestion of HS Samples with Heparin Lyase Enzymes

HS$^{PM}$, HS16$^{+ve}$ and HS16$^{-ve}$ samples were solubilized in water (1100 µl) and filtered (Minisart RC15, 0.2 µm syringe filter unit, Sartorius Stedim, #17761) to remove any particulate matter. As a further clean-up step, the filtered solution was passed through a 2000 MWCO membrane (Vivaspin 2, Hydrosart, Sartorius Stedim, #VS02H91, 2000 MWCO HY membrane, 2 mL ultrafiltration spin column) by centrifugation (4000 rpm, 1 h, 15° C.). The retentate was washed with water (3×1 ml), recovered from the filter and lyophilized. The purified HS samples were solubilized in water (1 mg/ml) and aliquots (2×~1 ml) of each freeze-dried sample were taken for analysis. The HS samples were digested to di- and oligosaccharides by the sequential addition of heparin lyase enzymes (Heparin lyase I, II and III, Ibex Technologies) based on the method of Brickman et al. (40), but with some modifications. The dry HS samples were re-solubilized in digestion buffer (500 µl; 50 mM sodium phosphate buffer, pH 7.0) and heparin lyase I (5 µl; 5 mIU) was added to each sample. The samples were incubated (37° C., 2 h) with gentle mixing on a rotating wheel (9 rpm). Heparin lyase III (5 µl; 5 mIU) was added to the digests and incubated for a further 1 h (as above). Heparin lyase II (5 µl; 5 mIU) was added and the digests were incubated as above, for 18 h. Finally, aliquots (5 µl; 5 mIU) of all three heparin lyases were added simultaneously and the digests were incubated for a further 24 h. The enzyme digestion was terminated by heating (100° C., 5 min). All three HS samples were digested in duplicate and analysed by HPLC with UV detection (232 nm).

HPLC-SEC-RI of Digested HS Samples

The HPLC-SEC chromatograms were obtained using two Superdex™ Peptide 10/300 GL columns (300×10 mm, GE Healthcare) in series, on a Waters 2690 Alliance system with a Waters 2410 refractive index detector (range 64). The dn/dc for quantification from the RI was set at 0.129 (39). Samples (2 mg/ml) were injected (50 µl; 100 µg) and eluted with 50 mM ammonium acetate (0.5 ml/min) at room temperature. Heparin oligosaccharide standards (Iduron and Dextra Laboratories) were run under the same conditions. Run times for these columns were 120 min. Data was collected and analysed using DAWN Astra software (Version 4.73.04, Wyatt Technology Corp).

Disaccharide Compositional Analysis by HPLC

Twelve disaccharide standards, derived from the digestion of high-grade porcine heparin by bacterial heparinases, were purchased from Iduron. A stock solution of each disaccharide standard was prepared by dissolving the disaccharide in water (1 mg/ml). To determine the calibration curves for the disaccharide standards, a standard mix containing 20 µg/ml of each of the disaccharides was prepared from the stock solutions. From this twelve disaccharide standard mix a dilution series containing 20, 10, 5, 2.5, 1.25, 0.625 and 0.3125 µg/ml of each disaccharide was prepared. The $HS^{PM}$, $HS16^{+ve}$ and $HS16^{-ve}$ digests (2 mg/ml) were diluted with water to give 100 µg/ml solutions and then filtered using hydrophilic PTFE disposable syringe filter units (0.2 µm, 13 mm, Advantec). The HPLC separation conditions were based on those of Skidmore et al. (41). The analyses were performed on an Agilent 1260 Infinity liquid chromatography system (Agilent Technologies) with an Agilent 1260 MWD VL detector monitored at 232 nm. HS-derived disaccharides were separated on a ProPac™ PA1 column (Thermo Scientific, 4 mm×250 mm) with a guard column. Gradient elution was performed using a binary solvent system. Eluent A was water at pH 3.5 (adjusted using HCl), and eluent B was 2 M NaCl at pH 3.5 (adjusted with HCl). The gradient program was as follows: 100% A from 0-1 min, then 0-35% B from 1-32 min, then 35-65% B from 32-47 min, then 100% B from 47-57 min, then 100% A from 57-60 min. The injection volume was 50 µl. The column was eluted at a flow rate of 1.0 ml/min and maintained at 40° C. Disaccharides present in the HS digests were identified from their elution times by comparison with the elution times of the disaccharides in the twelve disaccharide standard mixes. HS16+ and HS16− digests were injected twice per duplicate digest (4 injections in total), while $HS^{PM}$ samples were injected once per duplicate digest (2 injections in total).

Plasmin Digestion

In order to determine the ability of the various GAGs to protect TGF-β1 from proteolytic digestion, TGF-β1 (100 ng) was pre-incubated with either 10 µg of Hep, $HS^{PM}$, $HS16^{+ve}$ or $HS16^{-ve}$ or alone in PBS at room temperature for 10 min. Plasmin digestion was carried out by adding 0.5 mU of plasmin to the TGF-β1 samples and incubating them at 37° C. for 1.5 h. Samples were subsequently run on a 4-12% SDS-PAGE gel and visualized by silver staining. All samples were made up to a final volume of 10 µl in PBS.

Alkaline Phosphatase (ALP) Assay

To determine the effect of HS16+ve on BMP-2 activity, C2C12 mouse myoblasts were seeded in duplicate at 20,000 cells/cm2 in complete C2C12 medium (DMEM-LG, 10% (v/v) FCS, 100 U/mL penicillin and 100 µg/mL streptomycin) and allowed to attach for 24 h. The complete medium was then replaced with treatment medium (DMEM-LG, 5% (v/v) FCS, 100 U/mL penicillin and 100 µg/mL streptomycin) with or without 100 ng/mL BMP-2 and/or 5 µg/mL HS16+ve, HS3+ve or HSPM and the cells incubated for 3 days. Total cell lysate was then collected in RIPA buffer containing a protease inhibitor cocktail (Calbiochem, Merck Millipore, MA, USA) and protein content determined using a BCA protein assay kit (Thermo Fisher Scientific). ALP activity was measured by incubating 5 µg of protein with p-nitrophenyl phosphate (Sigma-Aldrich) for 1 h at 37° C. and reading the change in absorbance at 405 nm. RIPA buffer alone and 1 µL (10,000 U/mL) of calf intestinal phosphatase (New England Biolabs Ltd, Ontario, Canada) were used as negative and positive controls respectively. Each sample was read in duplicate to give a total of 4 readings per treatment group.

Heparinase Treatment of hMSCs

To assess the influence of endogenous HS on TGF-β1 signalling, hMSCs were seeded at a density of 7,500 cells/cm² in 12-well plates in basal medium and allowed to attach overnight. A combination of heparinase I, II and III (1.2 mIU/mL of each) was then added to the media in each well and incubated for 24 h. The cells were then exposed for 6 h to TGF-β1 treatments, prepared at either 1 ng/mL or 5 ng/mL alone or pre-incubated for 10 min at room temperature with either 10 µg/mL or 40 µg/mL of full length heparin, and then lysed for immunoblotting in 2× Laemmli buffer. Treatments were prepared in serum-free medium (DMEM-LG supplemented with 100 U/mL penicillin, 100 µg/mL streptomycin and 2 mM L-glutamine) to avoid increasing the background levels of pSMAD seen when fresh serum is added to cells.

Immunofluorescence Staining of Heparinase-Digested Cells

To ensure that the heparinase treatment effectively removed endogenous HS chains from hMSCs, cells were seeded in 8-well chamber slides at a density of 3,500 cells/cm² in basal medium. Cells were allowed to attach overnight before being treated with a combination of heparinase I, II and III (1.2 mIU/mL each), added directly to each well, for 24 h. Subsequently, cells were fixed in 4% (w/v) paraformaldehyde in PBS for 10 min at room temperature, blocked with 3% (w/v) bovine serum albumin (BSA) in PBS for 30 min at room temperature and then incubated with the anti-HS 10E4 antibody (1:25 dilution in 0.3% (w/v) BSA-PBS) (AMS Biotechnology, Abingdon, UK) for 3 h at room temperature. Cells were then incubated with an anti-mouse IgM-FITC antibody (1:500 dilution in 0.3% (w/v) BSAPBS) (BD Pharmingen™, Becton, Dickinson and Company, NJ, USA) for 45 min at room temperature and the nuclei stained with Hoechst 33342 (2 µg/mL in PBS) (Life Technologies) for 10 min at room temperature. Samples were imaged on an Olympus IX-81.

Results

Heparin Binds to TGF-β1 and Potentiates its Activity

Figure 1B:
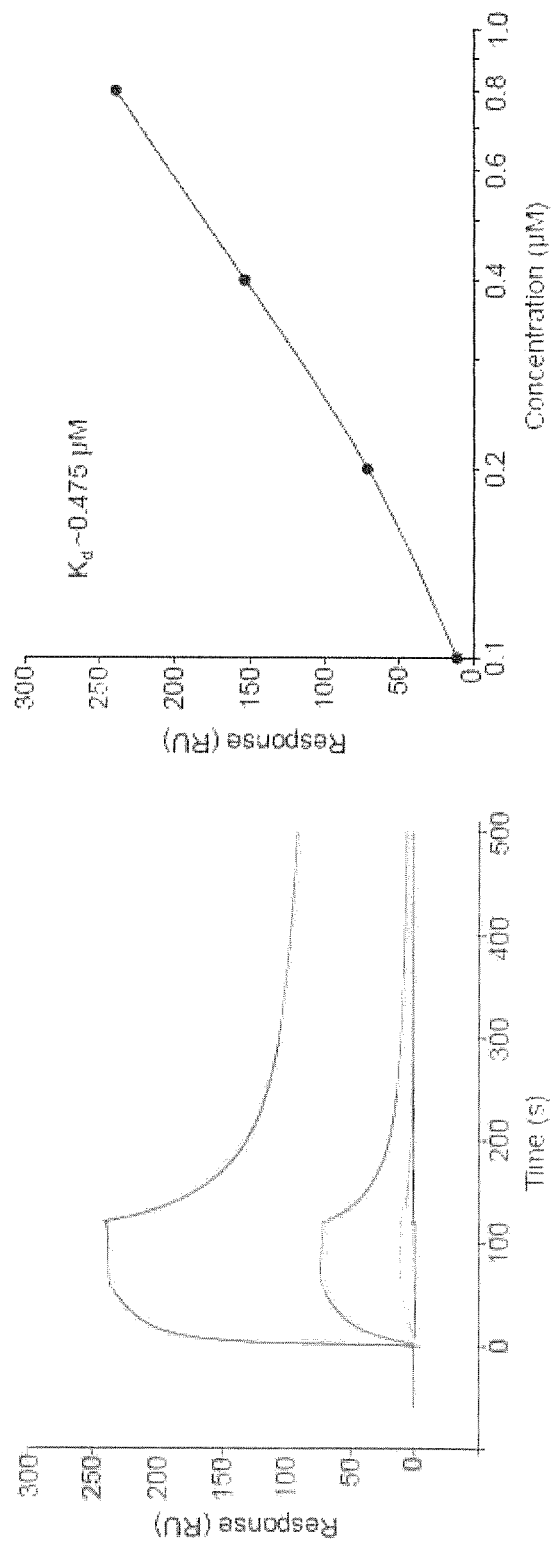
Figure 2A:
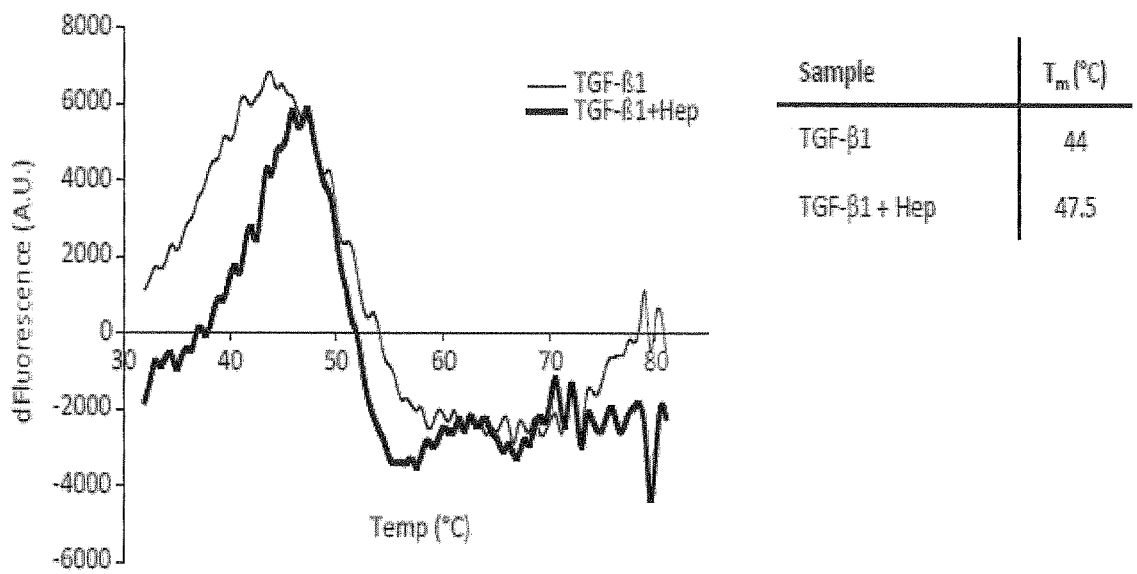
FIGS. 2A to 2D. Heparin binding potentiates TGF-β1 activity. (A) Chart showing first derivative of melting curves obtained from DSF of TGF-β1 (2.5 μM) and DTT (10 mM) with (TGF-β1+Hep) or without heparin (25 μM)(TGF-β1). Melting temperature of TGF-β1 under each condition was taken at the peak of each graph. (B) Western blot and chart showing relative protein levels: Cells were treated with TGF-β1 (1 or 5 ng/ml), pre-incubated with various amounts (0, 10 or 40 μg/ml) of heparin (Hep) for 10 min at room temperature, and lysed after 6 h. Phosphorylated SMAD2 (pSMAD2) and SMAD3 (pSMAD3), total SMAD2/3 and actin levels were determined by Western blotting and quantified by densitometry relative to actin. Error bars represent standard deviation, n=3. (C) Charts showing results of quantitative PCR of SOX9 and COMP in chondrogenic micromass pellets cultured for 3 days in chondrogenic media (Media) or chondrogenic media with heparin (10 μg/ml) (Media+Hep). Error bars represent standard error, n=3. (D) Charts showing inhibition of SOX9 and COMP expression in day 3 chondrogenic micromass pellets, as measured by qPCR, after treatment with DMSO or SB431542 (10 μM). Error bars represent standard error, n=3.

In order to determine the effects of heparin on TGF-β1 signaling, we first set out to ensure that heparin was able to bind to TGF-β1. Both SPR and GAG-binding plate assays demonstrated that TGF-β1 bound in a dose-dependent manner to heparin that had been either immobilized in a 96-well plate (FIG. 1A), or biotinylated and immobilized on a Biacore SA-chip, respectively (FIG. 1B). Our data indicate that TGF-β1 binds to heparin with an approximate $K_d$ of ~0.475 µM (FIG. 1B). This binding to heparin afforded TGF-β1 an enhanced thermal stability, as determined by DSF (FIG. 2A). The TGF-β1 homodimer encompasses 9 disulfide bonds, 4 intra-chain and 1 inter-chain, which confer it with a high degree of thermal stability. This was demonstrated with the high melting temperature of 66° C. observed for TGF-β1 alone (data not shown). As we were testing the premise that the binding of heparin to TGF-β1 would further increase its thermal stability through the introduction of new, non-covalent, intermolecular bonds, it became necessary to reduce the melting temperature of the protein to levels that the assay could detect. This was achieved through the addition of 10 mM of DTT to the reaction, which reduced the disulfide bonds within the protein, thereby lowering its thermal stability. This resulted in a shift in the melting temperature of TGF-β1 from 66° C. to 44° C. Upon the addition of heparin, the peak representing the melting temperature of TGF-β1 was seen to shift to the right and the protein's melting temperature increased to 47.5° C.

Figure 2B:
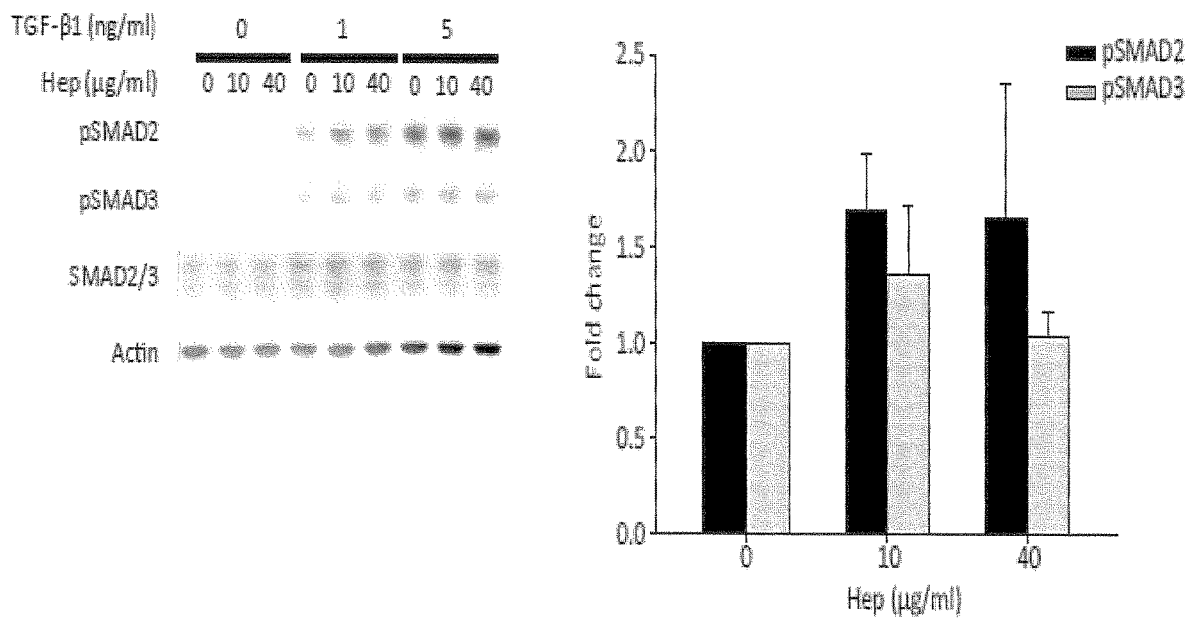

The next step was to determine if the interaction between heparin and TGF-β1 was influencing the TGF-β1 signaling pathway. To accomplish this, hMSCs were treated with varying amounts of heparin and TGF-β1, and protein harvested at 1, 6 and 24 h post-treatment in order to examine the levels of pSMAD2 and pSMAD3 (FIG. 2B). At 1 h post treatment, both pSMAD2 and pSMAD3 levels were saturated in all cells treated with TGF-β1 and heparin (data not shown). No discernible levels of pSMAD2 and pSMAD3 were observed in any cells treated with heparin alone, demonstrating that heparin by itself is unable to activate the TGF-β1 signaling pathway. At 6 h post-treatment, the pSMAD levels in all cells had started to subside. However, cells that had been treated with both heparin and TGF-β1 displayed levels of pSMAD2 and pSMAD3 that were ~1.6 and ~1.35 fold, respectively, higher than cells that had been treated with the equivalent dose of TGF-β1 without heparin (FIG. 2B). Similarly, pSMAD levels at 24 h continued to be greater in cells that had been treated with both heparin and TGF-β1 than cells treated with TGF-β1 alone (data not shown). The data demonstrate firstly that higher doses of TGF-β1 (5 ng/ml versus 1 ng/ml) produced pSMAD signals that were sustained for longer periods of time. Secondly, they also indicate that heparin is able to prolong the half-life of the pSMAD signals beyond that normally observed for the growth factor alone.

Figure 2C:
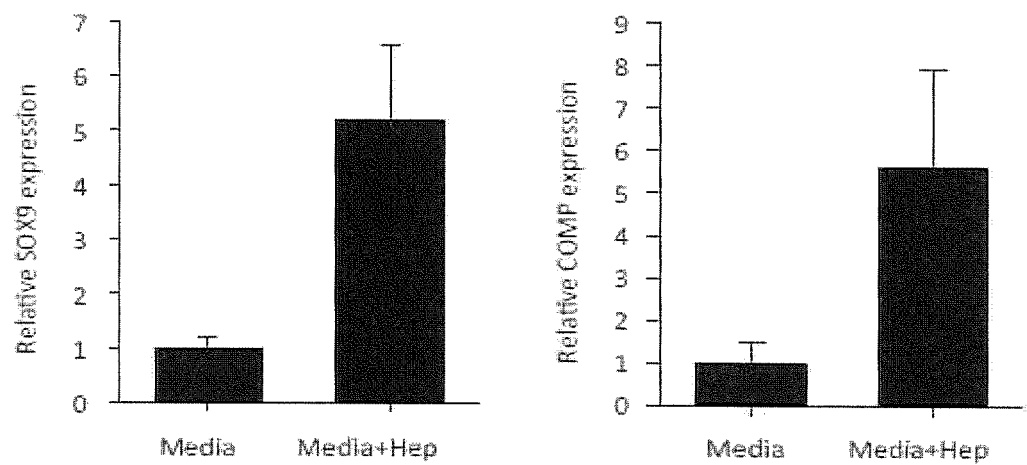
Figure 2D:
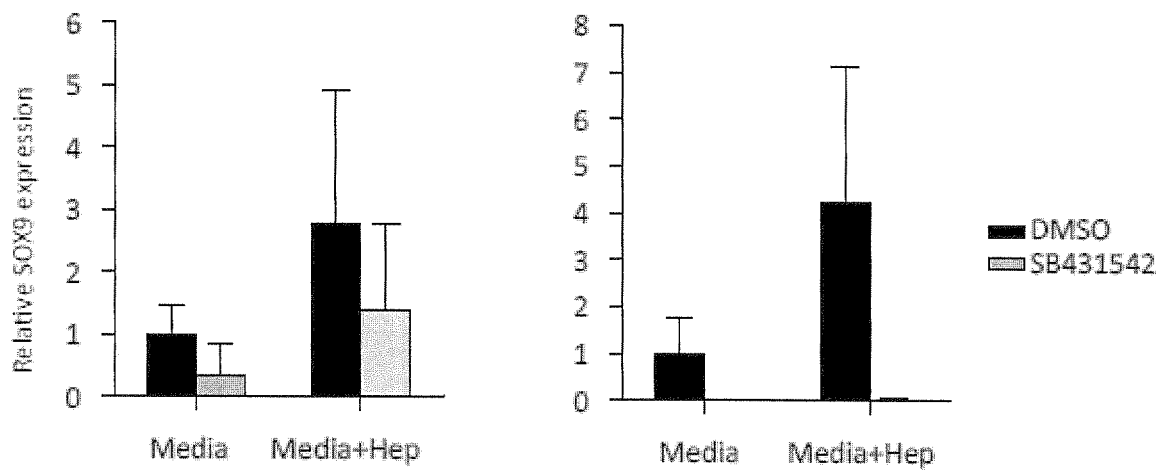

To further investigate this effect, we proceeded to examine the transcript levels of TGF-β1 target genes expressed during the early stages of the chondrogenic differentiation of hMSCs. Chondrogenic differentiation of the hMSCs was carried out in the presence of either Media (TGF-β1 alone) or Media+Hep (TGF-β1+Heparin). After 3 days of culture in chondrogenic media, the micromass pellets cultured in Media+Hep displayed ~5-fold higher levels of both SOX9 and COMP mRNA transcripts (FIG. 2C). Taken together, the data suggest that heparin is able to bind to TGF-β1 and that such binding potentiates the TGF-β1 signal seen in the cells. Having established that heparin was indeed potentiating the activity of TGF-β1, we next sought to rule out the possibility that heparin was producing these effects via some indirect pathway, rather than through the TGF-β1 signaling pathway. To do so, SB431542, a TGF-β type I receptor inhibitor was employed (42). Treatment of hMSCs with SB431542 led to a reduction in both SOX9 and COMP gene expression in 3-day old chondrogenic micromass pellets (FIG. 2D). The data suggests that the inhibition of TGF-β1 activity at the receptor level negates the TGF-β1-potentiating effects of heparin, again implying that heparin exerts its effects on TGF-β1 activity through the modulation of TGF-β1 signaling.

Heparin Length Requirements for TGF-β1 Binding and Activity

Figure 3A:
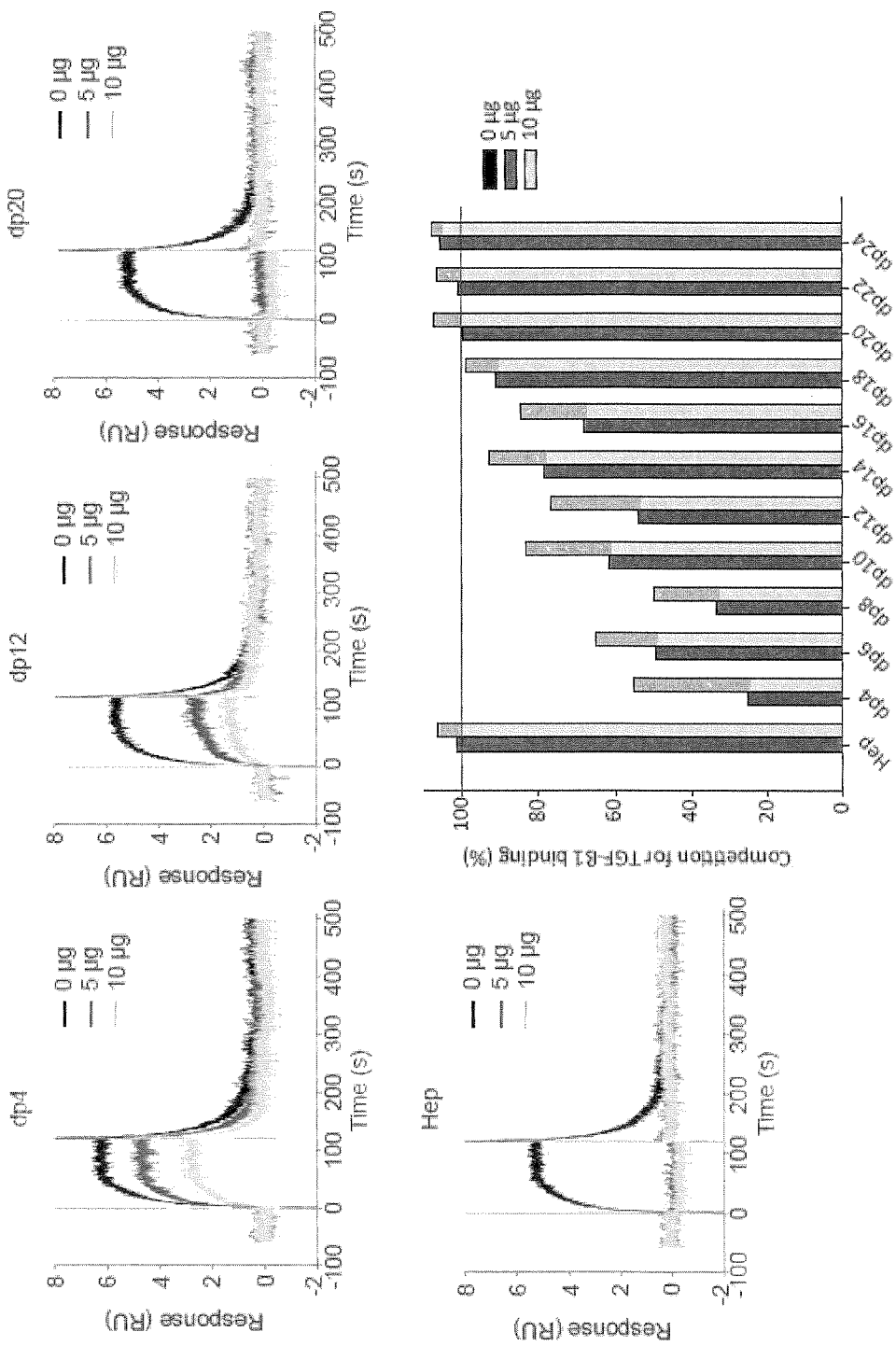
FIGS. 3A to 3C. Heparin length requirements for TGF-β1 binding and activity. (A) Representative SPR sensograms showing the changes in binding response of 200 nM of TGF-β1 when pre-incubated with either 5 or 10 μg of heparin (Hap) or size fractionated heparin (dp4 to 24) prior to injection. Representative bar chart showing the ability of the various GAGs to compete for TGF-β1 binding against the heparin coated chip. Data were normalized to 200 nM TGF-β1 alone. (B) Chart showing results of GAG-binding plate assay to determine ability of TGF-β1 to bind to various heparin fragments (dp14-24) or unfractionated heparin (Hep). Error bars represent standard deviation, n=3. (C) Western blots: Cells were treated with TGF-β1 (1 ng/ml), pre-incubated with 10 μg/ml of the various heparin fragments (dp14-24) or unfractionated heparin (Hep) for 10 min at room temperature, and lysed at 6 h. Phosphorylated SMAD2 (pSIVIAD2) and SMAD3 (pSMAD3), total SMAD2/3 and actin levels were determined by Western blotting.
Figure 3B:
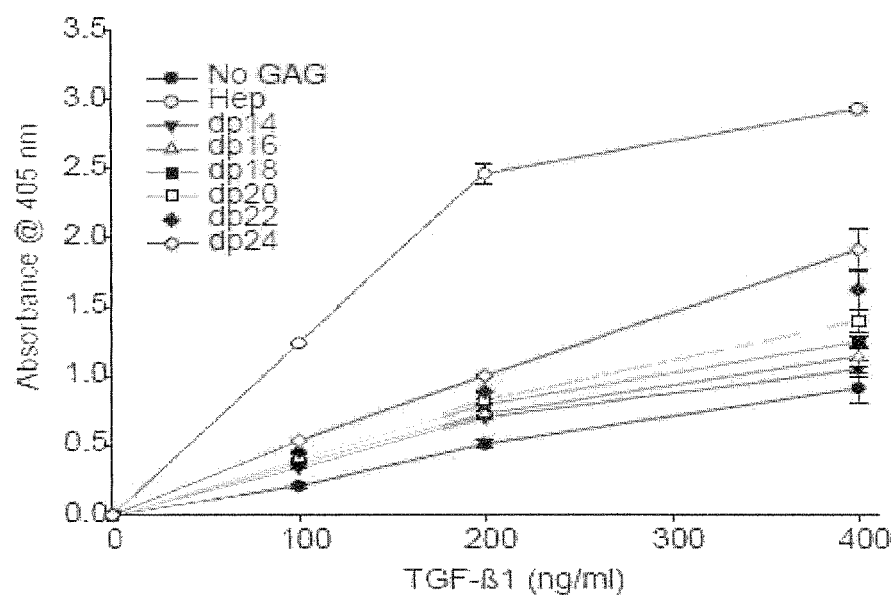
Figure 3C:
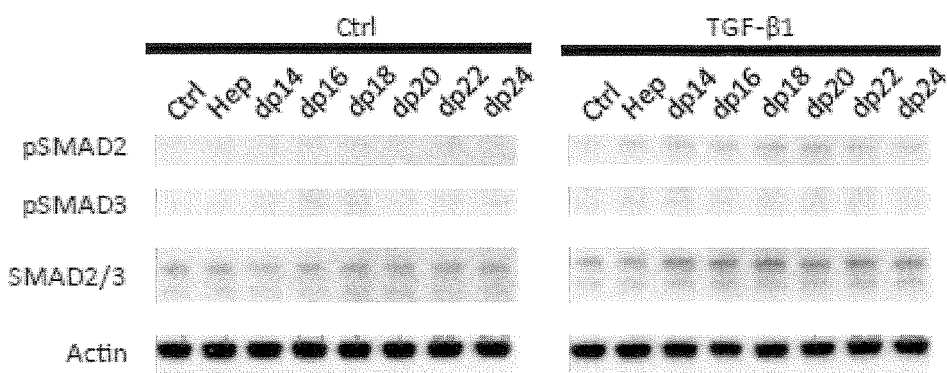

We next sought to determine the minimum length of heparin needed to bind to TGF-β1. The ability of soluble size-fractionated heparin fragments (dp4 to dp24) to competitively inhibit the binding of TGF-β1 to a heparin coated SA-chip increased in proportion to their length (FIG. 3A). This increase in TGF-β1 binding ability appeared to plateau from dp18 onwards, with competition levels similar to those seen for unfractionated, full length heparin (Hep). The results obtained from GAG-binding plate assays also indicated that TGF-β1 binding to heparin improved as the length of the heparin chain increased from 14 (dp14) to 24 (dp24) saccharide units (FIG. 3B). Heparin chains that were shorter than dp14 (i.e. dp4-12) were unable to bind TGF-β1 effectively (data not shown). Western blot analysis of pSMAD2 and pSMAD3 levels in cells treated with varying lengths of heparin fragments and TGF-β1 at 1 h post treatment showed saturation of both pSMAD signals (data not shown). However, at 6 h post treatment, we were expecting to observe a length-dependent increase in the potentiating activity of the various (dp14-24) heparin fragments, with an expected maximum pSMAD signal with a dp24-TGF-β1 combination, albeit still lower than that observed in cells treated with unfractionated heparin (Hep) and TGF-β1. Instead we observed that cells that had been treated with TGF-β1 and heparin fragments between dp18 and dp22 displayed pSMAD levels greater than those observed in cells treated with unfractionated heparin and TGF-β1, with signals peaking with a dp20-TGF-β1 combination (FIG. 3C). This suggests that the length of the heparin chain exerts considerable influence over its ability to potentiate the TGF-β1 signal.

Heparin Sulfation Requirements for TGF-β1 Binding and Activity

Figure 4A:
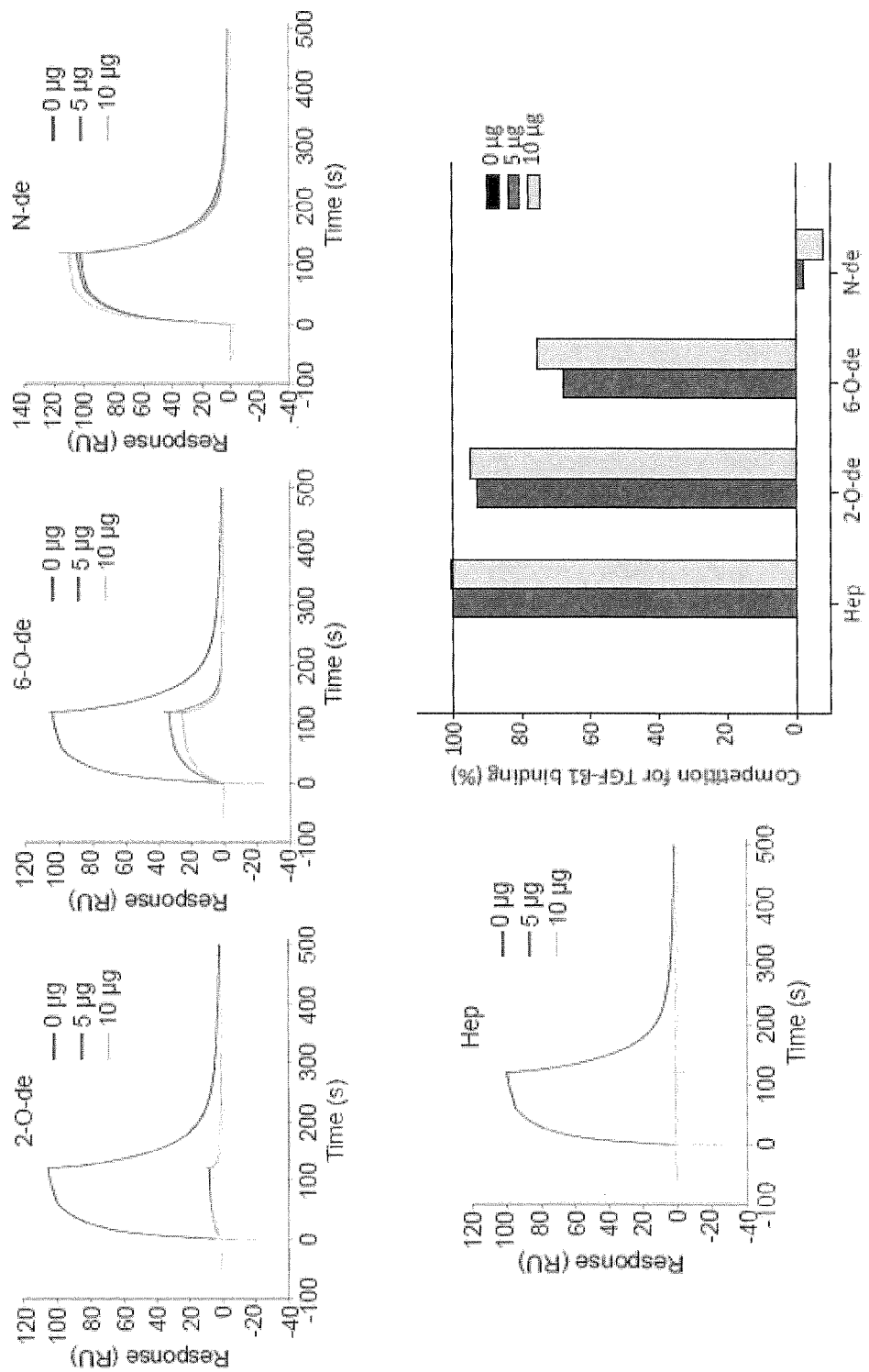
FIGS. 4A to 4C. Heparin sulfation requirements for TGF-β1 binding and activity. (A) Representative SPR sensograms showing the changes in binding response of 200 nM of TGF-β1 when pre-incubated with either 5 or 10 μg of heparin (Hep), 2-O-desulfated heparin (2-O-de), 6-O-desulfated heparin (6-O-de) or N-desulfated heparin (N-de) prior to injection. Representative bar chart showing the ability of the various GAGs to compete for TGF-β1 binding against the heparin coated chip. Data were normalized to 200 nM TGF-β1 alone. (B) Chart showing GAG-binding plate assay to determine ability of TGF-β1 to bind to selectively desulfated (2-O-de, 6-O-de or N-de) or fully sulfated heparin (Hep). Error bars represent standard deviation, n=3. (C) Western blots: Cells were treated with TGF-β1 (1 ng/ml), pre-incubated with 10 μg/ml of the various selectively desulfated (2-O-de, 6-O-de or N-de) or fully sulfated heparin (Hep) for 10 min at room temperature, and lysed at 6 h. Phosphorylated SMAD2 (pSMAD2) and SMAD3 (pSMAD3), total SMAD2/3 and actin levels were determined by Western blotting.
Figure 4B:
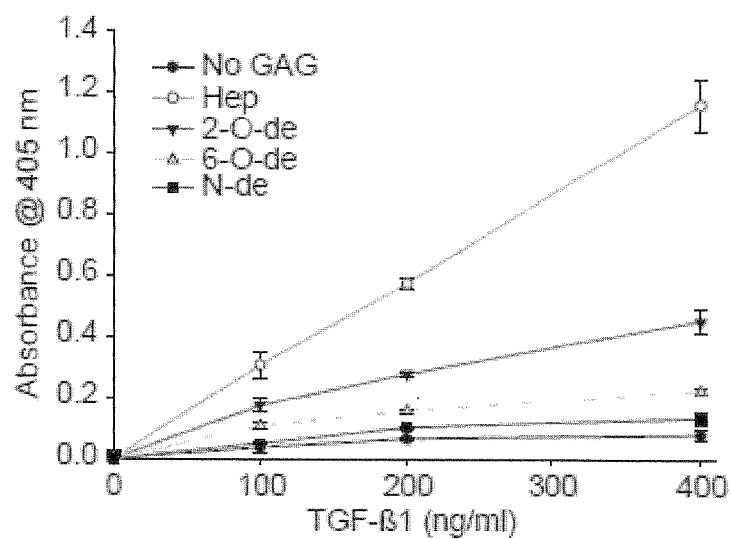

Given the predominantly ionic nature of heparin-protein interactions, we next set out to examine the influence that the various sulfate groups in heparin have over the interaction between it and TGF-β1. Biacore competition assays indicated that the loss of 2-O sulfate groups from heparin (2-O-de) had a minimal effect on its ability to competitively inhibit TGF-β1 binding to immobilized heparin (FIG. 4A). The loss of 6-O sulfate groups (6-O-de) led to a loss of approximately 40% of TGF-β1-binding ability, while the loss of N-sulfate groups abrogated heparin's ability to bind TGF-β1. In contrast, GAG-binding plate assays demonstrated that the removal of 2-O sulfate groups from heparin (2-O-de) reduced TGF-β1 binding by about 60% compared to fully sulfated, full-length heparin (Hep) (FIG. 4B). The removal of 6-O sulfate groups (6-O-de) reduced TGF-β1's ability by approximately 80% and the lack of N-sulfation (N-de) again essentially abolished TGF-β1 binding. Interestingly, when tested in cell culture, the results obtained were as variable as those seen when assessing the various heparin lengths. Instead of the reduction we expected to see in the pSMAD levels of cells treated with 2-O-desulfated heparin (2-O) for 6 h, relative to fully sulfated heparin we observed an increase to levels beyond those seen in heparin-treated cells (FIG. 4C), suggesting that 2-O-desulfated heparin potentiated TGF-β1 signaling even more than fully sulfated heparin. Similarly, the removal of 6-O-sulfation (6-O) also brought about a stabilization of pSMAD levels relative to those seen in heparin-treated cells. The loss of N-sulfation (N) however, did not lead to an increase in pSMAD levels relative to those of heparin-treated cells.

Collectively, the data indicate that the loss of 2-O-sulfation from heparin, and to a lesser degree 6-O-sulfation, actually improves the ability of heparin to potentiate the TGF-β1 signal, suggesting that the relationship between binding strength and bioactivity is not linear.

Identification of TGF-β1 Heparin Binding Sites

As heparin is known to interact with configurations of basic residues present in numerous, susceptible growth factors, our next goal was to identify the actual heparin-binding site(s) within TGF-β1. Previous studies that identified putative heparin-binding sites on TGF-β1 did so through the identification of heparin-binding motifs present in the linear protein sequence (2,4). However, such an approach fails to take into consideration the full 3-dimensional (3D) conformational nature of proteins, and thus fails to identify heparin-binding sites that may only be apparent from the tertiary structure of the protein. As such, we decided to employ the Protect-and-Label strategy developed by Ori et al. (37) to determine if such 3D sites were present Isolation of Affinity Selected TGF-β1-Binding HS (HS16$^{+ve}$)

Having identified the structural features and requirements of heparin-TGF-β1 interactions, our next goal was to isolate a TGF-β1-binding fraction of HS from the heterogeneous pool that constitutes commercially available HS$^{PM}$ preparations. To do so, we first designed a heparin-binding peptide derived from TGF-β1 (FIG. 6A) and tested its ability to bind to $^3$H-heparin (FIG. 6B). The TGF-β1 peptide was then used to isolate a TGF-β1-binding population of HS using our HS affinity isolation platform, as previously described by Murali et al. (29). HS that did not bind to the column was termed HS16$^{-ve}$, while the TGF-β1-binding HS that eluted from the column with 1.5 M NaCl was termed HS16$^{+ve}$ (FIG. 6C).

TABLE 1

Summary of peptides identified by Protect and Label structure proteomics.
Labeled peptides were identified by tandem mass spectrometry and analyzed by Mascot search Version 2.3 (Matrix Science). Here, a summary of the peptides involved in the heparin-binding sites and the labeled position is provided.

| Peptide | Sequence | Residues[a] | SEQ ID NO. |
|---|---|---|---|
| 1 | C(carbamidomethyl)FSSTEK(biotin)NC(carbamidomethyl)C(carbamidomethyl)VRQLY | 7-21 | 8 |
| 2 | IDFRK(biotin)DLGW | 22-30 | 9 |
| 3 | RK(biotin)DLGWK(acetyl)W | 25-32 | 10 |
| 4 | RK(acetyl)DLGWK(biotin)W | 25-32 | 10 |
| 5 | IHEPK(biotin)GY | 33-39 | 11 |
| 6 | SLDTQYSK(biotin)VL | 53-62 | 12 |
| 7 | YVGRK(biotin)PK(acetyl)VEQL | 91-101 | 13 |
| 8 | YVGRK(acetyl)PK(biotin)VEQL | 91-101 | 13 |
| 9 | SNMIVRSC(carbamidomethyl)K(biotin)C(carbamidomethyl)S | 102-112 | 14 |

Figures 5A, 5B:
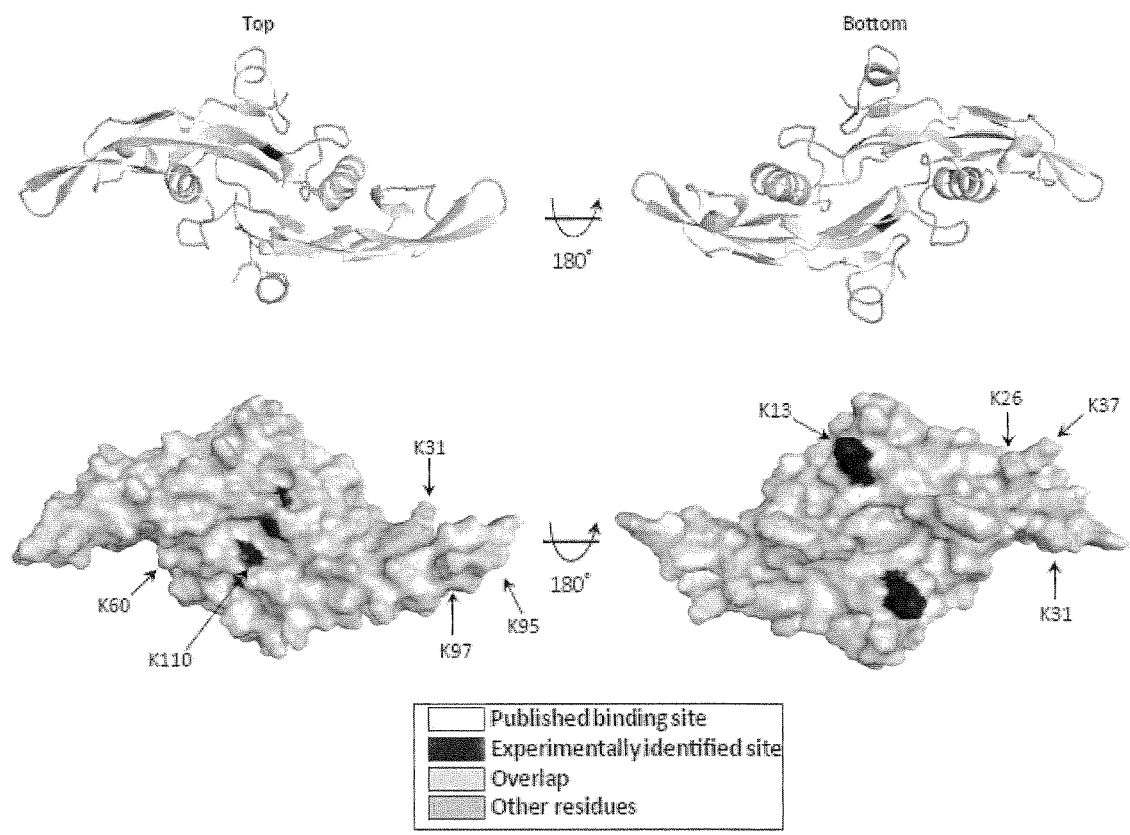
FIGS. 5A and 5B. Identification of TGF-β1 heparin-binding sites. (A) TGF-β1 amino acid sequence and position of lysines identified by the Protect-and-Label strategy [SEQ ID NO:3]. Previously published heparin-binding domain (HBD) of TGF-β1 is underlined. Lysines identified with high confidence (*) and medium confidence (^) are indicated. (B) Position of identified lysines mapped onto the predicted 3-dimensional structure of TGF-β1 (PDB: 1KLC [51]). Top row, ribbon diagram. Bottom row, corresponding molecular surface. Left column and right column, 180° rotation of TGF-β1 around the horizontal axis.

[a]Residue numbering according to FIG. 5A within TGF-β1. Our analysis identified 8 lysines (K13, K26, K31, K37, K60, K95, K97 and K110) that appear to be involved in the binding of TGF-β1 to heparin (FIG. 5A, Table 1). Of these 8, 7 were identified with a high level of confidence based on the MS/MS sequencing. The remaining lysine, K60, was identified with a medium level of confidence, suggesting that its interaction with heparin is intermittent and may not be essential for TGF-β1's binding to heparin, so supporting also the current binding model proposed by Lyon et al. (2).

All but two of the identified lysines, K13 and K110, have been previously identified as part of TGF-β1's heparin-binding domains (FIG. 5A). When mapped onto the 3D structure, K13 maps onto the same bottom surface as K26, which has been proposed to be an essential residue for heparin binding (FIG. 5B). K110 maps along the interface between the TGF-β1 monomers. However, K110 appears to be embedded within the protein, so it is likely that this result is a false-positive, as the "sticky" nature of TGF-β1 necessitated the use of an acid-sensitive detergent (RapiGest™ SF Surfactant), rather than 2 M NaCl, to elute the protein from the heparin mini-column. The use of this detergent to elute results in the denaturing of the protein prior to the labelling/biotinylation step, so that residues that are normally embedded within the protein core are exposed only to be erroneously labelled.

Figure 7A:
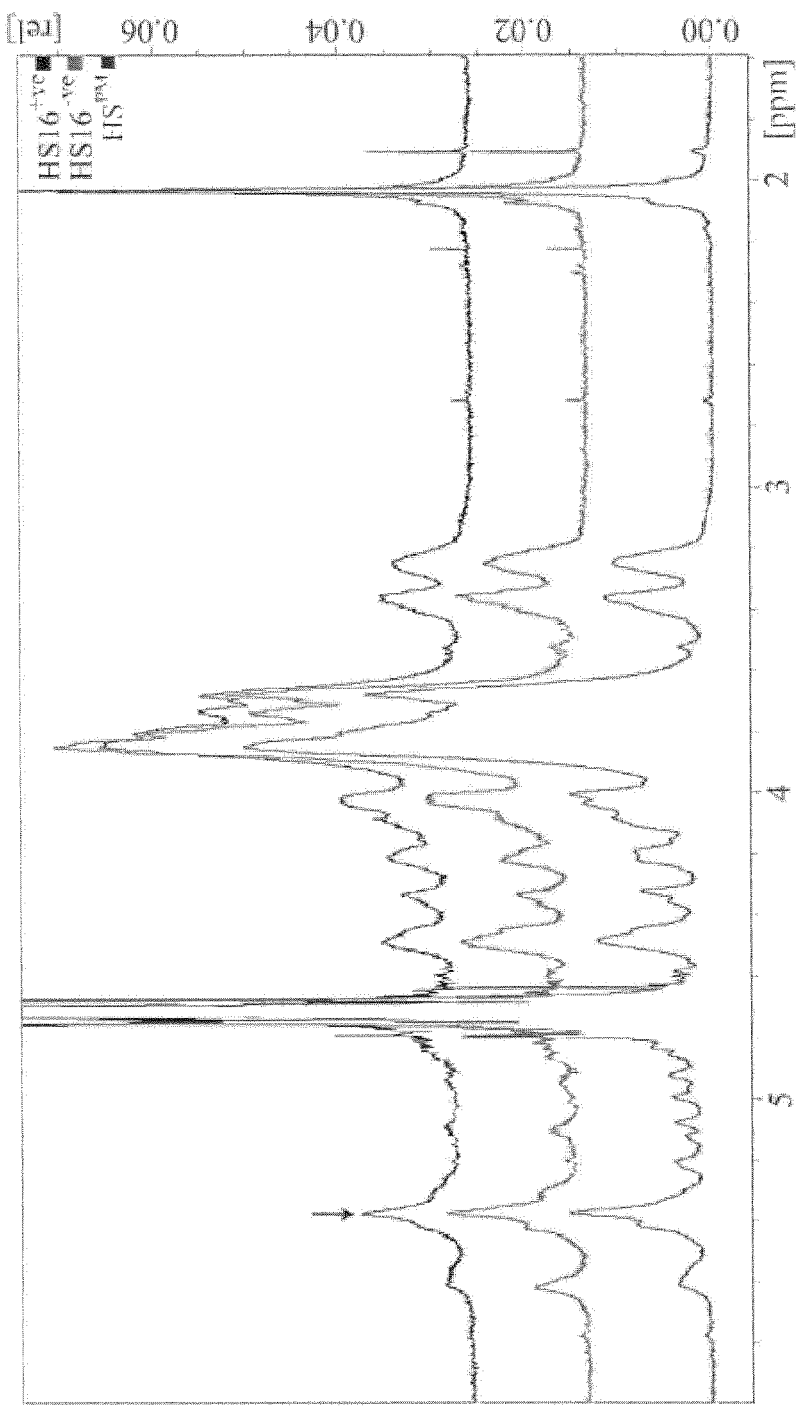
FIG. 7A to 7C. Characterization of HS16$^{+ve}$. (A) Proton NMR spectra of HS16$^{+ve}$ (top), HS16$^{-ve}$ (middle) and HS$^{PM}$ (bottom). Arrow indicate difference in the spectra between the three sugars. (B) Size exclusion chromatogram of HS16$^{+ve}$, HS16$^{-ve}$ and HS$^{PM}$. Elution times of the heparin size standards (dp8, 12, 20 and 26) are indicated on the graph. (C) Chart showing disaccharide composition of heparin lyase digested HS16$^{+ve}$, HS16$^{-ve}$ and HS$^{PM}$.
Figure 7B:
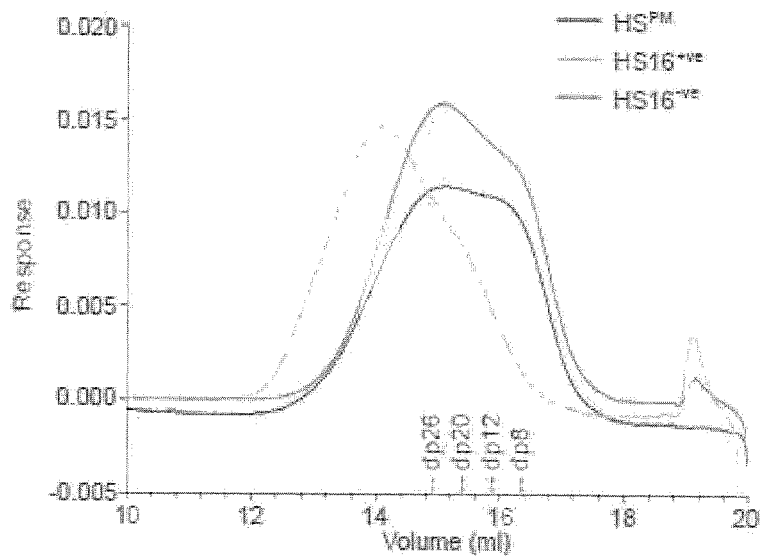

Proton NMR, HPLC-SEC-RI and disaccharide compositional analyses were then carried out to determine if there were any systematic differences between HS$^{PM}$, HS16$^{+ve}$ and HS16$^{-ve}$. NMR analysis of the three HS samples revealed several subtle differences (arrows, FIG. 7A), while chromatograms from SEC indicated that HS16$^{+ve}$ was predominantly composed of HS chains that were consistently larger than those seen in HS$^{PM}$ and HS16$^{-ve}$ (FIG. 7B).

The most notable difference in the NMR spectra of the three HS samples was the slight decrease in signal intensity at ~5.4 ppm of HS16+ve (arrow, FIG. 7A), which was assigned to the glucosamine acetates methyl resonance, as previously reported by Guerrini et al. [*Complex glycosaminoglycans: profiling substitution patterns by two-dimensional nuclear magnetic resonance spectroscopy.* Anal Biochem, 2005. 337(1): p. 35-47.]. This decrease was indicative of a slightly higher level of N-sulphation in HS16+ve compared to the other two fractions.

Figure 7C:
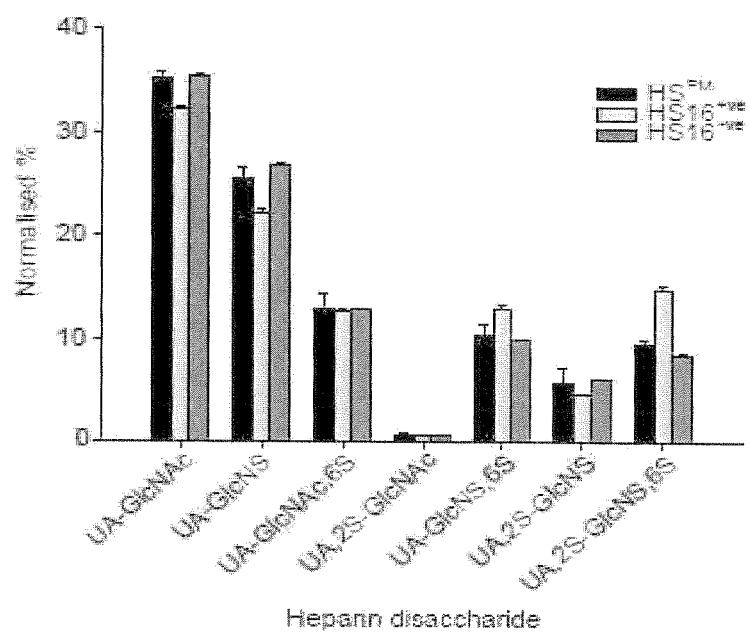

Based on the elution times of several heparin size standards (dp8, 12, 20 and 26), our data also indicate that HS16$^{+ve}$ is composed of HS chains that are longer than 26 saccharides. Finally, disaccharide compositional analysis of the three HS sample digests showed that although HS$^{PM}$ and HS16$^{-ve}$ were similar, HS16$^{+ve}$ was enriched in ΔUA-GlcNS,6S and ΔUA,2S-GlcNS,6S and contained less ΔUA-GlcNAc, ΔUA-GlcNS, ΔUA,2S-GlcNAc and ΔUA,2S-GlcNS (FIG. 7C, Table 2). Taken together, the data indicate that the pool of HS that makes up $HS16^{+ve}$ is markedly different from $HS16^{-ve}$ and $HS^{PM}$ with respect to both size distribution and composition. Additionally, the relative reduction in ΔUA,2S-GlcNAc and ΔUA,2S-GlcNS seen in HS16+ corroborated our earlier findings on how the loss of 2-O-sulfate from heparin actually increases its bioactivity towards TGF-β1 (FIG. 4).

HS chains are known to vary greatly in terms of chain length [Esko, J. D., K. Kimata, and U. Lindahl, *Proteoglycans and Sulfated Glycosaminoglycans, in Essentials of Glycobiology*, A. Varki, et al., Editors. 2009, Cold Spring Harbor Laboratory Press: Cold Spring Harbor, N.Y.], which partially explains their ability to bind to such a plethora of proteins. In order to enhance the relative specificity of an HS preparation for a given protein, it is necessary to reduce this variation. We examined the size distribution of polysaccharide chains within the three HS samples. Resolution of the three samples and heparin by native PAGE showed that HS16+ve was predominantly composed of longer HS chains compared to HS16−ve and HSPM. Heparin, which is comparatively more homogenous than HS, was used to give an appreciation of the high heterogeneity present in HS preparations. To validate these findings, size exclusion chromatography (HPLC-SEC-RI) was carried out. The chromatograms from SEC indicated that HS16+ve consists of a poly-disperse subset of the HSPM from approximately dp8 to >dp26 (FIG. 7B). However, the HS16+ve population is enriched in HS with longer chain lengths (>dp26), which corroborates our data from native PAGE and our findings on the length requirements for heparin to bind TGF-β1.

Figure 4C:
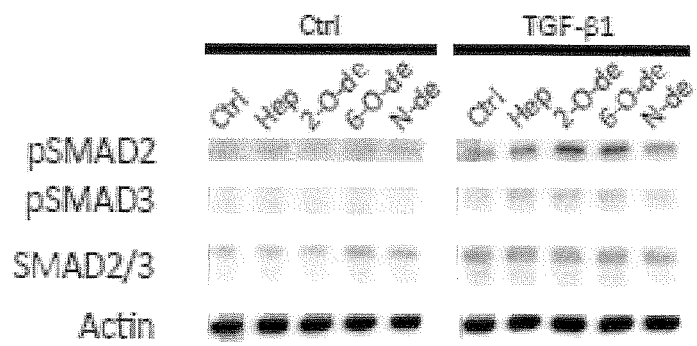
Figure 8A:
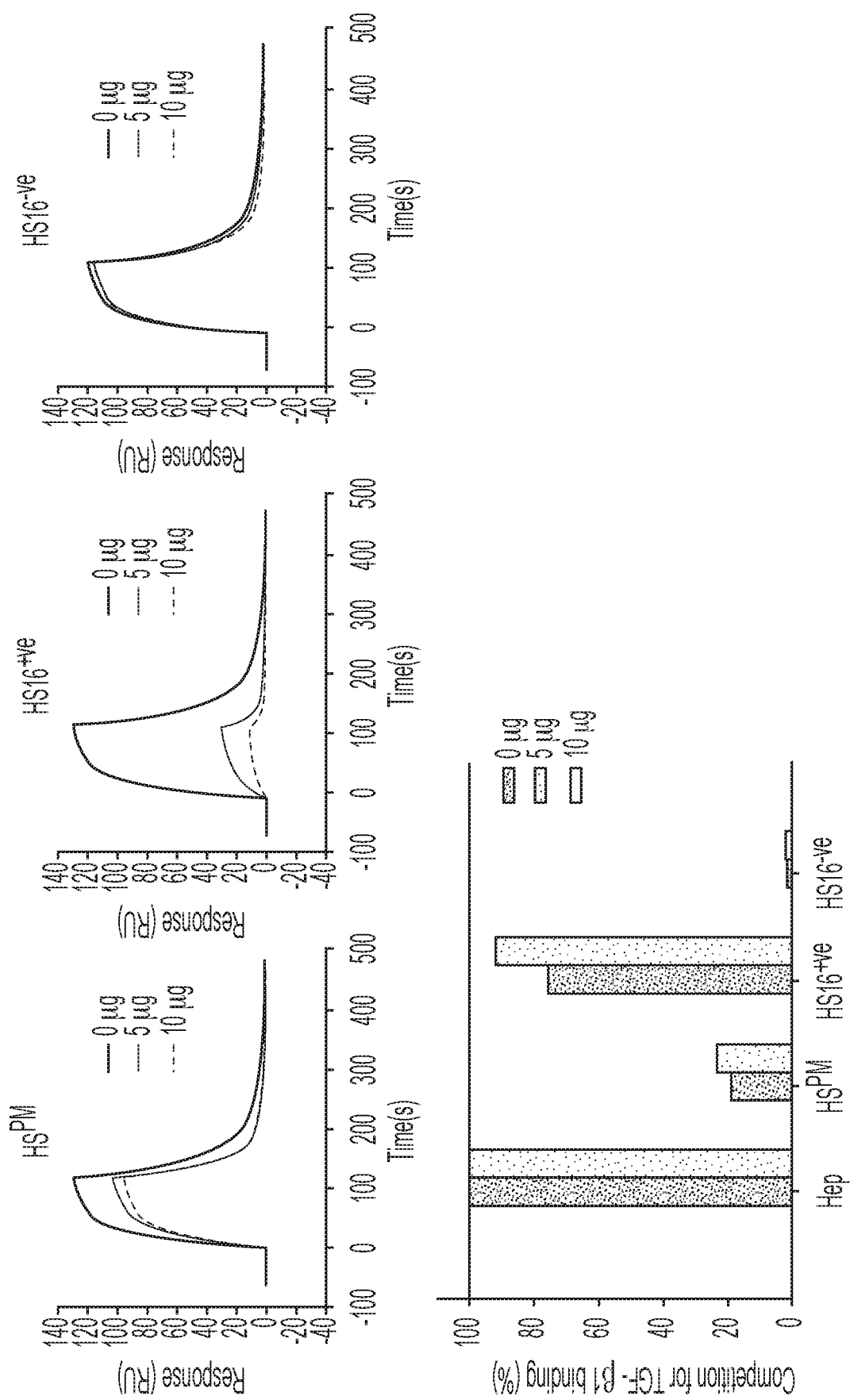
FIG. 8A to 8H. HS16$^{+ve}$ binds to and potentiates TGF-β1 signaling. (A) Representative SPR sensograms showing the changes in binding response of 200 nM of TGF-β1 when pre-incubated with either 5 or 10 μg of HS16$^{+ve}$, HS16$^{-ve}$ or HS$^{PM}$ prior to injection. Representative bar chart showing the ability of the various GAGs to compete for TGF-β1 binding against the heparin coated chip. Data were normalized to 200 nM TGF-β1 alone. (B) Representation of gel electrophoresis: Plasmin digestion of TGF-β1 incubated either alone or with the indicated GAGs. Samples were digested for 1.5 h, resolved on a 4-12% SDS-PAGE and visualized by silver staining. (C) Western blot: Cells were treated with TGF-β1 (1 ng/ml), pre-incubated with 10 μg/ml of heparin (Hep), $HS^{PM}$, $HS16^{+ve}$ or $HS16^{-ve}$ for 10 min at room temperature, and lysed at 6 h. Phosphorylated SMAD2 (pSMAD2) and SMAD3 (pSMAD3), total SMAD2/3 and actin levels were determined by Western blotting. Representative SPR sensograms showing the changes in binding response of 200 nM of TGF-β1 when pre-incubated with either 5 or 10 μg of (D) HSPM, (E) HS16+ve, (F) HS16-ve or (G) heparin (Hep) prior to injection. (H) Bar chart depicts the ability of the various GAGs to compete for TGF-β1 binding against the heparin-coated surface. For clarity, the binding response of TGF-β1 without any GAG (i.e. 0 μg) is only shown for heparin. Data were normalised to 200 nM TGF-β1 alone. Error bars represent standard deviation, n=3.
Figure 8B:
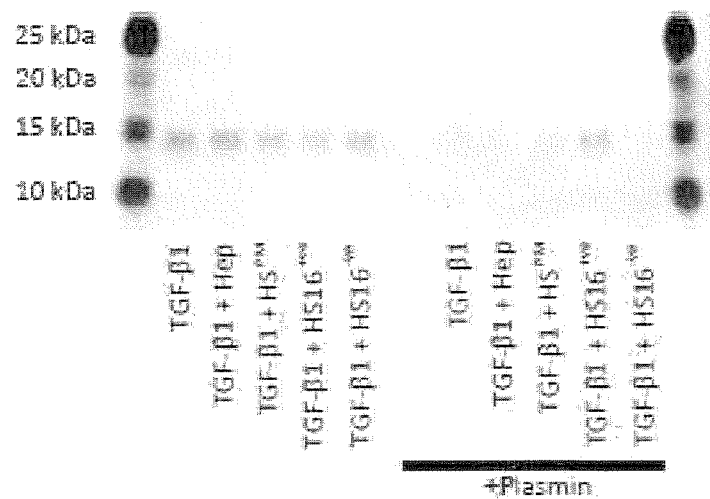
Figure 8C:
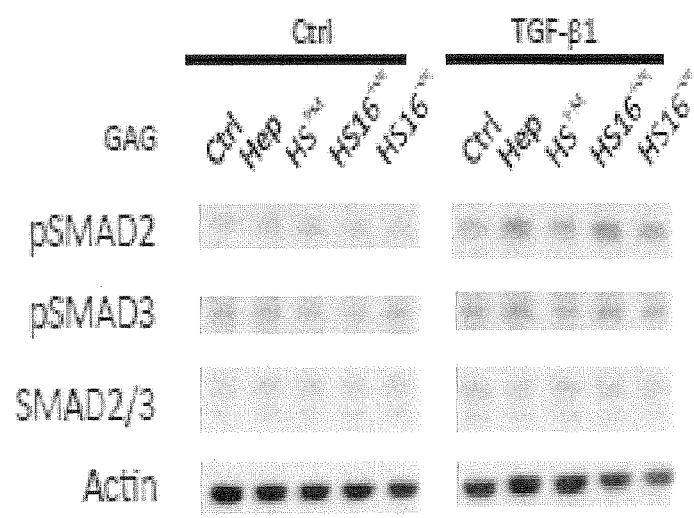
Figure 8D:
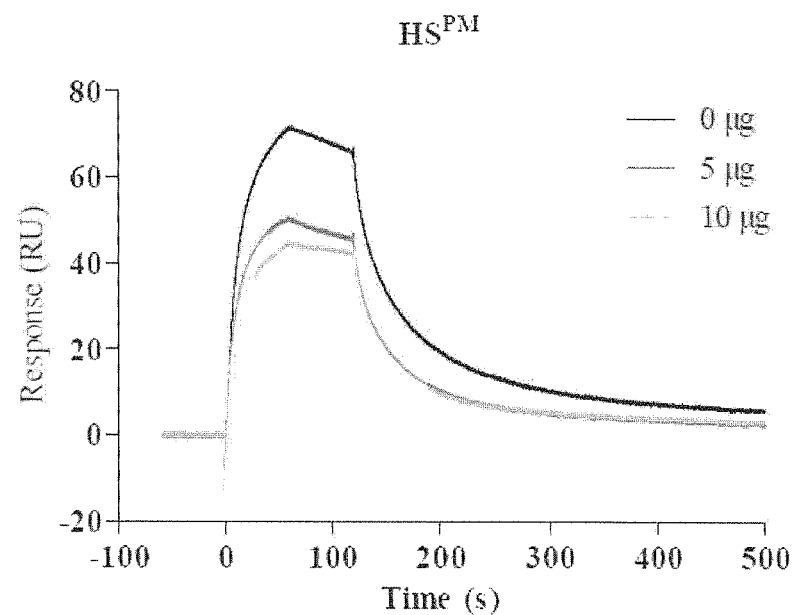
Figure 8E:
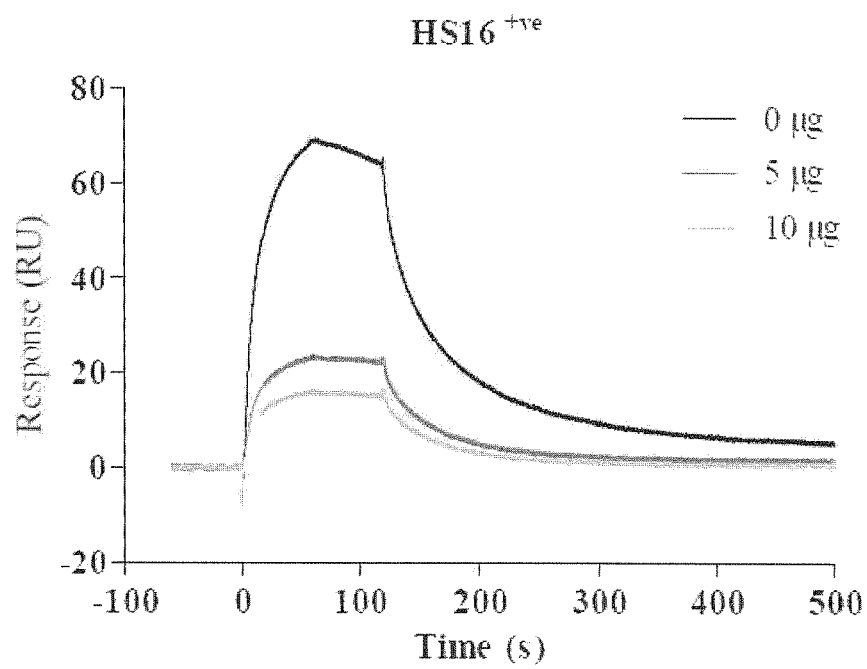
Figure 8F:
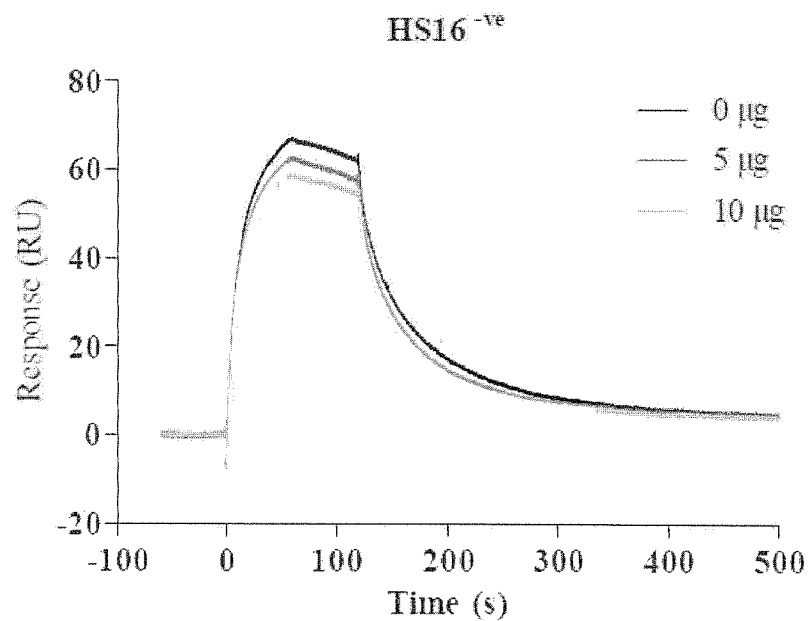
Figure 8G:
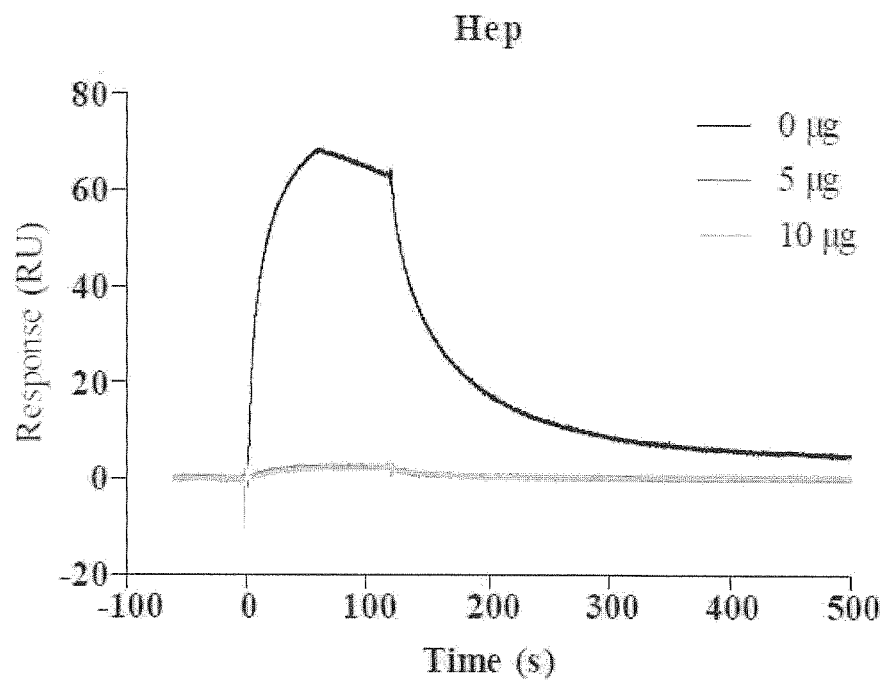
Figure 8H:
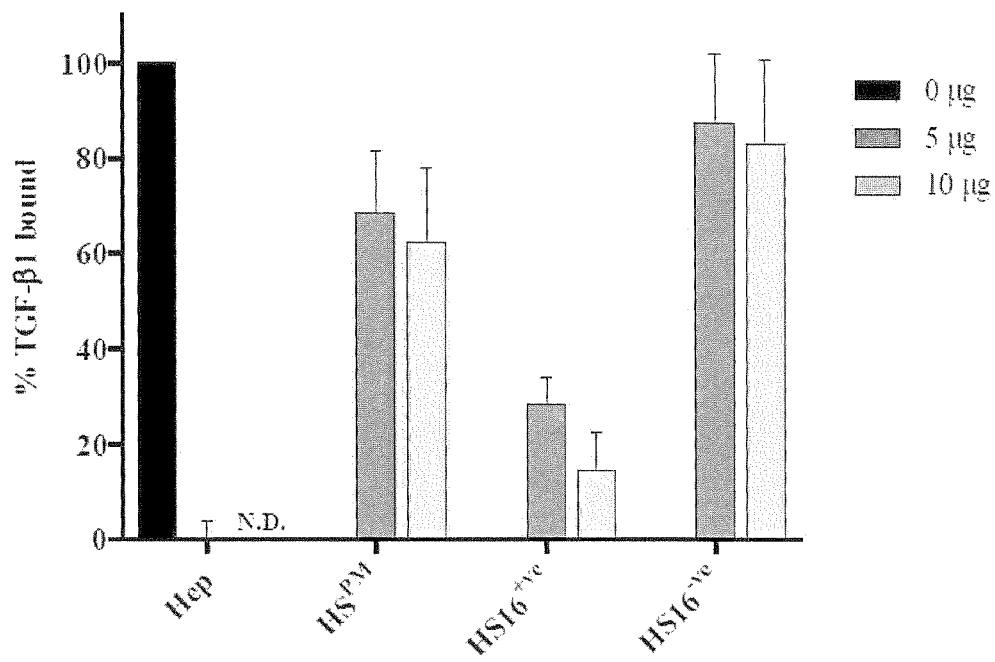

The data indicate that the pool of HS that makes up HS16+ve is markedly different from HS16−ve and HSPM with respect to both size distribution and composition. Additionally, the relative reduction in ΔUA,2S-GlcNAc and ΔUA,2SGlcNS seen in HS16+ve corroborated the earlier observation that the loss of 2-O sulfate from heparin actually served to increase its bioactivity towards TGF-β1 (FIG. 4C). The increased relative proportion of ΔUA,2S-GlcNS,6S may have resulted from the peptide preferentially enriching for saccharides with N- and 6-O-sulfation, regardless of the presence of 2-O-sulfation.

the protein. To do this, we pre-bound the sugars (Hep, $HS^{PM}$, $HS16^{+ve}$ and $HS16^{-ve}$) with TGF-β1 and subjected them to a plasmin digest. Given that plasmin preferentially cleaves the carboxyl face of lysine and arginine residues, we reasoned that if a sugar were to bind with a degree of specificity to TGF-β1, it would endow the protein with a degree of protection from the plasmin. Silver staining of the plasmin digestion products revealed that $HS16^{+ve}$ (TGF-β1+ $HS16^{+ve}$) was better able to protect TGF-β1 from plasmin digestion than any of the other sugars tested, including heparin (TGF-β1+Hep) (FIG. 8B). In an in vitro system, $HS16^{+ve}$ was able to potentiate TGF-β1 signaling, via pSMAD2 and pSMAD3, in hMSCs to a similar degree as heparin (FIG. 8C). Interestingly, $HS^{PM}$ and $HS16^{-ve}$ were unable to elicit a similar response, reinforcing our earlier findings that $HS16^{+ve}$ is compositionally and functionally distinct from both $HS^{PM}$ and $HS16^{-ve}$.

Figure 10A:
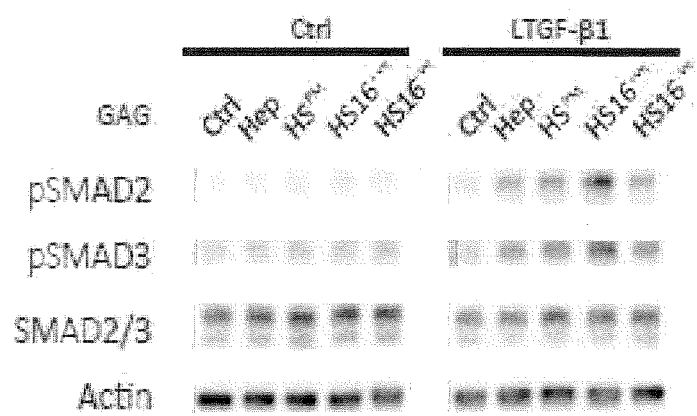
FIG. 10A to 10C. $HS16^{+ve}$ potentiates LTGF-β1 signaling. (A) Western blot: Cells were treated with LTGF-β1 (3.3 ng/ml), pre-incubated with 10 μg/ml of heparin (Hep), $HS^{PM}$ $HS16^{+ve}$ or $HS16^{-ve}$ for 10 min at room temperature, and lysed at 6 h. Phosphorylated SMAD2 (pSMAD2) and SMAD3 (pSMAD3), total SMAD2/3 and actin levels were determined by Western blotting. (B) Schematic model for the interaction of heparin/HS with LTGF-β1. Applying the same heparin-binding model from FIG. 9 to the LTGF-β1 structure (PDB: 3RJR (60)), the K13 residues may aid in the orientation of the heparin/HS chain (red line) to interfere with the binding of the latency associate peptide (LAP, colored beige) to mature TGF-β1. (C) Ribbon diagram of LTGF-β1 demonstrating how LAP wraps around the TGF-β1 homodimer.
Figure 10B:
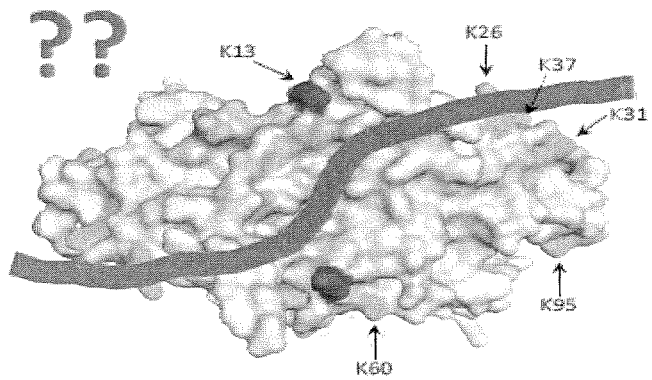
Figure 10C:
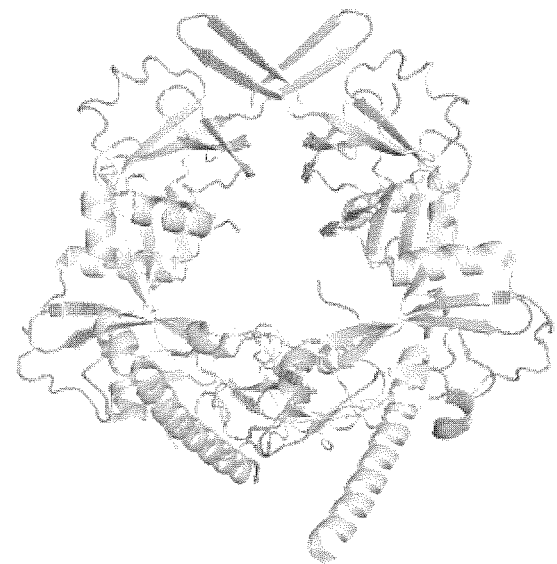
Figure 11:
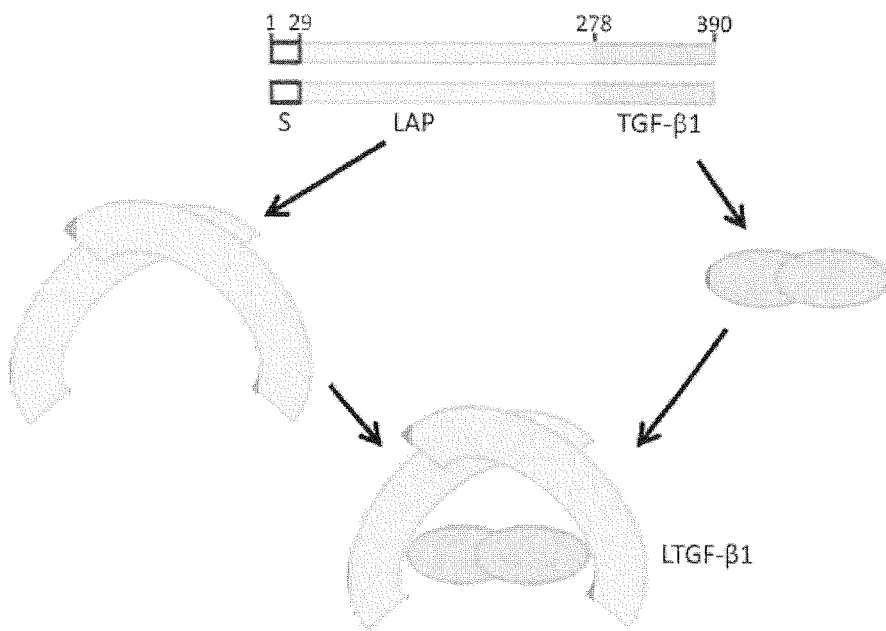
FIG. 11. Diagram showing process of TGF-β1 synthesis. TGF-β1 is synthesised as a 390 amino acid preproprotein containing a signal peptide (S), a latency-associated peptide (LAP) and TGF-β1 itself. After translation, the signal peptide is cleaved, disulphide bonds are formed between the two monomers and then LAP is cleaved from TGF-β1. LAP and TGF-β1 then re-associate non-covalently to form latent TGF-β1 (LTGF-β1), also known as the small latent complex (SLC). Disulphide bonds are coloured yellow.

As most TGF-β1 in vivo is found in an inactive form, known as latent TGF-β1 (LTGF-β1), and $HS16^{+ve}$ was isolated from a pool of $HS^{PM}$, we next sought to explore the effects that $HS16^{+ve}$ might have on LTGF-β1. Our data demonstrated that again $HS16^{+ve}$ was able to potentiate LTGF-β1-induced pSMAD signals more significantly than heparin (Hep), $HS^{PM}$ and $HS16^{-ve}$ (FIG. 10A). Collectively, our data shows that the $HS16^{+ve}$ isolate is better able to bind to and potentiate signaling driven by TGF-β1 compared to the $HS^{PM}$ starting material and the non-binding $HS16^{-ve}$. Also, $HS16^{+ve}$ was able to potentiate signaling driven by the more physiologically abundant LTGF-β1 compared to the HSPM starting material and the non-binding HS16−ve.

Isolation and Characterisation of hMSCs

In order to examine the biological effects of the heparin-TGF-β1 interaction, it was necessary to isolate primary hMSCs. Commercially available bone marrow cells (Lonza) were purchased and hMSCs isolated via plastic adherence. Passage 0 cells were subsequently expanded and frozen in batches of 1×106 cells per vial. Cells were screened by FACS for MSC surface marker expression at passage 5 as described by Dominici et al. [*Minimal criteria for defining multipotent mesenchymal stromal cells. The International Society for Cellular Therapy position statement*. Cytotherapy, 2006. 8(4): p. 315-317]. More than 95% of the

TABLE 2

Disaccharide composition of heparin lyase digested HS samples.
HS samples were digested with heparin lyase I, II and II and the resulting disaccharides were separated via HPLC. Disaccharides were identified by comparing their elution times with those of known disaccharide standards and their proportions in each HS sample were calculated with several calibration curves.

| | % Disaccharide | | | | | | |
|---|---|---|---|---|---|---|---|
| | ΔUA-GlcNAc | ΔUA-GlcNS | ΔUA-GlcNAc,6S | ΔUA,2S-GlcNAc | ΔUA-GlcNS,6S | ΔUA,2S-GlcNS | ΔUA,2S-GlcNS,6S |
| $HS^{PM}$ | 35.11 | 25.62 | 12.92 | 0.62 | 10.36 | 5.76 | 9.60 |
| HS16+ | 32.26 | 22.24 | 12.63 | 0.56 | 12.98 | 4.58 | 14.75 |
| HS16− | 35.44 | 26.77 | 12.79 | 0.64 | 9.83 | 6.08 | 8.45 |

$HS16^{+ve}$ Binds to and Potentiates TGF-β1 Signaling

Given the difference in the composition of $HS16^{+ve}$ compared to $HS16^{-ve}$ and $HS^{PM}$, we next set out to investigate if these differences resulted in any functional consequences. Examination of the ability of these HS fractions to bind to TGF-β1 in the Biacore competition assay indicated that $HS16^{+ve}$ was able to bind to TGF-β1 with a much higher affinity than $HS16^{-ve}$ or $HS^{PM}$ (FIG. 8A). As $HS16^{+ve}$ was isolated using a TGF-β1-derived peptide, it was important to assess the ability of the sugar to mask the basic residues on isolated hMSCs expressed CD73, CD90 and CD105, while CD14, CD19, CD34, CD45 and HLA-DR were not expressed. The isolated cells were also able to differentiate into osteoblasts, adipocytes and chondroblasts in vitro.

Thus the cells that had been isolated by plastic adherence were deemed to satisfy the minimal criteria characteristics of hMSCs.

Effects of Heparin on TGF-β1 Signalling in hMSCs

Having isolated primary hMSCs, we next examined if the interaction between heparin and TGF-β1 could influence the cellular response to TGF-β1 signalling, which was measured by way of the downstream phosphorylation of SMAD2 and SMAD3. Heparin has been shown to potentiate the effects of TGF-β1 in primary rat and bovine smooth muscle cells (SMCs) and the CCL64 mink lung epithelial cell line, but not in primary human saphenous vein (SMCs) [McCaffrey, T. A., et al., *Transforming growth factor-beta activity is potentiated by heparin via dissociation of the transforming growth factorbeta/alpha 2-macroglobulin inactive complex.* J Cell Biol, 1989. 109(1): p. 441-44; McCaffrey, T. A., et al., *Protection of transforming growth factor β activity by heparin and fucoidan.* J Cell Physiol, 1994. 159(1): p. 51-59]. We therefore postulated that should heparin potentiate TGF-β1 activity in hMSCs, the effects would only be seen as the pSMAD2 and pSMAD3 signals from TGF-β1 alone started to subside. Thus the time points chosen for our initial TGF-β1 dosing experiment were 6, 12, 24 and 48 h. Passage 5 cells were treated with a range of TGF-β1 doses and total cell lysate collected at 6, 12, 24 and 48 h post treatment. Lysate samples were then resolved on 4-12% (w/v gradient) SDS-PAGE gels, transferred onto a nitrocellulose membrane and probed for phospho-SMAD2 (pSMAD2) (138D4, Cell Signaling Technology), phospho-SMAD3 (pSMAD3) (C25A9, Cell Signaling Technology), total SMAD2/3 (Cell Signaling Technology) and actin (Clone C4, Merck Millipore) by Western blotting. Our results showed that without TGF-β1 (0 ng/mL), there was a low background level of pSMAD2 and pSMAD3 signalling. With 1 ng/mL, the pSMAD2 signal was quite intense at 6 h post treatment, and started to subside from 12 h onwards. The pSMAD3 signal mirrored that of the pSMAD2 signal, albeit at a lower intensity. With both 5 ng/mL and 10 ng/mL TGF-β1, the pSMAD2 signal was seen to remain saturated across all the time points tested, but the pSMAD3 signal returned to background levels by 24 h. The 6 h time point was thus chosen for all subsequent experiments.

Our next goal was to determine the dose of heparin to use for our experiments. As McCaffrey et al. (supra)] have previously reported the effective TGF-β1-potentiating dose of heparin to be between 1-100 μg/mL, we chose to use doses within this range. Cells that were treated with 1 ng/mL of TGF-β1 pre-incubated with 10 μg/mL of heparin maintained a stronger pSMAD2 and pSMAD3 signal compared to cells treated with the same dose of TGF-β1 alone (FIG. 3.12). A higher dose of heparin (40 μg/mL) was unable to elicit the same effect with 1 ng/mL of TGF-β1. When preincubated with 5 ng/mL of TGF-β1, neither dose of heparin was able enhance the pSMAD signal beyond that obtained from the growth factor alone. Taken together, our results suggest that heparin prolongs rather than enhances the pSMAD signals produced by TGF-β1.

We next sought to examine the influence that cell surface HS might have on TGF-β1-driven SMAD signalling. To do so, passage 5 cells were treated with heparinase I, II and III (1.2 mIU/mL each) for 24 h in hMSC culture medium, before being treated with TGF-β1 with or without heparin in serum-free medium. The 6 h time point used for Western blotting necessitated the use of serum-free media after heparinase treatment, in order to avoid the effects that the growth factors in the serum would have on background levels of SMAD2 and 3. Immunofluorescence staining of cell surface HS with the anti-HS 10E4 antibody showed that after 24 h treatment, nearly all the cell surface HS had been removed. However, the removal of cell surface HS did not appear to affect the pSMAD signals produced when the cells were treated with TGF-β1. Our results suggest that the role played by heparin in potentiating TGF-β1 signalling is different from the role it plays in FGF-2 signalling [Schlessinger, J., et al., *Crystal Structure of a Ternary FGF-FGFR-Heparin Complex Reveals a Dual Role for Heparin in FGFR Binding and Dimerization.* Molecular Cell, 2000. 6(3): p. 743-750.].

Comparison of HS16+ve and BMP-2-Binding HS (HS3+ve)

Figure 12:
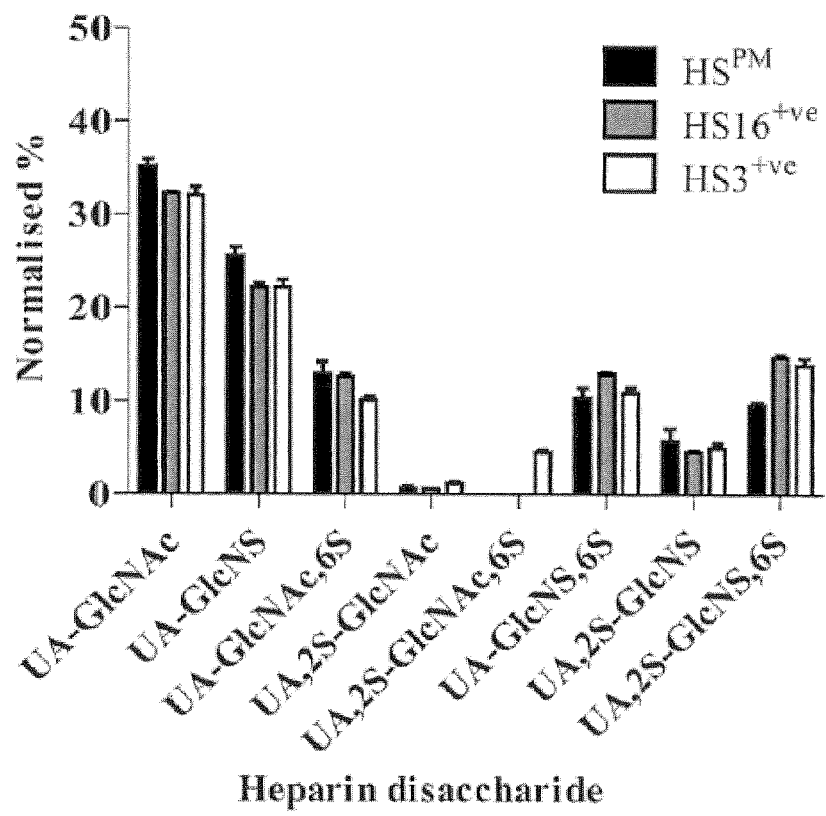
FIG. 12. Comparison of HSPM, HS16+ve and HS3+ve compositions. Bar chart showing the compositional differences between HSPM, HS16+ve and HS3+ve, a BMP-2-binding fraction of HSPM. HSPM and HS16+ve compositions were determined by HPLC, which was unable to detect the rare UA,2S-GlcNAc,6S disaccharide, while HS3+ve composition was determined by capillary electrophoresis. Error bars represent error intervals, which were determined using student's t-distribution with confidence limits set at 95. Data on HS3+ve taken from [Murali, S., et al., *Affinity-selected heparan sulfate for bone repair*. Biomaterials, 2013. 34(22): p. 5594-5605] and used for comparison.
Figure 13A:
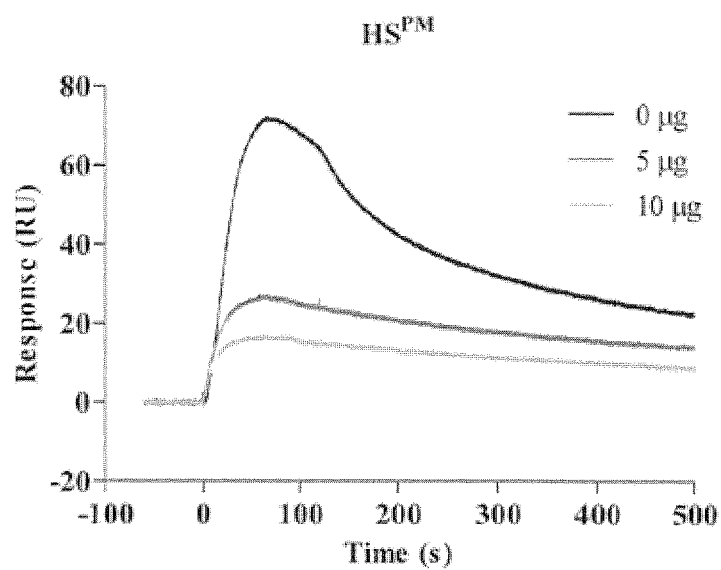
FIG. 13A to 13E. Comparison of HS16+ve and HS3+ve binding to BMP-2. Representative SPR sensograms showing the changes in binding response of 25 nM of BMP-2 when pre-incubated with either 5 or 10 μg of (A) HSPM, (B) HS3+ve, (C) HS16+ve or (D) heparin (Hep) prior to injection. (E) Bar chart depicts the ability of the various GAGs to compete for BMP-2 binding against the heparin-coated surface. For clarity, the binding response of BMP-2 without any GAG (i.e. 0 μg) is only shown for heparin. Data were normalised to 25 nM BMP-2 alone. Error bars represent standard deviation, n=3.
Figure 13B:
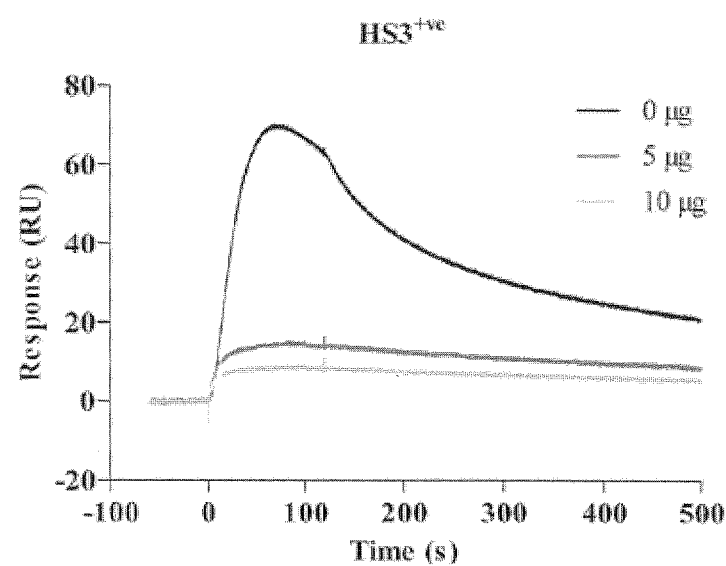
Figure 13C:
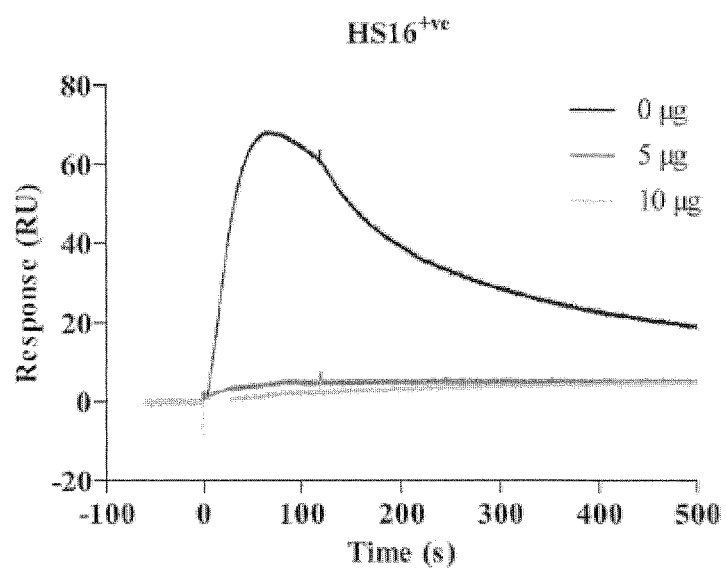
Figure 13D:
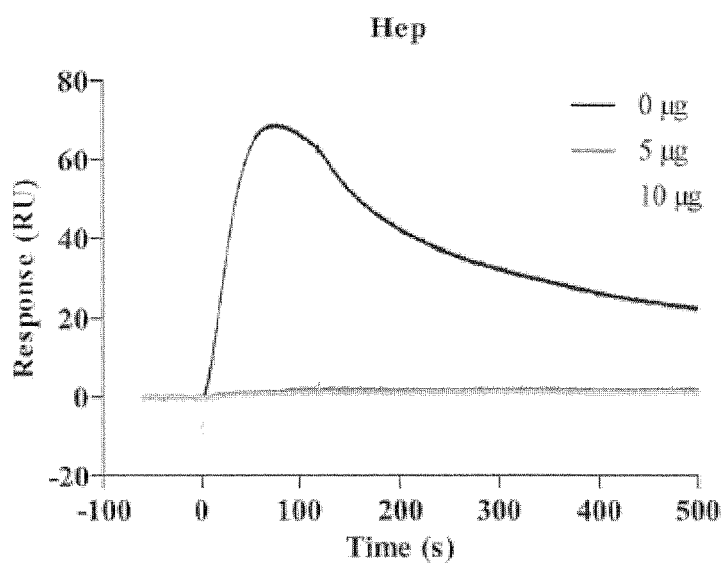
Figure 13E:
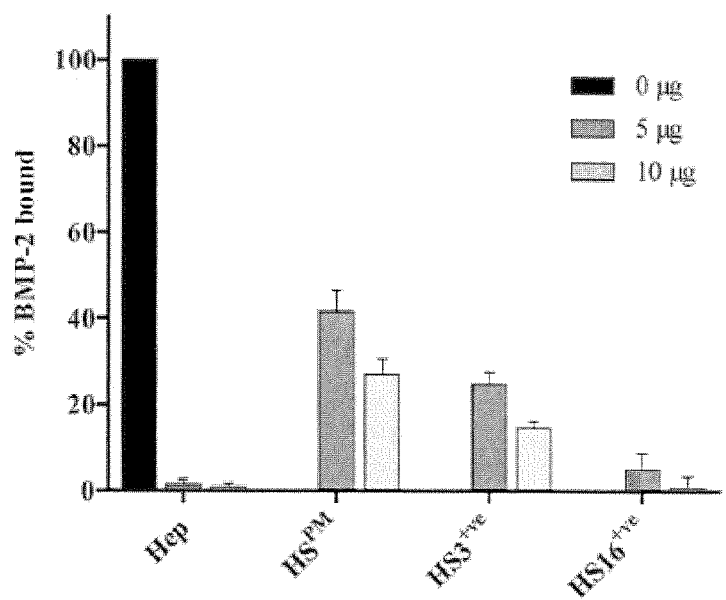

Having shown that HS16+ve enhances TGF-β1 signalling, it was of interest to determine if it might similarly enhance the activity of other members of the TGF-β superfamily. Our group has previously reported the affinity isolation of an HS fraction, HS3+ve, which enhances the activity of BMP-2 [Murali, S., et al., *Affinity-selected heparan sulfate for bone repair.* Biomaterials, 2013. 34(22): p. 5594-5605; WO2010/030244]. The structural similarity between the two proteins warranted a comparison of the composition of HS16+ve and HS3+ve (FIG. 12). Both HS3+ve and HS16+ve were found to contain similar amounts of ΔUA-GlcNAc, ΔUA-GlcNS and ΔUA,2S-GlcNS, while HS16+ve contained more ΔUA-GlcNAc,6S, ΔUA-GlcNS,6S and ΔUA,2S-GlcNS,6S and less ΔUA,2S-GlcNAc than HS3+ve. It must be noted that the composition of HS3+ve was determined by capillary electrophoresis (GE), while that of HS16+ve and HSPM were determined by HPLC, so the ΔUA,2S-GlcNAc,6S disaccharide was not detected in the latter two samples. One could argue that the inability to detect this disaccharide would alter the compositional profile of the HS variants, but previous analyses of HSPM using the CE method yielded composition profiles similar to the ones obtained with HPLC without the ΔUA, 2S-GlcNAc,6S disaccharide.

Figure 14:
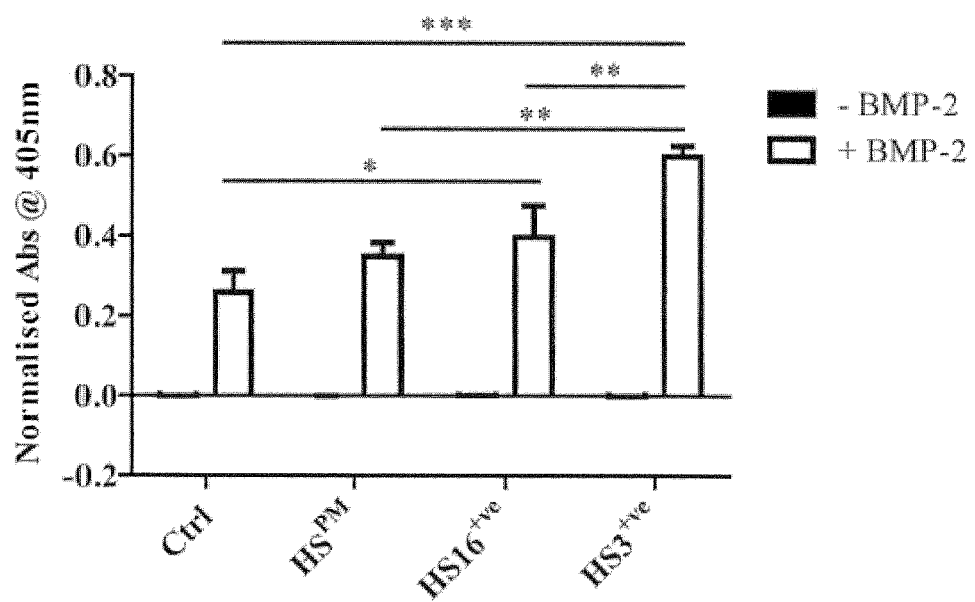
FIG. 14. BMP-2 potentiating ability of HS16+ve. Bar chart depicting the ability of HSPM, HS16+ve and HS3+ve to potentiate BMP-2-driven expression of alkaline phosphatase (ALP) in C2C12 cells. Error bars represent SD, n=4. * P<0.05,  P<0.01,  P<0.001.

This observed difference in the compositions of HS16+ve and HS3+ve had functional consequences for their activity. Surprisingly, HS16+ve was found to bind to BMP-2 better that HS3+ve in SPR-based binding competition assay (FIG. 13). However, when investigated for its ability to potentiate the BMP-2 driven expression of alkaline phosphatase (ALP) in the mouse C2C12 myoblast cell line, the combination of HS16+ve and BMP-2 was unable to effect the same level of ALP expression seen when HS3+ve was used with BMP-2 (FIG. 14).

Collectively, the data show that HS that is affinity purified using a TGF-β1 peptide is compositionally different from the original HS preparation, will bind to the full length protein and potentiate its activity both in its active and latent forms. Also, the HS purified with the TGF-β1 peptide is different from that purified with a BMP-2 peptide and this difference is sufficient to alter or tune its activity towards TGF-β1 and reduce the heterogeneous effects of unfractionated $HS^{PM}$.

Discussion

In this study we have shown that heparin is able to bind to TGF-β1, and in so doing, enhance the thermal stability of the growth factor. This stabilization appears to prolong the half-life of TGF-β1 signaling activity in hMSCs. Under chondrogenic differentiation conditions, this heparin-mediated potentiation enhanced the expression of early chondrogenic genes. Our findings support the idea that the potentiating effect of heparin on this chondrogenic gene expression occurs as a result of heparin acting via the TGF-β1 signaling pathway, and that a GAG chain between 18-22 saccharides long is required to optimally bind to TGF-β1 and potentiate its signal. Examination of the ternary TGF-β1 ligand-receptor complex indicated that longer heparin chains might interfere with the binding of the TGF-6 type II receptor (TδRII) with TGF-β1 during complex formation (43). The loss of 2-O sulfation, and to a lesser extent 6-O sulfation, actually improves the ability of heparin to potentiate the TGF-β1 signal despite a reduction in binding affinity. Together with our earlier findings on the influence of heparin chain length, these results provide compelling evidence for the current 'sugar code' hypothesis of HS (44-47) and reinforce the idea of a non-linear relationship between binding strength and bioactivity (48). We have also identified K13 as a new residue on the TGF-β1 monomer involved in heparin binding. Guided by that data we proceeded to isolate a population of HS that preferentially binds to TGF-β1 (HS16$^{+ve}$) from the heterogeneous mix obtained from porcine mucosal preparations. Characterization of HS16$^{+ve}$ demonstrated that it was compositionally different from HS$^{PM}$ and HS16$^{-ve}$, and that this difference enabled it to better bind to and potentiate both TGF-β1 and LTGF-β1 signaling in hMSCs.

Previous studies have shown that heparin will bind to TGF-β1 and protect it from protease activity and circulatory clearance by a 2-macroglobulin, thereby potentiating its signal (3,5). This has led to its use as either a TGF-β carrier or as a scaffold material in some cartilage repair studies (49,50). Some studies have even utilized heparin to control the release of growth factors during the chondrogenic induction of murine MSCs (51). However, this sugar is unlikely to see widespread adoption as a therapeutic agent for tissue repair or growth factor modulation, not only because of the risk of uncontrolled bleeding and thrombocytopenia (52), but because the hypersulfation of heparin means that is capable of promiscuously binding to over 200 different extracellular proteins, collectively known as the heparin interactome or heparanome (53,54). This implies that heparin does not possess sufficient specificity to be used for targeted growth factor modulation in an in vivo system, where growth factor production and localization cannot easily be controlled. Nonetheless, our in vitro data indicate that heparin can be used to prolong TGF-β1 activity during hMSC chondrogenic differentiation, suggesting that there is a therapeutic potential to be realized if these inherent limitations can be overcome.

The use of HS instead of heparin could theoretically overcome these hurdles, as HS does not possess the anticoagulant activity of heparin (55). However, HS does give rise to its own set of problems, including the hypervariability of raw preparations. There are, however, techniques that have been developed to surmount these difficulties (26,27,29) and, by utilizing one of these techniques (29), we were able to demonstrate that selective sub-populations of HS that preferentially bind specific growth factors can be isolated. It was noteworthy that while HS16+ was isolated using a TGF-β1-derived peptide, HS16$^{+ve}$ is also able to modulate the effects of LTGF-β1, the more physiologically abundant form of TGF-β1 in vivo. Interestingly, heparin has been reported to inhibit the activation of LTGF-β1 (56), whereas HS16$^{+ve}$ does not. This raises interesting questions about the in vivo synthesis of TGF-β1-binding HS by cells during normal and altered physiological states.

Figure 9:
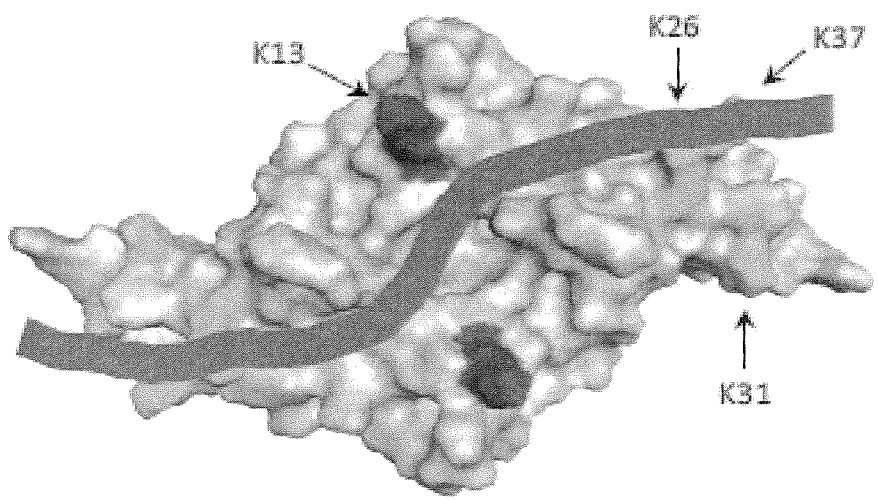
FIG. 9. Schematic model for the interaction of heparin/HS with TGF-β1. According to the model proposed by Lyon et al. (2), the heparin/HS chain (solid line) interacts with TGF-β1 through the K26 residue on either monomer. This model would involve the heparin/HS chain having to navigate the groove between the interfaces of the two protein monomers. The position of K13 would aid the sugar chain in the adoption of such a spatial orientation needed for binding to TGF-β1. Comparison of the predicted TGF-β1 structure with recently published heparin structures by Khan et al. (57) also suggests that a dp22 heparin fragment would be sufficient to bridge the distance between the K26 residues on either monomer.

The work reported here lays the groundwork for future TGF-β1-HS studies and builds on the binding model proposed by Lyon et al. (2). Our data identifies K13 as a novel residue that appears to influence the binding of heparin to TGF-β1 through a spatial orienting of the polysaccharide through the groove that runs between the protein monomers (FIG. 9). Additionally, the recent structural solution of several large heparin fragments (57) has enabled us to compare and validate our in vitro findings with the physical measurements of both TGF-β1 and heparin structures. Current, limited knowledge of the LTGF-β1 structure (58-60) also raises questions about the role played by heparin and HS for the modulation of this larger protein's activity (Supplemental fig. S1B, C).

TGF-β1 is synthesized first as a pro-protein that is cleaved intracellularly to yield the small latent complex (SLC). Mature SLC consists of the TGF-β1 dimer, noncovalently linked to the dimeric latency-associated peptide (LAP). For the majority of cell types so far studied SLC is released with latent TGF-β1-binding protein-1 (LTBP-1) together, so forming the large latent complex (LLC) (61). LTBP-1 pushes latent TGF-β1 into the extracellular matrix (ECM) by interacting with a variety of adhesive proteins (62), so creating deposits of latent TGF-β1 that can be made available upon cell-mediated activation. Although the LAP has a structure considered to be stable, two regions of the molecule can be unfolded (60) in such a way that it traps TGF-β1 in the SLC. When the conformations of these regions are mechanically forced fully open, active TGF-β1 is released from the LAP (58). This simultaneous unfolding of both domains, an all-or-nothing snap mechanism necessary for full TGF-β1 release, is possible only when LAP is bound to LTBP-1. Whether and how HS is involved in either the generation or release of this mechanical force is an interesting question.

All these considerations point to the need for extensive in silico modelling of the heparin-TGF-β1 interaction to validate our results, and the development of computational tools to decipher the domain organization of HS preparations like HS16$^{+ve}$ (63). Such studies would open up the possibility of refining our affinity-based isolation of HS or even the synthesis of chemically defined TGF-β1-specific HS molecules (64).

In conclusion, we show that heparin, and affinity isolated HS, can be used to modulate TGF-β1 signaling on hMSCs. We are also the first to report on the structural requirements for heparin-TGF-β1 interactions. Taken together, the data reiterates the importance of how an understanding of the structural interaction between these molecules can guide therapy development. This holds promise for the development of a novel therapeutic strategy for cartilage repair, which utilizes carbohydrate molecules to modulate TGF-β1 activity to drive the chondrogenic differentiation of hMSCs. Such a strategy could also be extended to other tissue repair strategies that involve the use of growth factors.

In our study, a peptide containing the heparin binding site of TGF-β1 was used to isolate a TGF-β1-binding fraction of HS from porcine mucosal HS (HSPM) by affinity purification. The isolated TGF-β1-peptide binding HS, termed HS16+ve, was found to be compositionally different from the non-bindng HS fraction, termed HS16−ve, and the original HSPM starting material. This variance in composition enhanced the ability of HS16+ve to bind to, and modulate the activity of TGF-β1 relative to HS16−ve and HSPM. Surprisingly, HS16+ve was also able to modulate the activity of LTGF, the inactive, storage form of TGF-β1. When compared with HS3+ve, an HS variant developed to enhance BMP-2 activity [Murali, S., et al., *Affinity-selected heparan sulfate for bone repair*. Biomaterials, 2013. 34(22): p. 5594-5605], HS16+ve was found to possess compositional differences, which altered its ability to potentiate BMP-2 activity compared to HSPM and HS3+ve.

In this work, the peptide used was 16 amino acids in length, while full length mature TGF-β1 is 112 amino acids in length. Peptides in solution are known to adopt conformations different from those assumed when part of a full protein, and structure predictions of the TGF-β1 peptide used for HS16+ve isolation, using PEPFOLD [Maupetit, J., P. Derreumaux, and P. Tuffery, *PEP-FOLD: an online resource for de novo peptide structure prediction*. Nucleic Acids Research, 2009. 37(suppl 2): p. W498-W503; Maupetit, J., P. Derreumaux, and P. Tuffery, *A fast method for large-scale DeNovo peptide and miniprotein structure prediction*. Journal of Computational Chemistry, 2010. 31(4): p. 726-738; and 216. Thévenet, P., et al., PEPFOLD: an updated de novo structure prediction server for both linear and disulfide bonded cyclic peptides. Nucleic Acids Research, 2012. 40(W1): p. W288-W293], do not match its native structure in TGF-β1. This raises the question of the mechanism that drives our peptide-based affinity purification, as it is hard to conceive that a single stretch of peptide will be able to recreate the spatial organisation of the TGF-β1 heparin-binding domain. One could argue that the interaction between the peptide and HS is primarily driven by ionic interactions, which is almost certainly true for peptide-heparin interactions (unpublished data from our group), but it does not appear to be the case here as the use of a peptide from a different protein (BMP-2) alters the profile of the isolated HS fractions.

The extensively investigated consensus sequence of basic residues involved in heparin-binding is proposed to adopt one of two motifs of basic residues: -X-B-B-BX-X-B-X-X- or -X-B-B-X-B-X-X- (where X is any neutral or acidic amino acid and B is a basic residue) [Cardin, A. D. and N. J. Weintraub, *Molecular modeling of protein glycosaminoglycan interactions*. Arteriosclerosis, Thrombosis, and Vascular Biology, 1989. 9(1): p. 21-32.]. A third motif has been proposed to exist in TGF-β1: -X-BX-X-B-X-X-B-X-X-B-X- [McCaffrey, T. A., D. J. Falcone, and B. Du, *Transforming growth factor-β1 is a heparin-binding protein: Identification of putative heparin-binding regions and isolation of heparins with varying affinity for TGF-β1*. J Cell Physiol, 1992. 152(2): p. 430-440.]. Intriguingly, Pace and Scholtz [Nick Pace, C. and J. Martin Scholtz, *A Helix Propensity Scale Based on Experimental Studies of Peptides and Proteins*. Biophysical Journal, 1998. 75(1): p. 422-427] have reported that basic residues have a high propensity to form α-helices in solution. Given the organisation of basic residues in these proposed motifs and that of the α-helix (3.6 amino acid residues per turn), it would not be surprising to find that these motifs adopt a helical structure in solution with their basic residues arrayed along the same plane. If true, such organisation might confer some degree of selectivity to the peptides.

Sizing and compositional analysis of HS16+ve showed that it was enriched for longer polysaccharide chains, less heterogeneous, in terms of chain size distribution, and enriched for 6-O- and N-sulphated disaccharides relative to both HS16−ve and HSPM. This corroborated our findings from our study of heparin-TGF-β1 interactions, where we identified the need for heparin chains to be at least equivalent to a dp22 and possess 6-O- and N-sulphate groups in order to effectively bind to and modulate TGF-β1 activity. Enrichment for longer chains of HS can be explained by the need for at least 22 saccharide units to bridge the two heparin/HS binding sites on the TGF-β1 homodimer. Such chains would also have to satisfy the sulphate distribution criteria to effectively interact with TGF-β1, which would further narrow the range of HS chains selected by our purification.

HS16+ve was able to potentiate TGF-β1-driven SMAD signalling to a similar degree as heparin. Unexpectedly, its effect on LTGF-β1 was more pronounced than that of heparin with LTGF-β1. As LTGF-β1 is the predominant form of TGF-β1 in vivo, this raises interesting questions about the synthesis of, and physiological role played by HS in TGF-β1 signalling. The latency-associated peptide (LAP) portion of LTGF has a structure considered to be stable, although two regions of the molecule can be unfolded [Shi, M., et al., *Latent TGF-β structure and activation*. Nature, 2011. 474(7351): p. 343-349] in such a way that it traps TGF-β1 in the LTGF-β1 complex. When the conformations of these regions are mechanically forced fully open, active TGF-β1 is released from the LAP [Buscemi, L., et al., *The Single-Molecule Mechanics of the Latent TGF-β1 Complex*. Curr Biol, 2011. 21(24): p. 2046-2054]. This simultaneous unfolding of both domains, an all-or-nothing snap mechanism necessary for full TGF-β1 release, is possible only when LAP is bound to LTGF-binding protein-1 (LTBP-1). It is interesting to note that both LAP and LTBP-1 have been reported to interact with heparin [Lee, M. J., *Heparin Inhibits Activation of Latent Transforming Growth Factor-β1*. Pharmacology, 2013. 92(5-6): p. 238-244; Chen, Q., et al., *Potential Role for Heparan Sulfate Proteoglycans in Regulation of Transforming Growth Factor-β (TGF-β) by Modulating Assembly of Latent TGF-β-binding Protein-1*. J Biol Chem, 2007. 282(36): p. 26418-26430; and Parsi, M. K., et al., *LTBP-2 has multiple heparin/heparan sulfate binding sites*. Matrix Biology, 2010. 29(5): p. 393-401]. Whether and how HS is involved in either the generation or release of this mechanical force is a pertinent question, though the evidence suggests that the HS synthesised in vivo may be tuned to activate LTGF-β1.

Comparison of the composition of HS16+ve with that of HS3+ve revealed differences in their compositions. The differences observed in the ability of either HS variant to bind to and modulate BMP-2 activity is probably a result of a combination of the differences in composition and consequently the disaccharide sequences embodied in the HS chains. Modelling of the BMP-2-heparin interaction [Gandhi, N. S. and R. L. Mancera, *Prediction of heparin binding sites in bone morphogenetic proteins (BMPs)*. Biochimica et Biophysica Acta (BBA)—Proteins and Proteomics, 2012. 1824(12): p. 1374-1381] suggests that the association varies significantly from that of heparin with TGF-β1, which would explain the differences in the compositions of HS16+ve and HS3+ve, and hints at the diversification of heparin/HS binding sites within the TGF-β superfamily [Rider, C. C., *Heparin/heparan sulphate binding in the TGF-β cytokine superfamily*. Biochem Soc Trans, 2006. 34(Pt 3): p. 458-460]. The modest increase observed in the ability of HS16+ve to potentiate BMP-2 driven ALP expression relative to $HS^{PM}$ might be attributable to either the enrichment of sulphated HS chains in HS16+ve, making it more similar to heparin than HSPM, or an overlap in the composition of HS chains in HS16+ve and HS3+ve preparations.

While HS does not appear to be encoded with the same absolute sequence specificity seen in nucleic acids and proteins, our results provide compelling evidence for the current HS "sugar code" hypothesis [Gama, C. I., et al., *Sulfation patterns of glycosaminoglycans encode molecular recognition and activity*. Nat Chem Blot, 2006. 2(9): p. 467-473; Duchesne, L., et al., *Transport of Fibroblast Growth Factor 2 in the Pericellular Matrix Is Controlled by the Spatial Distribution of Its Binding Sites in Heparan Sulfate*. PLoS Blot, 2012. 10(7): p. e1001361; Chang, Z., et al., *Differential ability of heparan sulfate proteoglycans to assemble the fibroblast growth factor receptor complex in situ*. FASEB J, 2000. 14(1): p. 137-144; and Jastrebova, N., et al., *Heparan sulfate domain organization and sulfation modulate FGF2 induced cell signaling*. J Blot Chem, 2010] and reinforce the idea of a non-linear relationship between binding strength and bioactivity [Rudd, T. R., et al., *Comparable stabilisation, structural changes and activities can be induced in FGF by a variety of HS and non-GAG analogues: implications for sequence-activity relationships. Org Biomol Chem*, 2010. 8(23): p. 5390-5397.]. One of the major questions that remain to be answered is the level of stringency required for a given HS chain to interact with a given protein. It is hoped that the development of improved computational tools to decode the organisation of GAGs will aid in this endeavour [Spencer, J. L., et al., *A Computational Approach for Deciphering the Organization of Glycosaminoglycans*. PLoS ONE, 2010. 5(2): p. e9389].

REFERENCES FOR EXAMPLE 1

1. Ori, A., Wilkinson, M. C., and Fernig, D. G. (2011) *J Biol Chem*
2. Lyon, M., Rushton, G., and Gallagher, J. T. (1997) *J Biol Chem* 272, 18000-18006
3. McCaffrey, T. A., Falcone, D. J., Brayton, C. F., Agarwal, L. A., Welt, F. G., and Weksler, B. B. (1989) *J Cell Biol* 109, 441-448
4. McCaffrey, T. A., Falcone, D. J., and Du, B. (1992) *J Cell Physiol* 152, 430-440
5. McCaffrey, T. A., Falcone, D. J., Vicente, D., Du, B., Consigli, S., and Borth, W. (1994) *J Cell Physiol* 159, 51-59
6. Lee, J.-H., Lee, H., Joung, Y. K., Jung, K. H., Choi, J.-H., Lee, D.-H., Park, K. D., and Hong, S.-S. (2011) *Biomaterials* 32, 1438-1445
7. Watson, R. S., Gouze, E., Levings, P. P., Bush, M. L., Kay, J. D., Jorgensen, M. S., Dacanay, E. A., Reith, J. W., Wright, T. W., and Ghivizzani, S. C. (2010) *Lab Invest* 90, 1615-1627
8. Siebert, N., Xu, W., Grambow, E., Zechner, D., and Vollmar, B. (2011) *Lab Invest* 91, 1753-1765
9. Jakowlew, S. (2006) *Cancer Metastasis Rev* 25, 435-457
10. Yang, Y.-a., Dukhanina, O., Tang, B., Mamura, M., Letterio, J. J., MacGregor, J., Patel, S. C., Khozin, S., Liu, Z.-y., Green, J., Anver, M. R., Merlino, G., and Wakefield, L. M. (2002) *J Clin Invest* 109, 1607-1615
11. Grimaud, E., Heymann, D., and Rédini, F. (2002) *Cytokine Growth Factor Rev* 13, 241-257
12. Rosen, F., McCabe, G., Quach, J., Solan, J., Terkeltaub, R., Seegmiller, J. E., and Lotz, M. (1997) *Arthritis Rheum* 40, 1275-1281
13. Toh, W. S., Liu, H., Heng, B. C., Rufaihah, A. J., Ye, C. P., and Cao, T. (2005) *Growth Factors* 23, 313-321
14. van der Kraan, P. M., Blaney Davidson, E. N., Blom, A., and van den Berg, W. B. (2009) *Osteoarthritis Cartilage* 17, 1539-1545
15. Yang, X., Chen, L., Xu, X., Li, C., Huang, C., and Deng, C.-X. (2001) *J Cell Biol* 153, 35-46
16. Miura, Y., Parvizi, J., Fitzsimmons, J. S., and O'Driscoll, S. W. (2002) *J Bone Joint Surg Am* 84, 793-799
17. Sato, M., Ishihara, M., Ishihara, M., Kaneshiro, N., Mitani, G., Nagai, T., Kutsuna, T., Asazuma, T., Kikuchi, M., and Mochida, J. (2007) *J Biomed Mater Res B Appl Biomater* 83B, 181-188
18. Wang, W., Li, B., Li, Y., Jiang, Y., Ouyang, H., and Gao, C. (2010) *Biomaterials* 31, 5953-5965
19. Allen, J. B., Manthey, C. L., Hand, A. R., Ohura, K., Ellingsworth, L., and Wahl, S. M. (1990) *J Exp Med* 171, 231-247
20. Leah, E. (2013) *Nat Rev Rheumatol* 9, 382-382
21. Bakker, A. C., van de Loo, F. A. J., van Beuningen, H. M., Sime, P., van Lent, P. L. E. M., van der Kraan, P. M., Richards, C. D., and van den Berg, W. B. (2001) *Osteoarthritis Cartilage* 9, 128-136
22. Blaney Davidson, E. N., Scharstuhl, A., Vitters, E. L., van der Kraan, P. M., and van den Berg, W. B. (2005) *Arthritis Res Ther* 7, R1338-R1347
23. Kopesky, P. W., Vanderploeg, E. J., Kisiday, J. D., Frisbie, D. D., Sandy, J. D., and Grodzinsky, A. J. (2011) *Tissue Eng Part A* 17, 83-92
24. Shah, R. N., Shah, N. A., Del Rosario Urn, M. M., Hsieh, C., Nuber, G., and Stupp, S. I. (2010) *Proc Natl Acad Sci USA* 107, 3293-3298
25. Coupes, B. M., Williams, S., Roberts, I. S. D., Short, C. D., and Brenchley, P. E. C. (2001) *Nephrol Dial Transplant* 16, 361-367
26. Bramono, D. S., Murali, S., Rai, B., Ling, L., Poh, W. T., Lim, Z. X., Stein, G. S., Nurcombe, V., van Wijnen, A. J., and Cool, S. M. (2012) *Bone* 50, 954-964
27. Helledie, T., Dombrowski, C., Rai, B., Lim, Z. X. H., Hin, I. L. H., Rider, D. A., Stein, G. S., Hong, W., van Wijnen, A. J., Hui, J. H., Nurcombe, V., and Cool, S. M. (2012) *Stem Cells Dev* 21, 1897-1910
28. Murali, S., Leong, D. F. M., Lee, J. J. L., Cool, S. M., and Nurcombe, V. (2011) *J Biol Chem* 286, 17755-17765
29. Murali, S., Rai, B., Dombrowski, C., Lee, J. L. J., Lim, Z. X. H., Bramono, D. S., Ling, L., Bell, T., Hinkley, S., Nathan, S. S., Hui, J. H., Wong, H. K., Nurcombe, V., and Cool, S. M. (2013) *Biomaterials* 34, 5594-5605
30. Samsonraj, R. M., Raghunath, M., Hui, J. H., Ling, L., Nurcombe, V., and Cool, S. M. (2013) *Gene* 519, 348-355
31. Rider, D. A., Dombrowski, C., Sawyer, A. A., Ng, G. H. B., Leong, D., Hutmacher, D. W., Nurcombe, V., and Cool, S. M. (2008) *Stem Cells* 26, 1598-1608
32. Zhang, L., Su, P., Xu, C., Yang, J., Yu, W., and Huang, D. (2010) *Biotechnol Lett* 32, 1339-1346
33. Hernaiz, M., Liu, J., Rosenberg, R. D., and Linhardt, R. J. (2000) *Biochem Biophys Res Commun* 276, 292-297
34. Uniewicz, K. A., Ori, A., Xu, R., Ahmed, Y., Wilkinson, M. C., Fernig, D. G., and Yates, E. A. (2010) *Anal Chem* 82, 3796-3802
35. Xu, R., Ori, A., Rudd, T. R., Uniewicz, K. A., Ahmed, Y. A., Guimond, S. E., Skidmore, M. A., Siligardi, G., Yates, E. A., and Fernig, D. G. (2012) *J Biol Chem* 287, 40061-40073
36. Livak, K. J., and Schmittgen, T. D. (2001) *Methods* 25, 402-408
37. Ori, A., Free, P., County, J., Wilkinson, M. C., and Fernig, D. G. (2009) *Mol Cell Proteomics* 8, 2256-2265
38. Guerrini, M., Naggi, A., Guglieri, S., Santarsiero, R., and Torri, G. (2005) *Anal Biochem* 337, 35-47
39. Knobloch, J. E., and Shaklee, P. N. (1997) *Anal Biochem* 245, 231-241
40. Brickman, Y. G., Ford, M. D., Gallagher, J. T., Nurcombe, V., Bartlett, P. F., and Turnbull, J. E. (1998) *J Biol Chem* 273, 4350-4359
41. Skidmore, M. A., Guimond, S. E., Dumax-Vorzet, A. F., Yates, E. A., and Turnbull, J. E. (2010) *Nat Protoco* 5, 1983-1992
42. Inman, G. J., Nicolás, F. J., Callahan, J. F., Harling, J. D., Gaster, L. M., Reith, A. D., Laping, N. J., and Hill, C. S. (2002) *Mol Pharmacol* 62, 65-74
43. Radaev, S., Zou, Z., Huang, T., Lafer, E. M., Hinck, A. P., and Sun, P. D. (2010) *J Biol Chem* 285, 14806-14814
44. Gama, C. I., Tully, S. E., Sotogaku, N., Clark, P. M., Rawat, M., Vaidehi, N., Goddard, W. A., Nishi, A., and Hsieh-Wilson, L. C. (2006) *Nat Chem Biol* 2, 467-473

45. Chang, Z., Meyer, K., Rapraeger, A. C., and Friedl, A. (2000) *FASEB J* 14, 137-144
46. Duchesne, L., Octeau, V., Bearon, R. N., Beckett, A., Prior, I. A., Lounis, B., and Fernig, D. G. (2012) *PLoS Biol* 10, e1001361
47. Jastrebova, N., Vanwildemeersch, M., Lindahl, U., and Spillmann, D. (2010) *J Biol Chem*
48. Rudd, T. R., Uniewicz, K. A., Ori, A., Guimond, S. E., Skidmore, M. A., Gaudesi, D., Xu, R., Turnbull, J. E., Guerrini, M., Torri, G., Siligardi, G., Wilkinson, M. C., Fernig, D. G., and Yates, E. A. (2010) *Org Biomol Chem* 8, 5390-5397
49. Kim, M., Kim, S. E., Kang, S. S., Kim, Y. H., and Tae, G. (2011) *Biomaterials* 32, 7883-7896
50. Park, J. S., Woo, D. G., Yang, H. N., Lim, H. J., Chung, H.-M., and Park, K.-H. (2008) *Transplantation* 85, 589-596
51. Xu, X., Jha, A. K., Duncan, R. L., and Jia, X. (2011) *Acta Biomater* 7, 3050-3059
52. Kelton, J. G., Arnold, D. M., and Bates, S. M. (2013) *N Engl J Med* 368, 737-744
53. Lamanna, W. C., Kalus, I., Padva, M., Baldwin, R. J., Merry, C. L. R., and Dierks, T. (2007) *J Biotechnol* 129, 290-307
54. Ori, A., Wilkinson, M. C., and Fernig, D. G. (2008) *Front Biosci* 13, 4309-4338
55. Naimy, H., Leymarie, N., and Zaia, J. (2010) *Biochemistry* 49, 3743-3752
56. Lee, M. J. (2013) *Pharmacology* 92, 238-244
57. Khan, S., Gor, J., Mulloy, B., and Perkins, S. J. (2010) *J Mol Biol* 395, 504-521
58. Buscemi, L., Ramonet, D., Klingberg, F., Formey, A., Smith-Clerc, J., Meister, J.-J., and Hinz, B. (2011) *Curr Biol* 21, 2046-2054
59. Chen, Q., Sivakumar, P., Barley, C., Peters, D. M., Gomes, R. R., Farach-Carson, M. C., and Dallas, S. L. (2007) *J Biol Chem* 282, 26418-26430
60. Shi, M., Zhu, J., Wang, R., Chen, X., Mi, L., Walz, T., and Springer, T. A. (2011) *Nature* 474, 343-349
61. Annes, J. P., Munger, J. S., and Rifkin, D. B. (2003) *Journal of Cell Science* 116, 217-224
62. Ramirez, F., and Rifkin, D. B. (2009) *Current Opinion in Cell Biology* 21, 616-622
63. Spencer, J. L., Bernanke, J. A., Buczek-Thomas, J. A., and Nugent, M. A. (2010) *PLoS ONE* 5, e9389
64. Chappell, E. P., and Liu, J. (2013) *Bioorg Med Chem* 21, 4786-4792

Example 2

Effects of HS16+ve on Chondrogenic Differentiation of MSCs In Vitro and In Vivo

Introduction

Articular cartilage is a tissue found at the ends of long bones that serves as both a shock absorber and lubricant in our joints. As a consequence of its avascular nature, injuries sustained by articular cartilage often fail to heal. Current research into the development of cartilage repair strategies has focused on stimulating the response from either endogenous or transplanted cells, through the use of activated biomaterials or provision of inductive cues to the cells [145. Guo, X., et al., *Repair of osteochondral defects with biodegradable hydrogel composites encapsulating marrow mesenchymal stem cells in a rabbit model*. Acta Biomaterialia, 2010. 6(1): p. 39-47; Chu, C. R., M. Szczodry, and S. Bruno, *Animal Models for Cartilage Regeneration and Repair*. Tissue Engineering Part B: Reviews, 2009. 16(1): p. 105-115; Fritz, J., et al., *Articular cartilage defects in the knee—basics, therapies and results*. Injury, 2008. 39(1, Supplement): p. 50-57; Hunziker, E. B., *Articular cartilage repair: basic science and clinical progress. A review of the current status and prospects*. Osteoarthritis Cartilage, 2002. 10(6): p. 432-463; Gille, J., et al., *Cell-Laden and Cell-Free Matrix-Induced Chondrogenesis versus Microfracture for the Treatment of Articular Cartilage Defects: A Histological and Biomechanical Study in Sheep*. Cartilage, 2010. 1(1): p. 29-42; Haleem, A. M., et al., *The Clinical Use of Human Culture-Expanded Autologous Bone Marrow Mesenchymal Stem Cells Transplanted on Platelet-Rich Fibrin Glue in the Treatment of Articular Cartilage Defects*. Cartilage, 2010. 1(4): p. 253-261; Moran, C. J., et al., *Restoration of Articular Cartilage*. J Bone Joint Surg Am, 2014. 96(4): p. 336-344; Danišovič, Lu., et al., *The tissue engineering of articular cartilage: cells, scaffolds and stimulating factors*. Exp Biol Med, 2012. 237(1): p. 10-17]. TGF-β1 has emerged as a key player for the induction of cartilage repair because of its ability to stimulate the chondrogenic differentiation of MSCs [Buxton, A. N., et al., *Temporal exposure to chondrogenic factors modulates human mesenchymal stem cell chondrogenesis in hydrogels*. Tissue Eng Part A, 2011. 17(3-4): p. 371-80; 233. Bosnakovski, D., et al., *Chondrogenic differentiation of bovine bone marrow mesenchymal stem cells in pellet cultural system*. Experimental Hematology, 2004. 32(5): p. 502-509; Ng, F., et al., *PDGF, TGF-β, and FGF signaling is important for differentiation and growth of mesenchymal stem cells (MSCs): transcriptional profiling can identify markers and signaling pathways important in differentiation of MSCs into adipogenic, chondrogenic, and osteogenic lineages*. Blood, 2008. 112(2): p. 295-307], and drive the expression of cartilage ECM molecules [Li, H., et al., *Comparative analysis with collagen type II distinguishes cartilage oligomeric matrix protein as a primary TGFβ-responsive gene*. Osteoarthritis Cartilage, 2011. 19(10): p. 1246-1253; Iqbal, J., et al., *Age-Related Effects of TGF-β on Proteoglycan Synthesis in Equine Articular Cartilage*. Biochem Biophys Res Commun, 2000. 274(2): p. 467-471; Grimaud, E., D. Heymann, and F. Rédini, *Recent advances in TGF-β effects on chondrocyte metabolism: Potential therapeutic roles of TGF-β in cartilage disorders*. Cytokine Growth Factor Rev, 2002. 13(3): p. 241-257; Serra, R., et al., *Expression of a Truncated, Kinase-Defective TGF-β Type II Receptor in Mouse Skeletal Tissue Promotes Terminal Chondrocyte Differentiation and Osteoarthritis*. J Cell Biol, 1997. 139(2): p. 541-552; Blaney Davidson, E., et al., *TGF beta-induced cartilage repair is maintained but fibrosis is blocked in the presence of Smad7*. Arthritis Res Ther, 2006. 8(3): p. R65]. As such, most studies to date have employed the use of exogenous TGF-β1, either alone or in combination with other growth factors, to drive hMSC chondrogenic differentiation [Blaney Davidson, E. N., P. M. van der Kraan, and W. B. van den Berg, *TGF-β and osteoarthritis*. Osteoarthritis Cartilage, 2007. 15(6): p. 597-604; Park, J. S., et al., *Heparin-Bound Transforming Growth Factor-β3 Enhances Neocartilage Formation by Rabbit Mesenchymal Stem Cells*. Transplantation, 2008. 85(4): p. 589-596; Goepfert, C., et al., *Cartilage Engineering from Mesenchymal Stem Cells*, in *Bioreactor Systems for Tissue Engineering II*, C. Kasper, M. van Griensven, and R. Pörtner, Editors. 2010, Springer Berlin/Heidelberg. p. 163-200; Mara, C S., et al., *Regulation of Chondrogenesis by Transforming Growth Factor-β3 and

*Insulin-like Growth Factor*-1 *from Human Mesenchymal Umbilical Cord Blood Cells.* J Rheumatol, 2010. 37(7): p. 1519-1526].

While appearing successful initially, such approaches face significant barriers in their translation into the clinic, as supraphysiological doses of TGF-β1 are often employed, and even 20 ng doses have been shown to produce undesirable outcomes, such as synovial inflammation [Leah, E., *Osteoarthritis: TGF-β overload at bones of cartilage degeneration.* Nat Rev Rheumatol, 2013. 9(7): p. 382-382; Allen, J. B., et al., *Rapid onset synovial inflammation and hyperplasia induced by transforming growth factor beta.* J Exp Med, 1990. 171(1): p. 231-247]. Apart from the problem of non-physiological doses, there is also the need to localise the growth factor to the site of treatment to prevent it from triggering systemic side effects, such as fibrosis and oncogenesis [Jakowlew, S., *Transforming growth factor-β in cancer and metastasis.* Cancer Metastasis Rev, 2006. 25(3): p. 435-457; Bakker, A. C., et al., *Overexpression of active TGF-beta-1 in the murine knee joint: evidence for synovial-layer-dependent chondro-osteophyte formation.* Osteoarthritis Cartilage, 2001. 9(2): p. 128-136; Yang, Y.-a., et al., *Lifetime exposure to a soluble TGF-β antagonist protects mice against metastasis without adverse side effects.* J Clin Invest, 2002. 109(12): p. 1607-1615.]. Additionally, sensitivity to TGF-β1 decreases with age [Blaney Davidson, E. N., et al., *Reduced transforming growth factor-beta signalling in cartilage of old mice: role in impaired repair capacity.* Arthritis Res Ther, 2005. 7(6): p. R1338-R1347], so adequate TGF-β1 dosing presents even more risk for aged patients. In response to these challenges, new strategies are being considered that reduce, or completely remove the need for exogenous growth factors; better localise and control the delivery of the growth factor at the site of treatment; and boost either cellular sensitivity to the growth factor or to the factors signalling efficiency.

Having described the development of HS16+ve, and its ability to potentiate the TGF-β1-driven SMAD response in MSC monolayer cultures, we hypothesised that it could be used to improve cartilage healing by sequestering endogenous TGF-β1. We thus sought to examine its effects on (1) the chondrogenic differentiation of hMSCs in vitro; and (2) the cartilage-healing response in a rabbit model.

This Example describes the use of a modified micromass pellet culture system for the examination of the in vitro effects of HS16+ve on the chondrogenic differentiation of hMSCs. It then moves on to examine the effects of the previously described HS variants, when used in conjunction with the current clinical "standard of care", within a full depth, osteochondral defect of the trochlea groove in a rabbit model for cartilage repair.

Materials and Methods

Reverse Transcription and Quantitative PCR (qPCR)

Total RNA was isolated from chondrogenic micromass pellets using TRIZOL reagent (Life Technologies, CA, USA) according to the manufacturer's protocol. Reverse transcription was carried out on 1 μg RNA using the SuperScript® VILO™ cDNA Synthesis Kit (Life Technologies) following the manufacturer's instructions, with the incubation at 42° C. being carried out for 2 h instead of 1 h. Each qPCR contained 40 ng cDNA, 1 μL TaqMan® primer-probe mix per gene, and 10 μL Taqman® Fast Universal PCR Master Mix (Life Technologies) in a final volume of 20 μL. Thermal cycling conditions were 95° C. for 20 s, followed by 45 cycles of 95° C. for 1 s and 60° C. for 20 s. Each qPCR was run in duplicate and gene expression was normalised to HPRT1 expression to obtain the ΔCt value. The average value of biological triplicates was taken. Chondrogenic micromass pellets cultured in media without GAG or TGF-β1 were used as controls (ΔΔCt). Relative expression levels for each primer set were expressed as fold changes by the 2-ΔΔCt method [Livak, K. J. and T. D. Schmittgen, *Analysis of Relative Gene Expression Data Using Real-Time Quantitative PCR and the 2-ΔΔCT Method.* Methods, 2001. 25(4): p. 402-408]. The following TaqMan® primer-probe assays (Life technologies) were used:

In Vivo Study Design

Twenty-two skeletally mature, male New Zealand White rabbits (average age 9 months and body weight 3.9 kg) were used for this study. All rabbits received bilateral osteochondral defects in the femoral trochlea groove and each defect randomly assigned to one of four treatment groups: (1) Gel alone, (2) Gel+HSPM, (3) Gel+HS16+ve, and (4) Gel+ HS16−ve. Every defect received 60 μL of a hyaluronic acid-based hydrogel (Gel) (AuxiGel™, Termira AB, Stockholm, Sweden) [Bergman, K., et al., *Injectable cell-free template for bone-tissue formation.* Journal of Biomedical Materials Research Part A, 2009. 91A(4): p. 1111-1118.] alone or with 10 μg of HSPM, HS16+ve or HS16−ve. Two rabbits died from gastric stasis postsurgery and were not included in the analysis.

Defect Creation and Gel Injection

The research protocol used for this study was approved by the Institutional Animal Care and Use Committee, A*STAR Singapore, and followed all appropriate guidelines. All surgical procedures were carried out under general anaesthesia, consisting of a combination of ketamine (35 mg/kg) and xylazine (5 mg/kg) injections and isoflurane via a face mask, and aseptic conditions. A medial para-patellar skin incision of 15-20 mm was made and the patella dislocated laterally. One full thickness, critically-sized osteochondral defect (4 mm diameter, 2 mm depth) was made in the centre of each femoral trochlea groove with complete debridement of the calcified cartilage. Subsequently, 3 microfractures (0.8 mm diameter, 2 mm depth) were made in each defect using an orthopaedic drill and direct pressure applied with surgical gauze to ensure all bleeding had stopped prior to the application of the designated treatment. Treatments were applied with a 200 μL pipette and allowed to set. All defects were observed to fill with blood while the gel carrier was setting.

Once the gel carrier had set, the patella was repositioned and the joint flexed 15 times to ensure the treatment remained in place before the incision was closed in layers, and rabbits allowed to weight-bear. The wound site was further sealed with Vetbond™ tissue adhesive (3M, MN, USA). Prophylactic antibiotics (Enrofloxacin, 10 mg/kg) and analgesics (Buprenorphin, 0.1 mg/kg) were administered subcutaneously for 5 days postsurgery. At 12 weeks all rabbits were euthanized with pentobarbital (150 mg/kg) after sedation. Distal femurs were harvested and imaged macroscopically before being processed for histological and immunohistochemistry (IHC) analysis.

Gross Pathologic Observation of Joints

Images of the joints were examined and scored by a blinded observer unaware of the treatment groups. Macroscopic scoring was based on the International Cartilage Repair Society (ICRS) Visual Assessment Scale (ICRS I scoring system) [Brittberg, M. and L. Peterson, *Introduction of an articular cartilage classification.* ICRS Newsletter, 1998. 1: p. 5-8.].

Histology Analyses

Harvested distal femoral heads were fixed in 10% (v/v) neutral-buffered formalin (NBF) for 1 week under vacuum and decalcified in 5% (v/v) formic acid at room temperature for an average of 6-7 days. The samples were subsequently embedded in paraffin wax and sectioned (5 µm) across the middle of the defect. Sections were deparaffinised and stained with Masson's trichrome, Alcian blue (pH 1, counterstained with neutral red) and Safranin-O.

Immunohistochemistry (IHC) Analyses

IHC staining was carried out using either the Leica Bond™-III or the Leica Bond™-Max Autostainer (Leica Nussloch GmbH, Germany) and the Bond™ Refine Detection Kit (Leica). Sections were deparaffinised with Bond™ Dewax solution (Leica) and antigen retrieval carried out by incubating with Proteinase K (20 µg/mL) (Sigma-Aldrich) for 15 min at room temperature. Endogenous peroxidase activity blocked by incubating with 3-4% (v/v) $H_2O_2$ for 15 min. Sections were then blocked in 10% (v/v) goat serum for 30 min before incubation with primary antibody (Collagen Type I (1:1000), Novus Biologicals, CO, USA and Collagen Type 11 (1:2000), Acris Antibodies, Inc., CA, USA) diluted in Bond™ Primary Antibody Diluent (Leica) for 30 min at room temperature. Detection of staining was carried out as described in the Bond™ Refine Detection Kit and nuclei were counterstained with haematoxylin for 5 min. All washes were carried out with 1× Bond™ Wash Solution (Leica).

Histological Scoring

Examination and scoring of stained sections was carried out by a masked observer unaware of the treatment groups. Scoring was based on the O'Driscoll [O'Driscoll, S. W., F. W. Keeley, and R. B. Salter, *The chondrogenic potential of free autogenous periosteal grafts for biological resurfacing of major full thickness defects in joint surfaces under the influence of continuous passive motion. An experimental investigation in the rabbit.* J Bone Joint Surg Am, 1986. 68(7): p. 1017-1035] and ICRS II [Mainil-Varlet, P., et al., *A New Histology Scoring System for the Assessment of the Quality of Human Cartilage Repair: ICRS II*. The American Journal of Sports Medicine, 2010] scoring systems, and tissue filling was determined by quantifying the percentage of each tissue type (i.e. bony tissue, fibrous tissue, fibrocartilage, hybrid cartilage and hyaline cartilage) within the chondral and sub-chondral space.

Results

Effects of HS16+ve on Chondrogenic Differentiation of hMSCs In Vitro

In order to assess the effects of HS16+ve on the chondrogenic differentiation of hMSCs in vitro, it was first necessary to establish the effects of TGF-β1 alone. Chondrogenic differentiation was carried out using a modified micromass culture system. [Zhang, L., et al., *Chondrogenic differentiation of human mesenchymal stem cells: a comparison between micromass and pellet culture systems.* Biotechnol Lett, 2010. 32(9): p. 1339-1346.]. Briefly, passage 4 hMSCs were harvested and resuspended in chemically defined chondrogenic media (PT-3003, Lonza, MD, USA) at $2 \times 10^7$ cells/mL. Droplets of 12.5 µL were then seeded into the middle of each well in a 24-well plate and left to adhere at 37° C. for 2 h, after which, 500 µL of chondrogenic media supplemented with either 1 or 10 ng/mL of TGF-β1 (100-210, PeproTech) alone or with either 5 or 10 µg/mL of heparin (Sigma-Aldrich), porcine mucosal HS (HSPM) (Celsus laboratories), HS16+ve or HS16-ve was added to each well. The cell droplets coalesced into spherical masses after 24 h. Media was changed every 3 days and the micromasses harvested on days 3, 7, 14 and 21.

Figure 15:
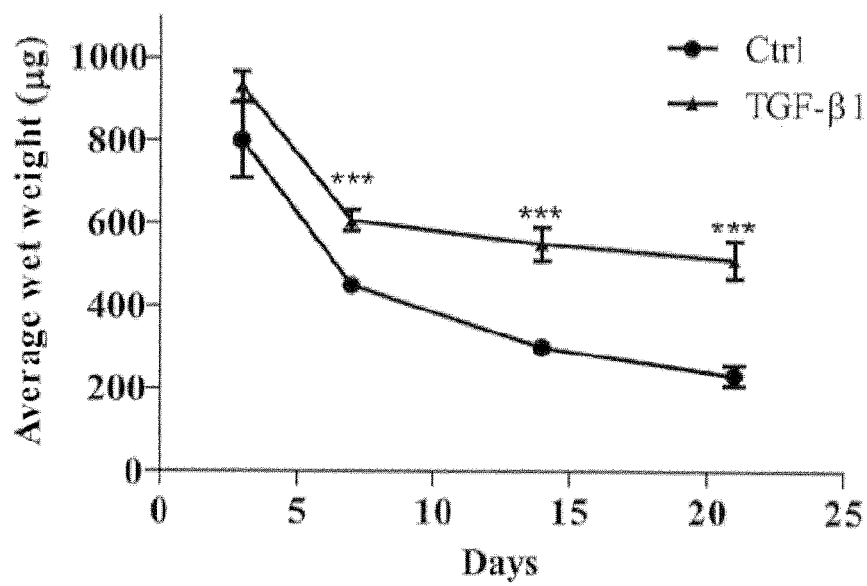
FIG. 15. Wet weight change in differentiating hMSCs. Graph showing the change in weights of chondrogenically differentiated pellets treated with (TGF-β1) or without TGF-β1 (Ctrl) over time. Errors bars represent SD, n=3. *** P<0.001 compared to Ctrl.

Wet weights of the resulting control (Ctrl) and TGF-β1-treated (10 ng/mL) (TGF-β1) micromass pellets were taken at days 3, 7, 14 and 21 (FIG. 15). While the weights of pellets in either treatment group decreased over time, the weight loss was less pronounced in TGF-β1-treated pellets than control pellets.

Figure 16A:
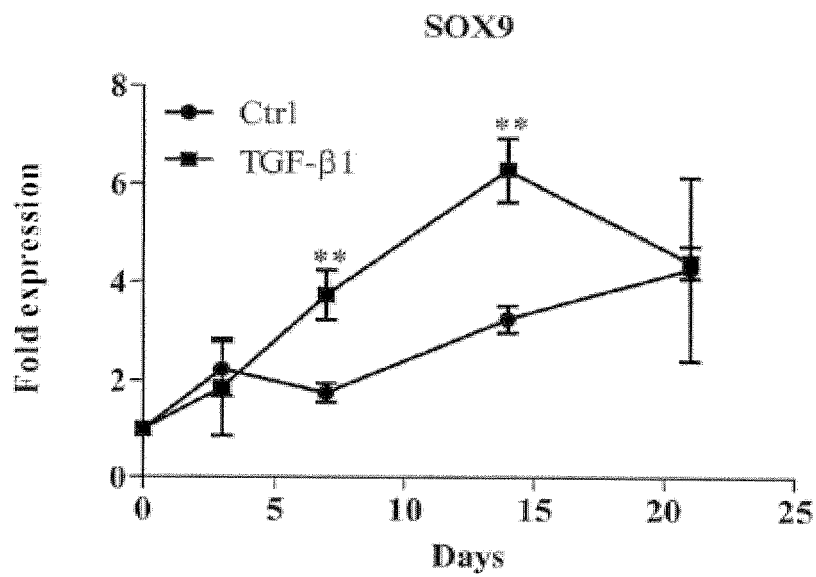
FIG. 16A to 16E. Chondrogenic gene expression in differentiating hMSCs. Graphs showing (A) SOX9, (B) COMP, (C) Aggrecan, (D) Collagen type 2α1, and (E) Collagen type 10α1 mRNA expression levels over time in pellets treated with (TGF-β1) or without (Ctrl) 10 ng/mL TGF-β1. Collagen type 2α1 mRNA was not detected in Ctrl pellets. Error bars represent SD, n=3. * P<0.05,  P<0.01, * P<0.001 compared to Ctrl.
Figure 16B:
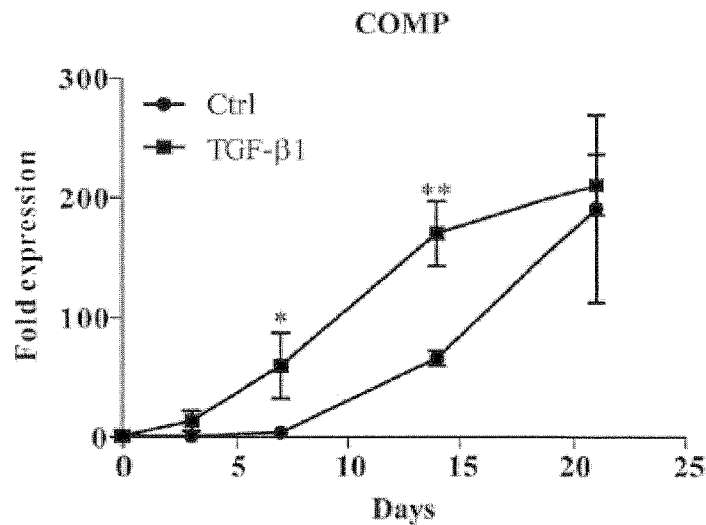
Figure 16C:
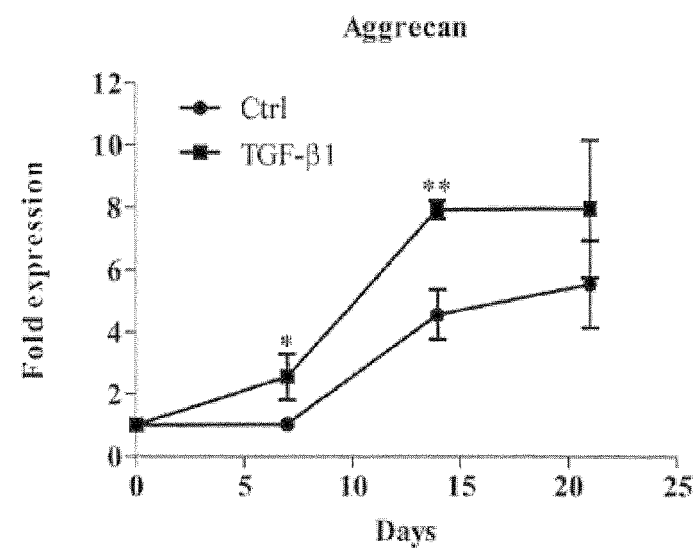
Figure 16D:
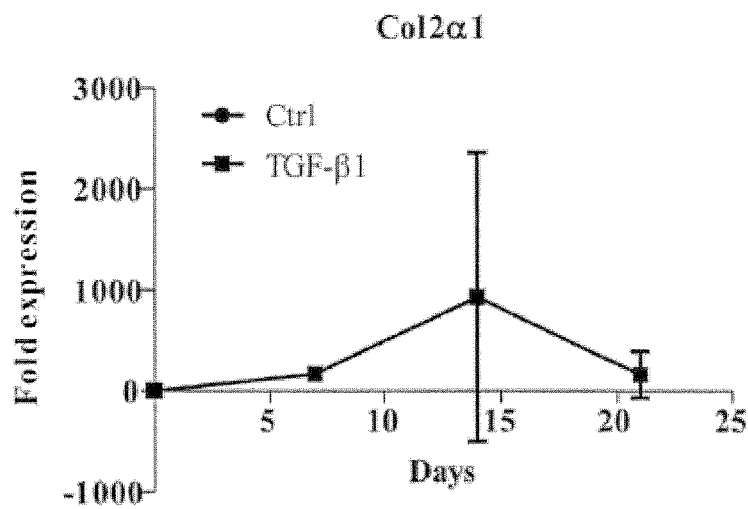
Figure 16E:
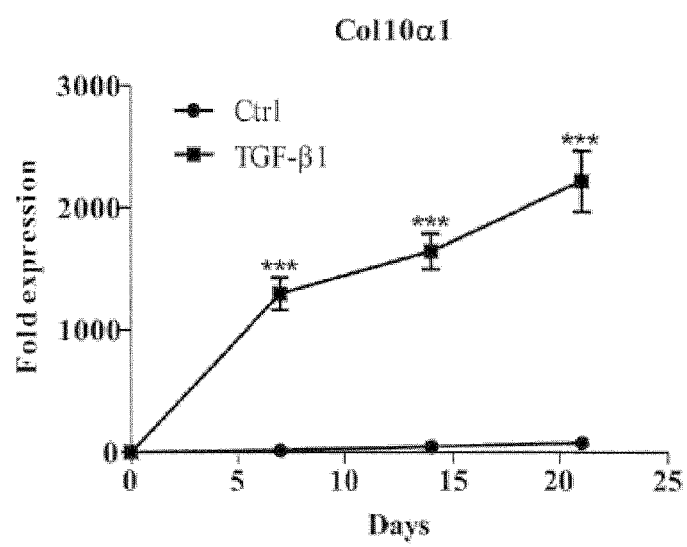

Gene expression analysis of the micromass pellets at days 3 (SOX9 and COMP only), 7, 14 and 21 revealed that treatment with 10 ng/mL TGF-β1 (TGF-β1) consistently led to the increased expression of the chondrogenic markers SOX9 (FIG. 16A), COMP (FIG. 16B) and aggrecan (FIG. 16C) relative to untreated control pellets (Ctrl). Undifferentiated hMSCs were used as the day 0 control. Type II collagen transcripts were only detectable in TGF-β1-treated pellets and undifferentiated hMSCs (FIG. 16C). This appears to suggest that hMSCs express low levels of type II collagen transcripts when grown in monolayers, but this expression is lost when they are cultured as micromasses in chondrogenic medium without TGF-β1. Finally, TGF-β1-treated pellets were found to express extremely high levels of type X collagen transcripts, a marker of chondrocyte hypertrophy, relative to control pellets (FIG. 16E). Such high expression levels suggest that the pellets are undergoing chondrogenic hypertrophy as a prelude to endochondral ossification [Shen, G., *The role of type X collagen in facilitating and regulating endochondral ossification of articular cartilage.* Orthodontics & Craniofacial Research, 2005. 8(1): p. 11-17].

Histological examination of the paraffin-embedded pellets at day 21 by Alcian blue staining, which stains GAGs blue, revealed that TGF-β1-treated pellets contained more GAGs then control pellets.

Figure 17A:
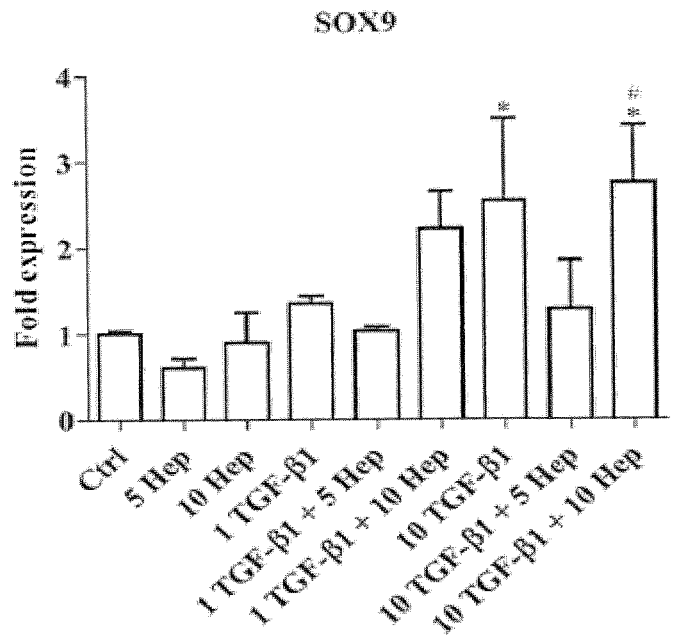
FIGS. 17A and 17B. Effect of heparin on early chondrogenic gene expression. Bar charts showing (A) SOX9 and (B) COMP mRNA expression levels in hMSCs after 3 days of differentiation in chondrogenic media with the indicated treatments. Ctrl—control; 5 Hep—5 μg/mL heparin; 10 Hep—10 μg/mL heparin; 1 TGF-β1—1 ng/mL TGF-β1; 10 TGF-β1—10 ng/mL TGF-β1. Error bars represent SD, n=3. * P<0.05, *** P<compared to Ctrl. # P<0.05, ### P<0.001 compared to 1 TGF-β1.
Figure 17B:
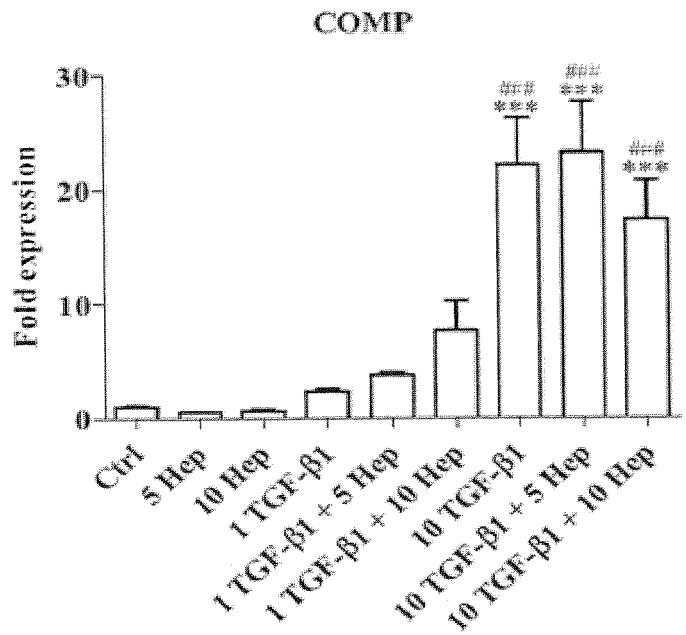

Having established the effects of TGF-β1 on the chondrogenic differentiation of hMSCs, we next sought to examine the effects that heparin has, before embarking on the investigation of the effects of HS16+ve. In Example 1 we showed that heparin was able to potentiate the TGF-β1-driven pSMAD signal in hMSCs at 6 h post treatment. Since medium was changed every third day during the chondrogenic differentiation process, we chose to use a day 3 time point to examine the effects of heparin on the expression of SOX9 and COMP, both early chondrogenic markers [Barry, F., et al., *Chondrogenic Differentiation of Mesenchymal Stem Cells from Bone Marrow: Differentiation-Dependent Gene Expression of Matrix Components.* Exp Cell Res, 2001. 268(2): p. 189-200; Li, H., et al., *Comparative analysis with collagen type II distinguishes cartilage oligomeric matrix protein as a primary TGFβ-responsive gene.* Osteoarthritis Cartilage, 2011. 19(10): p. 1246-1253; Huang, A. H., A. Stein, and R. L. Mauck, *Evaluation of the Complex Transcriptional Topography of Mesenchymal Stem Cell Chondrogenesis for Cartilage Tissue Engineering.* Tissue Eng Part A, 2010. 16(9): p. 2699-708; Zaucke, F., et al., *Cartilage oligomeric matrix protein (COMP) and collagen IX are sensitive markers for the differentiation state of articular primary chondrocytes.* Biochem J, 2001. 358(1): p. 17-24.]. We also reasoned that if heparin were to potentiate the effects of the TGF-β1, further increases in the response to the recommended dose of 10 ng/mL might not be detectable. Therefore, a lower dose of TGF-β1 was used in parallel with the recommended dose. Our data show that 5 µg/mL of heparin did not significantly alter the level of SOX9 expression regardless of the amount of TGF-β1 used (FIG. 17A). Conversely, 10 µg/mL of heparin on its own did not affect SOX9 expression, but when used in concert with 1 ng/mL of TGF-β1, it was able to increase the expression of SOX9. The same dose of heparin was unable to bring about any change in SOX9 expression when used with 10 ng/mL of TGF-β1, suggesting that the TGF-β1 signal was already saturated. In the case of COMP expression, both doses of heparin on their own were found to slightly reduce it (FIG. 17B). However, when used in combination with 1 ng/mL TGF-β1, heparin was able to increase COMP expression levels in a dose dependent manner. The use of either dose of heparin with 10 ng/mL of TGF-β1 was unable to elicit a further increase in COMP expression. In fact, the higher dose of heparin actually reduced COMP expression levels. This again suggests that 10 ng/mL of TGF-β1 is a saturating dose for hMSCs undergoing chondrogenic differentiation. The reduction in COMP expression seen when 10 μg/mL of heparin was used with 10 ng/mL of TGF-β1 suggests the activation of a negative feedback mechanism in response to an excessive TGF-β1 signal.

A dose of 10 μg/mL of GAG was selected to be used in conjunction with a 1 ng/mL dose of TGF-β1. Histological analysis of pellets cultured with either 1 ng/mL TGF-β1, 1 ng/mL TGF-β1 and 10 μg/mL heparin or 10 ng/mL TGF-β1 for 21 days showed that the higher dose of TGF-β1 lead to an increase in GAG production and deposition, based on Alcian blue staining. The use of heparin with TGF-β1 led to a slight increase in GAG deposition relative to 1 ng/mL of TGF-β1 alone, but this increase was still less than that seen with 10 ng/mL of TGF-β1.

Next, hMSCs were differentiated for 21 days in the presence of 1 ng/mL TGF-β1 alone (1 TGF-β1) or in combination with 10 μg/mL of GAG (heparin, HSPM, HS16+ve or HS16−ve) or with 10 ng/mL TGF-β1 (10 TGF-β1) as a positive control.

Figure 18A:
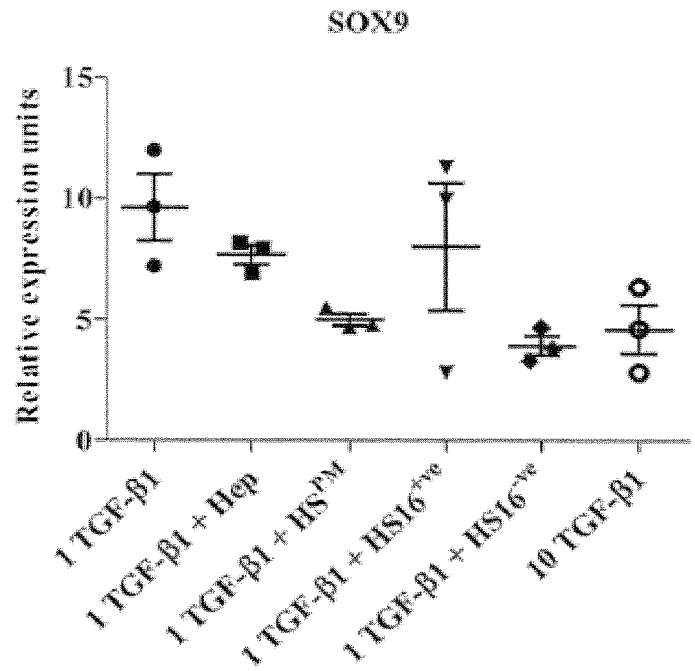
FIG. 18A to 18D. Effect of isolated HS fractions on chondrogenic gene expression of hMSCs. Scatterplots showing (A) SOX9, (B) COMP, (C) Aggrecan and (D) Collagen type 10α1 mRNA expression levels in pellets cultured for 21 days in chondrogenic media with 1 or 10 ng/mL TGF-β1 (1 TGF-β1 and 10 TGF-β1, respectively) and 10 μg/mL of the indicated GAG. Collagen type 2α1 mRNA was only detected in pellets treated with 10 ng/mL TGF-β1. Middle line represents mean, while error bars represent SD, n=3. * P<0.05, *** P<0.001, compared to 1 TGF-β1. Note the outlier present in the 1 TGF-β1+HS16+ve dataset.
Figure 18B:
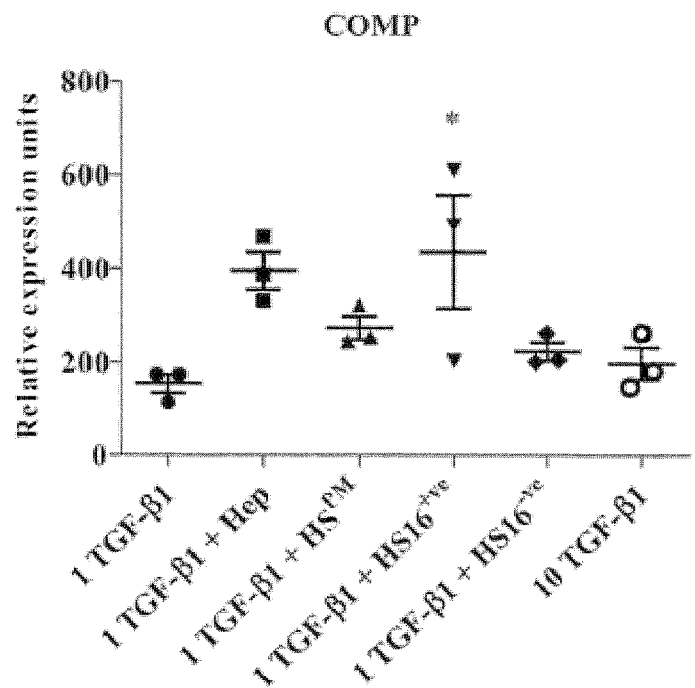

Analysis of SOX9 mRNA expression at 21 days showed that all the sugars used did not produce significant changes (FIG. 18A). COMP expression increased ~2.5 fold, relative to 1 ng/mL TGF-β1 alone, when pellets were cultured with heparin or HS16+ve (P<0.05) in conjunction with 1 ng/mL TGF-β1 (FIG. 18B). Culture in medium supplemented with low (1 ng/mL) TGF-β1 and either HSPM or HS16−ve, or supplemented with high (10 ng/mL) TGF-β1 did not significantly alter COMP expression relative to low dose TGF-β1 alone.

Figure 18C:
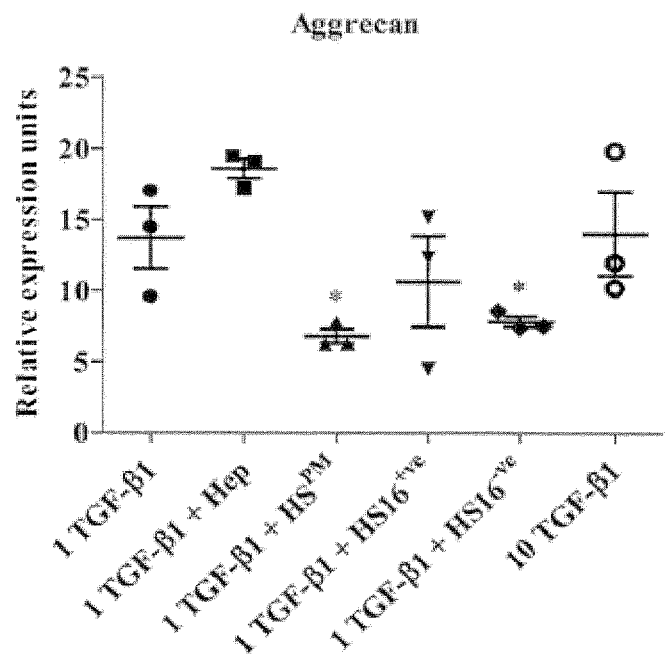
Figure 18D:
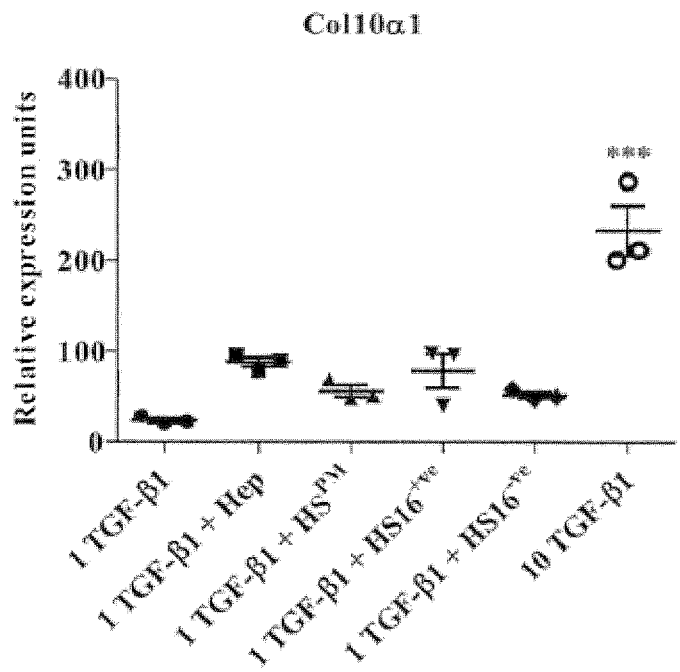

Aggrecan expression was similar with low and high doses of TGF-β1 and heparin and HS16+ve at day 21 (FIG. 18C). However, culture with HSPM and HS16−ve reduced aggrecan transcript levels. High TGF-β1 induced a significant increase (P<0.001) in type X collagen expression relative to low TGF-β1 (FIG. 18D). Treatment with GAGs did not significantly alter type X collagen expression relative to low TGF-β1. Type II collagen transcripts were only detected in pellets treated with high TGF-β1 and are thus not shown here. It should be noted that the high variance seen in all the samples treated with HS16+ve stemmed from the presence of an outlier within the dataset.

Histological examination of the pellets by Alcian blue staining at day 21 did not indicate significant differences between the pellets cultured with the various sugars, relative to low TGF-β1. High TGF-β1 did however induce a modest increase in GAG production compared to low TGF-β1.

Effects of HS16 on Chondrogenic Differentiation of MSCs In Vivo

Skeletally mature adult New Zealand white rabbits were chosen for our in vivo trial based both on their extensive use in cartilage repair studies, and to avoid the spontaneous healing observed in juveniles. We opted to trial our compound in a model comprising a full depth osteochondral defect in the femoral trochlea groove, where microfracture is used with a commercially available hyaluronic acid-based hydrogel (AuxiGel™, Termira AB) [Bergman, K., et al., *Injectable cell-free template for bone-tissue formation*. Journal of Biomedical Materials Research Part A, 2009. 91A(4): p. 1111-1118], based on guidelines outlined by Reinholz et al. [Reinholz, G. G., et al., *Animal models for cartilage reconstruction*. Biomaterials, 2004. 25(9): p. 1511-1521], the ICRS [Hurtig, M. B., et al., *Preclinical Studies for Cartilage Repair: Recommendations from the International Cartilage Repair Society*. Cartilage, 2011. 2(2): p. 137-152] and current standard-of-care practices in hospitals [Fritz, J., et al., *Articular cartilage defects in the knee-basics, therapies and results*. Injury, 2008. 39(1, Supplement): p. 50-57; Hunziker, E. B., *Articular cartilage repair: basic science and clinical progress. A review of the current status and prospects*. Osteoarthritis Cartilage, 2002. 10(6): p. 432-463].

Sequence alignment of rabbit and human TGF-β1 revealed that TGF-β1 was not only highly conserved across both species, but the identified heparin-binding domain was nearly identical (FIG. 19). Mean levels of TGF-β1 in the joint fluid of rabbits have been found to range from 112.7 pg/mL in young rabbits to 52.3 pg/mL in adult rabbits [Wei, X. and K. Messner, *Age-and injury-dependent concentrations of transforming growth factor-β1 and proteoglycan fragments in rabbit knee joint fluid*. Osteoarthritis and Cartilage, 1998. 6(1): p. 10-18.], while levels in anti-coagulated bone marrow aspirate were found to range from 190-881.8 pg/mL in adult rabbits (n=20) (Lim, Z. X. H., unpublished data). Separate studies have also reported increases in TGF-β1 of up to nanogram levels after platelet activation [Coupes, S. M., et al., *Plasma transforming growth factor β1 and platelet activation: implications for studies in transplant recipients*. Nephrol Dial Transplant, 2001. 16(2): p. 361-367], and the presence of sufficient levels of TGF-β1 in the wound to stimulate cartilage repair [Shah. R. N., et al., *Supramolecular design of self-assembling nanofibers for cartilage regeneration*. Proc Natl Acad Sol USA, 2010. 107(8): p. 3293-3298]. As such, the use of exogenous TGF-β1 with our sugar treatments was precluded.

A 12-week study was performed comparing the following groups: (1) control group treated with 60 μL of hydrogel (Gel alone) per defect: (2) defects treated with 60 μL of hydrogel and 10 μg of HSPM (HSPM); (3) defects treated with 60 μL hydrogel and 10 μg of HS16+ve (HS16+ve), and (4) defects treated with 60 μL hydrogel and 10 μg of HS16−ve (HS16−ve). Based on our earlier work, 10 μg/mL of GAG was determined to be optimal for enhancing the effects of 1 ng/mL of TGF-β1. As such, it was decided that a dose of 10 μg of GAG would be sufficient to achieve this optimal concentration within the defect, even after accounting for possible diffusion within the synovial cavity. Defects were created as described above. Two rabbits died of gastric stasis before the end of the trial and were therefore excluded from the analysis.

At the end of the trial, whole femurs were harvested from the rabbits, fixed in 10% (v/v) NBF and imaged macroscopically before being decalcified and processed for histology. Macroscopic observation of defects after 12 weeks revealed a slight difference between the control (Gel alone) and treatment groups with regard to tissue filling. While there was an equal amount of variation in tissue filling within each treatment group, more defects in the control group were incompletely filled relative to those in the other groups. The median scores of the groups treated with HSPM, HS16+ve and HS16−ve were higher than those of Gel alone (FIG. 20B), suggesting that the use HS16+ve might improve the consistency of the healing response.

Histological scores from the O'Driscoll and ICRS II scoring systems showed no significant differences between the treatment groups. Tissue filling of the defect was determined by first identifying the borders of the chondral and sub-chondral spaces, superimposing a grid over the imaged sections and then measuring the amount of space filled for each histological space. In terms of tissue filling, nearly all the samples exhibited complete subchondral filling and high levels of chondral filling. There were no statistical differences between the tissue filling scores for all the treatment groups. The median percentage of sub-chondral filling in all samples was similar. All three compounds (HSPM, HS16−ve and HS16+ve) had median tissue filling scores that were higher than control samples (Gel), which is the current clinical standard-of-care treatment.

The in vitro data indicate that HS16+ve was able to enhance the TGF-β1-induced expression of a number of chondrogenic markers, relative to HSPM and HS16−ve. This suggests that it may be necessary to pre-load, e.g. coat or impregnate, gel-constructs with HS and TGFβ1 prior to implantation.

The in vivo data show that treatment of full depth osteochondral defects with a single dose of sugar, in conjunction with microfracture and hydrogel implantation, is at least as good as the current standard-of-care treatment, and does not produce undesired side effects. HS16+ve had median scores in the in vivo data that were higher than control samples (Gel), which is the current clinical standard-of-care treatment.

The invention claimed is:

1. A method of treating a disease, condition or injury to tissue in a patient, the method comprising administration of a therapeutically effective amount of heparan sulphate HS16 to the patient leading to repair or regeneration of the tissue, wherein the heparan sulphate HS16 consists of heparan sulfate chains isolated from their core protein, which binds to a peptide or polypeptide consisting of the amino acid sequence RKDLGWKWIHEPKGYH (SEQ ID NO:1), wherein the disease, condition or injury to tissue is treatable by the growth, proliferation, or differentiation of new tissue; and the disaccharide composition of heparan sulphate HS16, following digestion with heparin lyases I, II and III and then subjecting the resulting disaccharide fragments to HPLC analysis, comprises:

| Disaccharide | Normalised weight percentage |
|---|---|
| ΔUA,2S-GlcNS,6S | 14.75 ± 3.0 |
| ΔUA,2S-GlcNS | 4.58 ± 2.0 |
| ΔUA-GlcNS,6S | 12.98 ± 3.0 |
| ΔUA-GlcNS | 22.24 ± 3.0 |
| ΔUA,2S-GlcNAc | 0.56 ± 0.5 |
| ΔUA-GlcNAc,6S | 12.63 ± 3.0 |
| ΔUA-GlcNAc | 32.26 ± 3.0. |

2. The method of claim 1, wherein the heparan sulphate HS16is administered to tissue at or surrounding a wound or at a location on the patient's body at which regeneration or repair of tissue is required.

3. The method of claim 1, wherein the method further comprises administering TGβ1protein to the patient.

4. A method of treating a disease, condition or injury to tissue in a patient, the method comprising surgically implanting a biocompatible implant or prosthesis, which implant or prosthesis comprises a biomaterial and heparan sulphate HS16, into tissue of the patient at or surrounding the site of the disease, condition or injury leading to repair or regeneration of the tissue, wherein the heparan sulphate HS16consists of heparan sulfate chains isolated from their core protein, which binds to a peptide or polypeptide consisting of the amino acid sequence RKDLGWKWIHEPKGYH (SEQ ID NO:1), wherein the disease, condition, or injury to tissue is treatable by growth, proliferation, or differentiation of new tissue; and the disaccharide composition of heparan sulphate HS16, following digestion with heparin lyases I, II and III and then subjecting the resulting disaccharide fragments to HPLC analysis, comprises:

| Disaccharide | Normalised weight percentage |
|---|---|
| ΔUA,2S-GlcNS,6S | 14.75 ± 3.0 |
| ΔUA,2S-GlcNS | 4.58 ± 2.0 |
| ΔUA-GlcNS,6S | 12.98 ± 3.0 |
| ΔUA-GlcNS | 22.24 ± 3.0 |
| ΔUA,2S-GlcNAc | 0.56 ± 0.5 |
| ΔUA-GlcNAc,6S | 12.63 ± 3.0 |
| ΔUA-GlcNAc | 32.26 ± 3.0. |

5. The method of claim 1, wherein the disaccharide composition of heparan sulphate HS16, following digestion with heparin lyases I, II and III and then subjecting the resulting disaccharide fragments to HPLC analysis, comprises:

| Disaccharide | Normalised weight percentage |
|---|---|
| ΔUA,2S-GlcNS,6S | 14.75 ± 1.0 |
| ΔUA,2S-GlcNS | 4.58 ± 0.4 |
| ΔUA-GlcNS,6S | 12.98 ± 1.0 |
| ΔUA-GlcNS | 22.24 ± 1.6 |
| ΔUA,2S-GlcNAc | 0.56 ± 0.4 |
| ΔUA-GlcNAc,6S | 12.63 ± 1.0 |
| ΔUA-GlcNAc | 32.26 ± 1.6. |

6. The method of claim 1, wherein the heparan sulphate HS16is obtained by a method comprising:

(i) providing a solid support having polypeptide molecules adhered to the support, wherein the polypeptide comprises a heparin-binding domain having the amino acid sequence RKDLGWKWIHEPKGYH (SEQ ID NO:1);

(ii) contacting the solid support with a mixture comprising glycosaminoglycan such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes; and (v) collecting the dissociated glycosaminoglycans.

7. The method of claim 1, wherein administration is by injection.

8. The method of claim 1, wherein the heparan sulphate HS16is formulated for administration by injection.

9. The method of claim 1, wherein the heparan sulphate HS16is formulated with a pharmaceutically acceptable carrier, adjuvant, excipient or diluent.

10. The method of claim 1, wherein the tissue is a connective tissue selected from cartilage, bone, tendon, ligament, skin, and corneal tissue.

11. The method of claim 1, wherein the tissue is cartilage or bone tissue.

12. The method of claim 1, wherein the disease, condition or injury to tissue in a patient is arthritis.

13. The method of claim 1, wherein the disease, condition or injury to tissue in a patient is an osteochondral defect.

14. The method of claim 4, wherein the disaccharide composition of heparan sulphate HS16, following digestion with heparin lyases I, II and III and then subjecting the resulting disaccharide fragments to HPLC analysis, comprises:

| Disaccharide | Normalised weight percentage |
|---|---|
| ΔUA,2S-GlcNS,6S | 14.75 ± 1.0 |
| ΔUA,2S-GlcNS | 4.58 ± 0.4 |
| ΔUA-GlcNS,6S | 12.98 ± 1.0 |
| ΔUA-GlcNS | 22.24 ± 1.6 |
| ΔUA,2S-GlcNAc | 0.56 ± 0.4 |
| ΔUA-GlcNAc,6S | 12.63 ± 1.0 |
| ΔUA-GlcNAc | 32.26 ± 1.6. |

15. The method of claim 4, wherein the biomaterial is coated or impregnated with the heparan sulphate HS16.

16. The method of claim 4, wherein the biocompatible implant or prosthesis is formed by a method comprising the step of coating or impregnating a biomaterial with the heparan sulphate HS16.

17. The method of claim 4, wherein the biomaterial comprises a collagen matrix.

18. The method of claim 4, wherein the tissue is a connective tissue selected from cartilage, bone, tendon, ligament, skin, and corneal tissue.

19. The method of claim 4, wherein the tissue is cartilage or bone tissue.

20. The method of claim 4, wherein the heparan sulphate HS16 is obtained by a method comprising:
   (i) providing a solid support having polypeptide molecules adhered to the support, wherein the polypeptide comprises a heparin-binding domain having the amino acid sequence RKDLGWKWIHEPKGYH (SEQ ID NO:1);
   (ii) contacting the solid support with a mixture comprising glycosaminoglycan such that polypeptide-glycosaminoglycan complexes are allowed to form;
   (iii) partitioning polypeptide-glycosaminoglycan complexes from the remainder of the mixture;
   (iv) dissociating glycosaminoglycans from the polypeptide-glycosaminoglycan complexes; and
   (v) collecting the dissociated glycosaminoglycans.

* * * * *

SEQUENCE LISTING

```
<160> NUMBER OF SEQ ID NOS: 17

<210> SEQ ID NO 1
<211> LENGTH: 16
<212> TYPE: PRT
<213> ORGANISM: Homo sapiens

<400> SEQUENCE: 1

Arg Lys Asp Leu Gly Trp Lys Trp Ile His Glu Pro Lys Gly Tyr His
1               5                   10                  15

<210> SEQ ID NO 2
<211> LENGTH: 390
<212> TYPE: PRT
<213> ORGANISM: Homo sapiens

<400> SEQUENCE: 2

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
```

```
                210               215               220
Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
                260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
                340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 3
<211> LENGTH: 112
<212> TYPE: PRT
<213> ORGANISM: Homo sapiens

<400> SEQUENCE: 3

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 4
<211> LENGTH: 99
<212> TYPE: PRT
<213> ORGANISM: Oryctolagus cuniculus

<400> SEQUENCE: 4

Phe Ser Thr Asn Tyr Cys Phe Ser Ser Thr Glu Lys Asn Cys Cys Val
1               5                   10                  15

Arg Gln Leu Tyr Ile Asp Phe Arg Lys Asp Leu Gly Trp Lys Trp Ile
                20                  25                  30

His Glu Pro Lys Gly Tyr His Ala Asn Phe Cys Leu Gly Pro Cys Pro
```

```
                35                  40                  45
Tyr Ile Trp Ser Leu Asp Thr Gln Tyr Ser Lys Val Leu Ala Leu Tyr
         50                  55                  60

Asn Gln His Asn Pro Gly Ala Ser Ala Ala Pro Cys Cys Val Pro Gln
 65                  70                  75                  80

Ala Leu Glu Ala Thr Ala His Arg Val Thr Thr Leu Gly Arg Lys Pro
                 85                  90                  95

Lys Val Glu

<210> SEQ ID NO 5
<211> LENGTH: 4
<212> TYPE: PRT
<213> ORGANISM: Homo sapiens

<400> SEQUENCE: 5

Phe Trp Tyr Leu
1

<210> SEQ ID NO 6
<211> LENGTH: 4
<212> TYPE: PRT
<213> ORGANISM: Homo sapiens

<400> SEQUENCE: 6

Phe Trp Tyr Pro
1

<210> SEQ ID NO 7
<211> LENGTH: 18
<212> TYPE: PRT
<213> ORGANISM: Artificial sequence
<220> FEATURE:
<223> OTHER INFORMATION: Synthetic TGF-beta1-derived peptide
<220> FEATURE:
<221> NAME/KEY: MOD_RES
<222> LOCATION: (17)..(17)
<223> OTHER INFORMATION: Acp
<220> FEATURE:
<221> NAME/KEY: SITE
<222> LOCATION: (18)..(18)
<223> OTHER INFORMATION: Xaa is Lys(Biotin)

<400> SEQUENCE: 7

Arg Lys Asp Leu Gly Trp Lys Trp Ile His Glu Pro Lys Gly Tyr His
1               5                  10                  15

Lys Lys

<210> SEQ ID NO 8
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: Cys(carbamidomethyl) in Peptide 1
<220> FEATURE:
<221> NAME/KEY: SITE
<222> LOCATION: (7)..(7)
<223> OTHER INFORMATION: Lys(biotin) in Peptide 1
<220> FEATURE:
<221> NAME/KEY: SITE
<222> LOCATION: (9)..(9)
<223> OTHER INFORMATION: Cys(carbamidomethyl) in Peptide 1
<220> FEATURE:
<221> NAME/KEY: SITE
<222> LOCATION: (10)..(10)
<223> OTHER INFORMATION: Cys(carbamidomethyl) in Peptide 1
```

-continued

```
<400> SEQUENCE: 8

Cys Phe Ser Ser Thr Glu Lys Asn Cys Cys Val Arg Gln Leu Tyr
1               5                   10                  15

<210> SEQ ID NO 9
<211> LENGTH: 9
<212> TYPE: PRT
<213> ORGANISM: Homo sapiens
<220> FEATURE:
<221> NAME/KEY: SITE
<222> LOCATION: (5)..(5)
<223> OTHER INFORMATION: Lys(biotin) in Peptide 2

<400> SEQUENCE: 9

Ile Asp Phe Arg Lys Asp Leu Gly Trp
1               5

<210> SEQ ID NO 10
<211> LENGTH: 8
<212> TYPE: PRT
<213> ORGANISM: Homo sapiens
<220> FEATURE:
<221> NAME/KEY: SITE
<222> LOCATION: (2)..(2)
<223> OTHER INFORMATION: Lys(biotin) in Peptide 3
<220> FEATURE:
<221> NAME/KEY: SITE
<222> LOCATION: (2)..(2)
<223> OTHER INFORMATION: Lys(acetyl) in Peptide 4
<220> FEATURE:
<221> NAME/KEY: SITE
<222> LOCATION: (7)..(7)
<223> OTHER INFORMATION: Lys(biotin) in Peptide 4
<220> FEATURE:
<221> NAME/KEY: SITE
<222> LOCATION: (7)..(7)
<223> OTHER INFORMATION: Lys(acetyl) in Peptide 3

<400> SEQUENCE: 10

Arg Lys Asp Leu Gly Trp Lys Trp
1               5

<210> SEQ ID NO 11
<211> LENGTH: 7
<212> TYPE: PRT
<213> ORGANISM: Homo sapiens
<220> FEATURE:
<221> NAME/KEY: SITE
<222> LOCATION: (5)..(5)
<223> OTHER INFORMATION: Lys(biotin) in Peptide 5

<400> SEQUENCE: 11

Ile His Glu Pro Lys Gly Tyr
1               5

<210> SEQ ID NO 12
<211> LENGTH: 10
<212> TYPE: PRT
<213> ORGANISM: Homo sapiens
<220> FEATURE:
<221> NAME/KEY: SITE
<222> LOCATION: (8)..(8)
<223> OTHER INFORMATION: Lys(biotin) in Peptide 6

<400> SEQUENCE: 12

Ser Leu Asp Thr Gln Tyr Ser Lys Val Leu
1               5                   10
```

-continued

```
<210> SEQ ID NO 13
<211> LENGTH: 11
<212> TYPE: PRT
<213> ORGANISM: Homo sapiens
<220> FEATURE:
<221> NAME/KEY: SITE
<222> LOCATION: (5)..(5)
<223> OTHER INFORMATION: Lys(biotin) in Peptide 7
<220> FEATURE:
<221> NAME/KEY: SITE
<222> LOCATION: (5)..(5)
<223> OTHER INFORMATION: Lys(acetyl) in Peptide 8
<220> FEATURE:
<221> NAME/KEY: SITE
<222> LOCATION: (7)..(7)
<223> OTHER INFORMATION: Lys(biotin) in Peptide 8
<220> FEATURE:
<221> NAME/KEY: SITE
<222> LOCATION: (7)..(7)
<223> OTHER INFORMATION: Lys(acetyl) in Peptide 7

<400> SEQUENCE: 13

Tyr Val Gly Arg Lys Pro Lys Val Glu Gln Leu
1               5                   10

<210> SEQ ID NO 14
<211> LENGTH: 11
<212> TYPE: PRT
<213> ORGANISM: Homo sapiens
<220> FEATURE:
<221> NAME/KEY: SITE
<222> LOCATION: (8)..(8)
<223> OTHER INFORMATION: Cys(carbamidomethyl) in Peptide 9
<220> FEATURE:
<221> NAME/KEY: SITE
<222> LOCATION: (9)..(9)
<223> OTHER INFORMATION: Lys(biotin) in Peptide 9
<220> FEATURE:
<221> NAME/KEY: SITE
<222> LOCATION: (10)..(10)
<223> OTHER INFORMATION: Cys(carbamidomethyl) in Peptide 9

<400> SEQUENCE: 14

Ser Asn Met Ile Val Arg Ser Cys Lys Cys Ser
1               5                   10

<210> SEQ ID NO 15
<211> LENGTH: 9
<212> TYPE: PRT
<213> ORGANISM: Artificial sequence
<220> FEATURE:
<223> OTHER INFORMATION: Motif of basic residues involved in heparin-
      binding
<220> FEATURE:
<221> NAME/KEY: VARIANT
<222> LOCATION: (1)..(1)
<223> OTHER INFORMATION: Xaa is any neutral or acidic amino acid
<220> FEATURE:
<221> NAME/KEY: VARIANT
<222> LOCATION: (2)..(4)
<223> OTHER INFORMATION: Xaa is a basic residue
<220> FEATURE:
<221> NAME/KEY: VARIANT
<222> LOCATION: (5)..(6)
<223> OTHER INFORMATION: Xaa is any neutral or acidic amino acid
<220> FEATURE:
<221> NAME/KEY: VARIANT
<222> LOCATION: (7)..(7)
<223> OTHER INFORMATION: Xaa is a basic residue
<220> FEATURE:
<221> NAME/KEY: VARIANT
<222> LOCATION: (8)..(9)
<223> OTHER INFORMATION: Xaa is any neutral or acidic amino acid

<400> SEQUENCE: 15
```

```
Xaa Xaa Xaa Xaa Xaa Xaa Xaa Xaa Xaa
1               5
```

<210> SEQ ID NO 16
<211> LENGTH: 7
<212> TYPE: PRT
<213> ORGANISM: Artificial sequence
<220> FEATURE:
<223> OTHER INFORMATION: Motif of basic residues involved in heparin-
      binding
<220> FEATURE:
<221> NAME/KEY: VARIANT
<222> LOCATION: (1)..(1)
<223> OTHER INFORMATION: Xaa is any neutral or acidic amino acid
<220> FEATURE:
<221> NAME/KEY: VARIANT
<222> LOCATION: (2)..(3)
<223> OTHER INFORMATION: Xaa is a basic residue
<220> FEATURE:
<221> NAME/KEY: VARIANT
<222> LOCATION: (4)..(4)
<223> OTHER INFORMATION: Xaa is any neutral or acidic amino acid
<220> FEATURE:
<221> NAME/KEY: VARIANT
<222> LOCATION: (5)..(5)
<223> OTHER INFORMATION: Xaa is a basic residue
<220> FEATURE:
<221> NAME/KEY: VARIANT
<222> LOCATION: (6)..(7)
<223> OTHER INFORMATION: Xaa is any neutral or acidic amino acid

<400> SEQUENCE: 16

```
Xaa Xaa Xaa Xaa Xaa Xaa Xaa
1               5
```

<210> SEQ ID NO 17
<211> LENGTH: 12
<212> TYPE: PRT
<213> ORGANISM: Artificial sequence
<220> FEATURE:
<223> OTHER INFORMATION: Motif of basic residues involved in heparin-
      binding
<220> FEATURE:
<221> NAME/KEY: VARIANT
<222> LOCATION: (1)..(1)
<223> OTHER INFORMATION: Xaa is any neutral or acidic amino acid
<220> FEATURE:
<221> NAME/KEY: VARIANT
<222> LOCATION: (2)..(2)
<223> OTHER INFORMATION: Xaa is a basic residue
<220> FEATURE:
<221> NAME/KEY: VARIANT
<222> LOCATION: (3)..(4)
<223> OTHER INFORMATION: Xaa is any neutral or acidic amino acid
<220> FEATURE:
<221> NAME/KEY: VARIANT
<222> LOCATION: (5)..(5)
<223> OTHER INFORMATION: Xaa is a basic residue
<220> FEATURE:
<221> NAME/KEY: VARIANT
<222> LOCATION: (6)..(7)
<223> OTHER INFORMATION: Xaa is any neutral or acidic amino acid
<220> FEATURE:
<221> NAME/KEY: VARIANT
<222> LOCATION: (8)..(8)
<223> OTHER INFORMATION: Xaa is a basic residue
<220> FEATURE:
<221> NAME/KEY: VARIANT
<222> LOCATION: (9)..(10)
<223> OTHER INFORMATION: Xaa is any neutral or acidic amino acid
<220> FEATURE:
<221> NAME/KEY: VARIANT
<222> LOCATION: (11)..(11)
<223> OTHER INFORMATION: Xaa is a basic residue
<220> FEATURE:

```
<221> NAME/KEY: VARIANT
<222> LOCATION: (12)..(12)
<223> OTHER INFORMATION: Xaa is any neutral or acidic amino acid

<400> SEQUENCE: 17

Xaa Xaa Xaa Xaa Xaa Xaa Xaa Xaa Xaa Xaa Xaa Xaa
1               5                   10
```